US012753245B2

(12) United States Patent
Rose et al.

(10) Patent No.: US 12,753,245 B2
(45) Date of Patent: Oct. 6, 2026

(54) LUCIFERASE LINKED IMMUNOSORBENT ASSAY

(71) Applicant: INSTITUT PASTEUR, Paris (FR)

(72) Inventors: Thierry Rose, Paris (FR); Sophie Goyard, Paris (FR); Laurent Lionel Reber, Antony (FR); Yves Janin, Paris (FR)

(73) Assignee: INSTITUT PASTEUR, Paris (FR)

( * ) Notice: Subject to any disclaimer, the term of this patent is extended or adjusted under 35 U.S.C. 154(b) by 966 days.

(21) Appl. No.: 17/996,861

(22) PCT Filed: Apr. 26, 2021

(86) PCT No.: PCT/EP2021/060829

§ 371 (c)(1),
(2) Date: Oct. 21, 2022

(87) PCT Pub. No.: WO2021/219544

PCT Pub. Date: Nov. 4, 2021

(65) Prior Publication Data

US 2023/0145894 A1 May 11, 2023

(30) Foreign Application Priority Data

Apr. 27, 2020 (EP) .................................... 20315224

(51) Int. Cl.

*C07K 16/42* (2006.01)
*C12N 9/02* (2006.01)
*G01N 33/533* (2006.01)
*G01N 33/535* (2006.01)
*G01N 33/577* (2006.01)

(52) U.S. Cl.

CPC ........ *C07K 16/4291* (2013.01); *C12N 9/0069* (2013.01); *G01N 33/533* (2013.01); *G01N 33/535* (2013.01); *G01N 33/577* (2013.01); *C07K 2317/22* (2013.01); *C07K 2317/622* (2013.01)

(58) Field of Classification Search

None
See application file for complete search history.

(56) References Cited

U.S. PATENT DOCUMENTS

2016/0355868 A1 12/2016 Inouye et al.

FOREIGN PATENT DOCUMENTS

| | | | | | |
|---|---|---|---|---|---|
| CN | 108593912 | A | | 9/2018 | |
| DE | 19508087 | A1 | * | 9/1996 | ............. C07K 16/18 |
| WO | 2012061530 | A2 | | 5/2012 | |
| WO | WO-2017173403 | A1 | * | 10/2017 | ....... G01N 33/56972 |
| WO | WO-2018197727 | A1 | * | 11/2018 | ......... A61K 49/0013 |

OTHER PUBLICATIONS

Skolnick et al., Trends in Biotechnology, 2000, 18(1):34-39.*
Whisstock et al., Quarterly Reviews of Biophysics, 2003, 36:307-340.*
Eom et al. Development of Recombinant Immunoglobulin G-Binding Luciferase-Based Signal Amplifiers in Immunoassays. Anal. Chem., 2020, 92, 5473-5481.
Coutant et al. Bioluminescence Profiling of NanoKAZ/NanoLuc Luciferase Using a Chemical Library of Coelenterazine Analogues. Chem. Eur. J., 2019, 26, 948-958.
Natarajan et al. A Fast and Sensitive Luciferase-based Assay for Antibody Engineering and Design of Chimeric Antigen Receptors. Scientific Reports, 2020, 10(2318), 1-13.
Jabs et al. rapping IgE in a closed conformation by mimicking CD23 binding prevents and disrupts FcεRI interaction. Nature Communications, 2018, 9(7), 1-11.
Goode et al. The development and optimisation of nanobody based electrochemical immunosensors forIgG. Sensors and Actuators B: Chemical, 2016, 234, 478-484.
Romao et al. Identification of Useful Nanobodies by Phage Display of Immune Single Domain Libraries Derived from Camelid Heavy Chain Antibodies. Current Pharmaceutical Design, 2016, 22, 6500-6518.
De Meyer et al. Nanobody-basedproducts as research and diagnostic tools. Trends in Biotechnology, 2014, 32(5), 263-270.
Rothbauer et al. Targeting and tracing antigens in live cells with fluorescent nanobodies. Nature Methods, 2006, 3(11), 887-889.
Inouye et al. Luminescenceenhancement of the catalytic 19kDa protein (KAZ) of Oplophorusluciferase by three amino acid substitutions. Biochemical and Biophysical Research Communications, 2014, 445(1), 157-162.
Hsien-Wei et al. Annual Review of Analytical Chemistry Development and Applications of Bioluminescent and Chemiluminescent Reporters and Biosensors. Annu. Rev. Anal. Chem, 2019, 12, 129-150.
Habib et al. VHH (nanobody) directed against human glycophorin A: A tool for autologous red cell agglutination assays, Analytical Biochemistry, 2013, 438, 82-89.
Lin et al. Detection of allergen component-specific immunoglobulin E with the luciferase immunoprecipitation systems immunoassay, bioRxiv, 2020, 917153, 1-10.
Canonica et al. A WAO-ARIA-GA(2)LEN consensus document on molecular-based allergy diagnostics. World Allergy Organ J. 2013;6(1):17.
Van Hage et al. ImmunoCAP assays: Pros and cons in allergology. J Allergy Clin Immunol. 2017;140(4):974-977.
Gasser et al. The mechanistic and functional profile of the therapeutic anti-IgE antibody ligelizumab differs from omalizumab. Nat Commun. 2020;11(1):165.
Mukai et al. Assessing basophil activation by using flow cytometry and mass cytometry in blood stored 24 hours before analysis. J Allergy Clin Immunol. 2017;139(3):889-899 e811.

(Continued)

*Primary Examiner* — Michael Szperka
(74) *Attorney, Agent, or Firm* — Arrigo, Lee, Guttman & Mouta-Bellum LLP

(57) ABSTRACT

The present invention relates to a fusion protein comprising: —a N-terminal domain which comprises an antibody which is a variable domain of a camelid heavy-chain antibody (VHH) or a single chain variable fragment (scFV) and which is directed against an immunoglobulin and —a C-terminal domain which comprises a polypeptide with a luciferase activity: —having the amino acid sequence SEQ ID NO: 1 or —having at least 80% amino acid sequence identity to the amino acid sequence SEQ ID NO: 1.

24 Claims, 17 Drawing Sheets

Specification includes a Sequence Listing.

(56) References Cited

OTHER PUBLICATIONS

Hamilton et al. In vitro assays for the diagnosis of IgE-mediated disorders. J Allergy Clin Immunol. 2004;114(2):213-225; quiz 226.
Tsai et al. Isotype-specific agglutination-PCR (ISAP): A sensitive and multiplex method for measuring allergen-specific IgE. J Allergy Clin Immunol. 2018;141(5):1901-1904 e1915.
Li et al. Development and validation of a third generation allergen-specific IgE assay on the continuous random access IMMULITE 2000 analyzer. Ann Clin Lab Sci. 2004;34(1):67-74.
Tomabechi et al. Crystal structure of nanoKAZ: The mutated 19 kDa component of Oplophorus luciferase catalyzing the bioluminescent reaction with coelenterazine. Biochem Biophys Res Commun. 2016;470(1):88-93.
Shimomura et al. Properties and reaction mechanism of the bioluminescence system of the deep-sea shrimp *Oplophorus gracilirostris* . . . Biochemistry. Mar. 21, 1978;17(6):994-8.
Hall et al. Engineered luciferase reporter from a deep sea shrimp utilizing a novel imidazopyrazinone substrate. ACS Chem Biol. Nov. 16, 2012;7(11):1848-57.

* cited by examiner

LUCIFERASE LINKED IMMUNOSORBENT ASSAY

FIELD OF THE INVENTION

The present invention relates to a method for detecting an immunoglobulin in a sample, the fusion protein to be used in this method as well as mutant luciferases with improved properties that notably can be used in this method.

BACKGROUND OF THE INVENTION

To test for evidence of past or present adaptive immune response to infection in a subject, serological assay against the infectious agent or allergen using either rapid diagnosis test or laboratory-based immunoassay formats must be performed.

There is wide range of serological tests on the market. For example, laboratory-based immunoassay may be enzyme immunoassay (EIA), radio-immunoassay (RIA), fluorescence immunoassay (FIA), chemoluminescence immunoassay (CLIA) or electroluminescence assay (ECL).

However, whatever the protocol used for the serological test, it has to meet safety, quality and performance standards (with regard to both analytical and clinical sensitivity and specificity).

Most standard serological tests on the market for detecting and/or quantifying an immunoglobulin indicative of a past or present infection are sensitive but they require relatively large amount of plasma (which can be problematic when testing young children), and are also limited by their cost and the need for a specific instrument to analyze the test's results. Therefore, further developments are needed to improve the sensitivity of serological test, while markedly reducing the volume of sample required and the cost, without sacrificing assay robustness, reproducibility and accuracy.

SUMMARY OF THE INVENTION

Now, the applicant has found that by fusing a variable domain of a camelid heavy-chain antibody (VHH) to a luciferase derived from the catalytic domain of Oplophorus *gracilirostris* luciferase, it can be performed the detection of specific immunoglobulin in reduced sample volume while keeping the required specificity and sensitivity with an increased dynamic range and a shorter time of assay. The serological assay designs by the application may be used in rapid diagnosis test. It is thus possible to design assays for detecting and/quantifying immunoglobulins specific for any infectious disease of interest but also allergy or autoimmune diseases.

A subject of the present invention is therefore a fusion protein comprising:

- a N-terminal domain which comprises an antibody which is a variable domain of a camelid heavy-chain antibody (VHH) or a single chain variable fragment (scFV) and which is directed against an immunoglobulin and

- a C-terminal domain which comprises a polypeptide with a luciferase activity:
  - having the amino acid sequence SEQ ID NO: 1 or
  - having at least 80% amino acid sequence identity to the amino acid sequence SEQ ID NO: 1.

The applicant has also found that the results of its serological test are ever improved using specific mutants of the NanoKAZ luciferase.

Thus, the present invention also relates to a luciferase having at least 80% amino acid sequence identity to the amino acid sequence SEQ ID NO: 1 and comprising at least one amino acid substitution selected from the group consisting of:

- substitution of the tyrosine (Y) at a position corresponding to the position 18 of SEQ ID NO: 1 with an arginine (R),
- substitution of the leucine (L) at a position corresponding to the position 48 of SEQ ID NO: 1 with a lysine (K),
- substitution of the isoleucine (I) at a position corresponding to the position 56 of SEQ ID NO: 1 with an alanine (A),
- substitution of the tyrosine (Y) at a position corresponding to the position 116 of SEQ ID NO: 1 with a phenylalanine (F),
- substitution of the tryptophan (W) at a position corresponding to the position 134 of SEQ ID NO: 1 with an amino acid selected from the group consisting of a threonine (T) and glutamate (E),
- substitution of the tryptophan (W) at a position corresponding to the position 163 of SEQ ID NO: 1 with an amino acid selected from the group consisting of a threonine (T) and glutamate (E), and

- substitution of the cysteine (C) at a position corresponding to the position 166 of SEQ ID NO: 1 with a serine (S).

DETAILED DESCRIPTION OF THE INVENTION

Luciferase Mutants

"Luciferase" as used herein refers to a class of oxidative enzymes that produce bioluminescence. Bioluminescence is the emission of light produced in a biochemical reaction involving the oxidation of a substrate via an enzyme.

Luciferases encompass are commonly found in lower organisms such as bacteria, fungi, insects, dinoflagellates, radiolarians, cnidarians, crustaceans, jelly fishes and cephalopods. Among these various luciferases, the one from the deep sea shrimp Oplophorus had promising properties (Shimomura O, Masugi T, Johnson F H, Haneda Y., Properties and reaction mechanism of the bioluminescence system of the deep-sea shrimp Oplophorus *gracilirostris*. Biochemistry. 1978 Mar. 21; 17(6):994-8.). However, the 19 kDa subunit (KAZ) having the luciferase activity of this heterodimeric structure does not retain many of the desirable features of the native enzyme as it is unstable and poorly expressed in the absence of the regulatory subunit. The activity has been increased seven fold with the natural substrate coelenterazine by the three amino-acid substitutions V44I, A54I and Y138I (eKAZ) in the sequence of KAZ (Inouye S, Sato J, Sahara-Miura Y, Yoshida S, Hosoya T. Luminescence enhancement of the catalytic 19 kDa protein (KAZ) of Oplophorus luciferase by three amino acid substitutions. Biochem Biophys Res Commun. 2014; 445(1): 157-162.).

The folding of the enzyme has been optimized by the mutations of hydrophobic amino acids by hydrophilic residues at the protein surface: A4E, F68D, L72Q, M75K, P115E, and/or N166R.

Then, Hall et al. have engineered a luciferase derived from the 19 kDa subunit of the luciferase from Oplophorus with improved stability called nanoLuc, NLuc as well as nanoKAZ with the following mutations: A4E, Q11R, Q18L, L27V, A33N, K43R, V44I, A54I, F68D, L72Q, M75K, 190V, P115E, Q124K, Y138I, and N166R (Hall M P, Unch J, Binkowski B F, Valley M P, Butler B L, Wood M G, Otto P, Zimmerman K, Vidugiris G, Machleidt T, Robers M B, Benink H A, Eggers C T, Slater M R, Meisenheimer P L, Klaubert D H, Fan F, Encell L P, Wood K V. Engineered luciferase reporter from a deep sea shrimp utilizing a novel imidazopyrazinone substrate. ACS Chem Biol. 2012 Nov. 16; 7(11):1848-57).

However, the properties of the nanoKAZ luciferase still need to be improved.

Now, the applicant has found that the specific mutants of nanoKAZ have improved solubility and/or catalytic activity and/or photon emission per mol of catalyzed substrate compared to nanoKAZ especially with newly patented substrates (WO2018/197727, Coutant et al., 2019, 2020).

Thus, the present invention relates to a luciferase having at least 80%, at least 85%, at least 90%, at least 95%, at least 96%, at least 97%, at least 98% or at least 99% amino acid sequence identity to the amino acid sequence SEQ ID NO: 1 and comprising at least one amino acid substitution selected from the group consisting of:

- substitution of the tyrosine (Y) at a position corresponding to the position 18 of SEQ ID NO: 1 with an arginine (R),
- substitution of the leucine (L) at a position corresponding to the position 48 of SEQ ID NO: 1 with a lysine (K),
- substitution of the isoleucine (I) at a position corresponding to the position 56 of SEQ ID NO: 1 with an alanine (A),
- substitution of the tyrosine (Y) at a position corresponding to the position 116 of SEQ ID NO: 1 with a phenylalanine (F),
- substitution of the tryptophan (W) at a position corresponding to the position 134 of SEQ ID NO: 1 with an amino acid selected from the group consisting of a threonine (T) and glutamate (E),
- substitution of the tryptophan (W) at a position corresponding to the position 163 of SEQ ID NO: 1 with an amino acid selected from the group consisting of a threonine (T) and glutamate (E), and

- substitution of the cysteine (C) at a position corresponding to the position 166 of SEQ ID NO: 1 with a serine (S).

For the purposes of comparing two closely-related polynucleotide or polypeptide sequences, the "% identity" between a first sequence and a second sequence may be calculated using an alignment program, such as BLAST® (available at blast.ncbi.nlm.nih.gov, last accessed 9 Mar. 2015) using standard settings. The % identity is the number of identical residues divided by the number of residues in the reference sequence, multiplied by 100. The % identity figures referred to above and in the claims are percentages calculated by this methodology. An alternative definition of % identity is the number of identical residues divided by the number of aligned residues, multiplied by 100. Alternative methods include using a gapped method in which gaps in the alignment, for example deletions in one sequence relative to the other sequence, are accounted for in a gap score or a gap cost in the scoring parameter. For more information, see the BLAST® fact sheet available at ftp.ncbi.nlm.nih.gov/pub/factsheets/HowTo_BLASTGuide.pdf, last accessed on 9 Mar. 2015.

The luciferase may comprise at least 1, at least 2, at least 3, at least 4, at least 5, at least 6 or at least 7 or 1, 2, 3, 4, 5, 6 or 7 amino acid substitutions selected from the group consisting of:

- substitution of the tyrosine (Y) at a position corresponding to the position 18 of SEQ ID NO: 1 with an arginine (R),
- substitution of the leucine (L) at a position corresponding to the position 48 of SEQ ID NO: 1 with a lysine (K),
- substitution of the isoleucine (I) at a position corresponding to the position 56 of SEQ ID NO: 1 with an alanine (A),
- substitution of the tyrosine (Y) at a position corresponding to the position 116 of SEQ ID NO: 1 with a phenylalanine (F),
- substitution of the tryptophan (W) at a position corresponding to the position 134 of SEQ ID NO: 1 with an amino acid selected from the group consisting of a threonine (T) and glutamate (E),
- substitution of the tryptophan (W) at a position corresponding to the position 163 of SEQ ID NO: 1 with an amino acid selected from the group consisting of a threonine (T) and glutamate (E), and

- substitution of the cysteine (C) at a position corresponding to the position 166 of SEQ ID NO: 1 with a serine (S).

In one embodiment, the tryptophan (W) at a position corresponding to the position 134 of SEQ ID NO: 1 is substituted with a threonine (T). In an alternative embodiment, the tryptophan (W) at a position corresponding to the position 134 of SEQ ID NO: 1 is substituted with a glutamate (E), In one embodiment, the tryptophan (W) at a position corresponding to the position 163 of SEQ ID NO: 1 is substituted with a threonine (T). In an alternative embodiment, the tryptophan (W) at a position corresponding to the position 163 of SEQ ID NO: 1 is substituted with a glutamate (E), In one embodiment, the tyrosine (Y) at a position corresponding to the position 116 of SEQ ID NO: 1 is substituted with a phenylalanine (F).

In one embodiment, the tryptophan (W) at a position corresponding to the position 134 of SEQ ID NO: 1 is substituted with a threonine (T), In one embodiment, the tryptophan (W) at a position corresponding to the position 163 of SEQ ID NO: 1 is substituted with a threonine (T), In one embodiment, the isoleucine (I) at a position corresponding to the position 56 of SEQ ID NO: 1 with an alanine (A).

In one embodiment, the tyrosine (Y) at a position corresponding to the position 116 of SEQ ID NO: 1 is substituted with a phenylalanine (F) and the tryptophan (W) at a position corresponding to the position 134 of SEQ ID NO: 1 is substituted with a threonine (T), In one embodiment, the tyrosine (Y) at a position corresponding to the position 116 of SEQ ID NO: 1 is substituted with a phenylalanine (F) and the cysteine (C) at a position corresponding to the position 166 of SEQ ID NO: 1 is substituted with a serine (S).

In one embodiment, the tyrosine (Y) at a position corresponding to the position 18 of SEQ ID NO: 1 is substituted with an arginine (R), the leucine (L) at a position corresponding to the position 48 of SEQ ID NO: 1 is substituted with a lysine (K), the tryptophan (W) at a position corresponding to the position 134 of SEQ ID NO: 1 is substituted with a glutamate (E) and the tryptophan (W) at a position corresponding to the position 163 of SEQ ID NO: 1 is substituted with a glutamate (E).

In one embodiment, the tyrosine (Y) at a position corresponding to the position 18 of SEQ ID NO: 1 is substituted with an arginine (R), the leucine (L) at a position corresponding to the position 48 of SEQ ID NO: 1 is substituted with a lysine (K), the tryptophan (W) at a position corresponding to the position 134 of SEQ ID NO: 1 is substituted with a glutamate (E), the tryptophan (W) at a position corresponding to the position 163 of SEQ ID NO: 1 is substituted with a glutamate (E) and the cysteine (C) at a position corresponding to the position 166 of SEQ ID NO: 1 is substituted with a serine (S).

In one embodiment, the tyrosine (Y) at a position corresponding to the position 18 of SEQ ID NO: 1 is substituted with an arginine (R), the leucine (L) at a position corresponding to the position 48 of SEQ ID NO: 1 is substituted with a lysine (K), the tyrosine (Y) at a position corresponding to the position 116 of SEQ ID NO: 1 is substituted with a phenylalanine (F), the tryptophan (W) at a position corresponding to the position 134 of SEQ ID NO: 1 is substituted with a glutamate (E) and the tryptophan (W) at a position corresponding to the position 163 of SEQ ID NO: 1 is substituted with a glutamate (E).

In one embodiment, the tyrosine (Y) at a position corresponding to the position 18 of SEQ ID NO: 1 is substituted with an arginine (R), the leucine (L) at a position corresponding to the position 48 of SEQ ID NO: 1 is substituted with a lysine (K), the tyrosine (Y) at a position corresponding to the position 116 of SEQ ID NO: 1 is substituted with a phenylalanine (F), the tryptophan (W) at a position corresponding to the position 134 of SEQ ID NO: 1 is substituted with a glutamate (E), the tryptophan (W) at a position corresponding to the position 163 of SEQ ID NO: 1 is substituted with a glutamate (E) and the cysteine (C) at a position corresponding to the position 166 of SEQ ID NO: 1 is substituted with a serine (S).

The present invention also relates to a luciferase having an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO 17.

The amino acid sequence of the various luciferases are disclosed in the table 1 below.

TABLE 1

| Name (substitution) | SEQ ID NO | Amino acid sequence |
|---|---|---|
| NanoKAZ fused with a carboxy-end tag among those described farther | SEQ ID NO: 1 | MVFTLEDFVGDWRQTAGYNLDQVLEQGGVSSLFQNLGVSVTPIQRIVLSGENGLKIDIHV<br>IIPYEGLSGDQMGQIEKIFKVVYPVDDHHFKVILHYGTLVIDGVTPNMIDYFGRPYEGIA<br>VFDGKKITVTGTLWNGNKIIDERLINPDGSLLFRVTINGVTGWRLCERILALE |
| JAZ544 (Y116F) | SEQ ID NO: 2 | MVFTLEDFVGDWRQTAGYNLDQVLEQGGVSSLFQNLGVSVTPIQRIVLSGENGLKIDIHV<br>IIPYEGLSGDQMGQIEKIFKVVYPVDDHHFKVILHYGTLVIDGVTPNMIDYFGRPFEGIA<br>VFDGKKITVTGTLWNGNKIIDERLINPDGSLLFRVTINGVTGWRLCERILALE |
| JAZ583 (W134T) | SEQ ID NO: 3 | MVFTLEDFVGDWRQTAGYNLDQVLEQGGVSSLFQNLGVSVTPIQRIVLSGENGLKIDIHV<br>IIPYEGLSGDQMGQIEKIFKVVYPVDDHHFKVILHYGTLVIDGVTPNMIDYFGRPYEGIA<br>VFDGKKITVTGTLTNGNKIIDERLINPDGSLLFRVTINGVTGWRLCERILALE |
| JAZ584 (W163T) | SEQ ID NO: 4 | MVFTLEDFVGDWRQTAGYNLDQVLEQGGVSSLFQNLGVSVTPIQRIVLSGENGLKIDIHV<br>IIPYEGLSGDOMGQIEKIFKVVYPVDDHHFKVILHYGTLVIDGVTPNMIDYFGRPYEGIA<br>VFDGKKITVTGTLWNGNKIIDERLINPDGSLLFRVTINGVTG**T**RLCERILALE |
| JAZ560 I56A | SEQ ID NO: 5 | MVFTLEDFVGDWRQTAGYNLDQVLEQGGVSSLFQNLGVSVTPIQRIVLSGENGLK**A**DIHV<br>IIPYEGLSGDOMGQIEKIFKVVYPVDDHHFKVILHYGTLVIDGVTPNMIDYFGRPYEGIA<br>VFDGKKITVTGTLWNGNKIIDERLINPDGSLLFRVTINGVTGWRLCERILALE |
| JAZ585 (Y116F and W134T) | SEQ ID NO: 6 | MVFTLEDFVGDWRQTAGYNLDQVLEQGGVSSLFQNLGVSVTPIQRIVLSGENGLKIDIHV<br>IIPYEGLSGDQMGQIEKIFKVVYPVDDHHFKVILHYGTLVIDGVTPNMIDYFGRPFEGIA<br>VFDGKKITVTGTL**T**NGNKIIDERLINPDGSLLFRVTINGVTGWRLCERILALE |
| JAZ619 (Y116F and C166S) | SEQ ID NO: 7 | MVFTLEDFVGDWRQTAGYNLDQVLEQGGVSSLFQNLGVSVTPIQRIVLSGENGLKIDIHV<br>IIPYEGLSGDOMGQIEKIFKVVYPVDDHHFKVILHYGTLVIDGVTPNMIDYFGRP**F**EGIA<br>VFDGKKITVTGTLWNGNKIIDERLINPDGSLLFRVTINGVTGWRL**S**ERILALE |
| JAZ536 (Y18R, L48K, W134E and W163E) | SEQ ID NO: 8 | MVFTLEDFVGDWRQTAG**R**NLDQVLEQGGVSSLFQNLGVSVTPIQRIV**K**SGENGLKIDIHV<br>IIPYEGLSGDQMGQIEKIFKVVYPVDDHHFKVILHYGTLVIDGVTPNMIDYFGRPYEGIA<br>VFDGKKITVTGTL**E**NGNKIIDERLINPDGSLLFRVTINGVTG**E**RLCERILALE |
| JAZ570 (Y18R, L48K, W134E, W163E and C166S) | SEQ ID NO: 9 | MVFTLEDFVGDWRQTAG**R**NLDQVLEQGGVSSLFQNLGVSVTPIQRI**VK**SGENGLKIDIHV<br>IIPYEGLSGDQMGQIEKIFKVVYPVDDHHFKVILHYGTLVIDGVTPNMIDYFGRPYEGIA<br>VFDGKKITVTGTL**E**NGNKIIDERLINPDGSLLFRVTINGVTG**E**RL**S**ERILALE |
| JAZ572 (Y18R, L48K, Y116F, W134E and W163E) | SEQ ID NO: 10 | MVFTLEDFVGDWRQTAG**R**NLDQVLEQGGVSSLFQNLGVSVTPIQRIV**K**SGENGLKIDIHV<br>IIPYEGLSGDQMGQIEKIFKVVYPVDDHHFKVILHYGTLVIDGVTPNMIDYFGRP**F**EGIA<br>VFDGKKITVTGTL**E**NGNKIIDERLINPDGSLLFRVTINGVT**G**ERLCERILALE |

TABLE 1-continued

| Name (substitution) | SEQ ID NO | Amino acid sequence |
|---|---|---|
| JAZ573 (Y18R, L48K, Y116F, W134E, W163E, and C166S) | SEQ ID NO: 11 | MVFTLEDFVGDWRQTAG**R**NLDQVLEQGGVSSLFQNLGVSVTPIQRIV**K**SGENGLKIDIHV<br>IIPYEGLSGDQMGQIEKIFKVVYPVDDHHFKVILHYGTLVIDGVTPNMIDYFGRP**F**EGIA<br>VFDGKKITVTGTL**E**NGNKIIDERLINPDGSLLFRVTINGVTG**E**RL**S**ERILALE |
| JAZ*001 (Y18R) | SEQ ID NO: 12 | MVFTLEDFVGDWRQTAG**R**NLDQVLEQGGVSSLFQNLGVSVTPIQRIVLSGENGLKIDIHV<br>IIPYEGLSGDQMGQIEKIFKVVYPVDDHHFKVILHYGTLVIDGVTPNMIDYFGRPYEGIA<br>VFDGKKITVTGTLWNGNKIIDERLINPDGSLLFRVTINGVTGWRLCERILALE |
| JAZ*002 (L48K) | SEQ ID NO: 13 | MVFTLEDFVGDWRQTAGYNLDQVLEQGGVSSLFQNLGVSVTPTQRTV**K**SGENGLKIDIHV<br>IIPYEGLSGDOMGQIEKIFKVVYPVDDHHFKVILHYGTLVIDGVTPNMIDYFGRPYEGIA<br>VFDGKKITVTGTLWNGNKIIDERLINPDGSLLFRVTINGVTGWRLCERILALE |
| JAZ*003 (I56A and W163T) | SEQ ID NO: 14 | MVFTLEDFVGDWRQTAGYNLDQVLEQGGVSSLFQNLGVSVTPIQRIVLSGENGLK**A**DIHV<br>IIPYEGLSGDQMGQIEKIFKVVYPVDDHHFKVILHYGTLVIDGVTPNMIDYFGRPYEGIA<br>VFDGKKITVTGTLWNGNKIIDERLINPDGSLLFRVTINGVTG**T**RLCERILALE |
| JAZ*004 (W134E) | SEQ ID NO: 15 | MVFTLEDFVGDWRQTAGYNLDQVLEQGGVSSLFQNLGVSVTPIQRIVLSGENGLKIDIHV<br>IIPYEGLSGDQMGQIEKIFKVVYPVDDHHFKVILHYGTLVIDGVTPNMIDYFGRPYEGIA<br>VFDGKKITVTGTL**E**NGNKIIDERLINPDGSLLFRVTINGVTGWRLCERILALE |
| JAZ005 (W163E) | SEQ ID NO: 16 | MVFTLEDFVGDWRQTAGYNLDQVLEQGGVSSLFQNLGVSVTPIQRIVLSGENGLKIDIHV<br>IIPYEGLSGDQMGQIEKIFKVVYPVDDHHFKVILHYGTLVIDGVTPNMIDYFGRPYEGIA<br>VFDGKKITVTGTLWNGNKIIDERLINPDGSLLFRVTINGVTG**E**RLCERILALE |
| JAZ*006 (C166S) | SEQ ID NO: 17 | MVFTLEDFVGDWRQTAGYNLDQVLEQGGVSSLFQNLGVSVTPIQRIVLSGENGLKIDIHV<br>IIPYEGLSGDQMGQIEKIFKVVYPVDDHHFKVILHYGTLVIDGVTPNMIDYFGRPYEGIA<br>VFDGKKITVTGTLWNGNKIIDERLINPDGSLLFRVTINGVTGWRL**S**ERILALE |

Preferably, the luciferase has the amino acid sequence SEQ ID NO: 1 to SEQ ID NO: 11, more preferably SEQ ID NO: 2, SEQ ID NO: 6, SEQ ID NO: 8, SEQ ID NO: 10 or SEQ ID NO: 11. Most preferably the luciferase has the amino acid sequence SEQ ID NO: 8, SEQ ID NO: 11 or SEQ ID NO: 6

The present invention also relates to a polypeptide having a luciferase activity comprising 2 or 3 amino acid sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO 17.

Such polypeptide may have the amino acid sequence selected from the group consisting of SEQ ID NO: 42, SEQ ID NO: 43, SEQ ID NO: 44 and SEQ ID NO: 45. The present invention also relates to a polypeptide with a luciferase activity having the amino acid sequence SEQ ID NO: 46.

TABLE 2

| Name (mutation) | SEQ ID NO | Amino acid sequence |
|---|---|---|
| JAZ621 (duplication of SEQ ID NO: 1) | SEQ ID NO: 42 | MVFTLEDFVGDWRQTAGYNLDQVLEQGGVSSLFQNLGVSVTPIQRIVLSGENGLKIDIHVIIPYEGLSGDQM<br>GQIEKIFKVVYPVDDHHFKVILHYGTLVIDGVTPNMIDYFGRPYEGIAVFDGKKITVTGTLWNGNKIIDERL<br>INPDGSLLFRVTINGVTGWRLCERILA**GGSPG**VFTLEDFVGDWRQTAGYNLDQVLEQGGVSSLFQNLGVSVT<br>PIQRIVLSGENGLKIDIHVIIPYEGLSGDQMGQIEKIFKVVYPVDDHHFKVILHYGTLVIDGVTPNMIDYFG<br>RPYEGTAVFDGKKTTVTGTLWNGNKITDERLINPDGSLLFRVTINGVTGWRLCERILAV |
| JAZ622 (double substitution of the tyrosine (Y) at position 116 and 291 by a phenylalanine (F) in the duplication of SEQ ID NO: 1) | SEQ ID NO: 43 | MVFTLEDFVGDWRQTAGYNLDQVLEQGGVSSLFQNLGVSVTPTQRIVLSGENGLKIDIHVIIPYEGLSGDQM<br>GQIEKIFKVVYPVDDHHFKVILHYGTLVIDGVTPNMIDYFGRP**F**EGIAVFDGKKITVTGTLWNGNKIIDERL<br>INPDGSLLFRVTINGVTGWRLCERILA**GGSPG**VFTLEDFVGDWRQTAGYNLDQVLEQGGVSSLFQNLGVSVT<br>PIQRIVLSGENGLKIDIHVIIPYEGLSGDQMGQIEKIFKVVYPVDDHHFKVILHYGTLVIDGVTPNMIDYFG<br>RP**F**EGIAVFDGKKITVTGTLWNGNKIIDERLINPDGSLLFRVTINGVTGWRLCERILAV |
| JAZ476 (triplication of SEQ ID NO: 1) | SEQ ID NO: 44 | MVFTLEDFVGDWRQTAGYNLDQVLEQGGVSSLFQNLGVSVTPTQRIVLSGENGLKIDIHVIIPYEGLSGDQM<br>GQIEKIFKVVYPVDDHHFKVILHYGTLVIDGVTPNMIDYFGRP**Y**EGIAVFDGKKITVTGTLWNGNKIIDERL<br>INPDGSLLFRVTINGVTGWRLCERILA**GGSPG**VFTLEDFVGDWRQTAGYNLDQVLEQGGVSSLFQNLGVSVT<br>PIQRIVLSGENGLKIDIHVIIPYEGLSGDQMGQIEKIFKVVYPVDDHHFKVILHYGTLVIDGVTPNMIDYFG<br>RP**Y**EGIAVFDGKKITVTGTLWNGNKIIDERLINPDGSLLFRVTINGVTGWRLCERILANAGAQVFTLEDFVG<br>DWRQTAGYNLDQVLEQGGVSSLFQNLGVSVTPIQRIVLSGENGLKIDIHVIIPYEGLSGDQMGQIEKIFKVV<br>YPVDDHHFKVILHYGTLVIDGVTPNMIDYFGRP**Y**EGIAVFDGKKITVTGTLWNGNKIIDERLINPDGSLLFR<br>VTINGVTGWRLCERIL<br>AV |

TABLE 2-continued

| Name (mutation) | SEQ ID NO | Amino acid sequence |
|---|---|---|
| JAZ620 (triple substitution of the tyrosine (Y) at position 116, 291 and 466 by a phenylalanine (F) in the triplication of SEQ ID NO: 1) | SEQ ID NO: 45 | MVFTLEDFVGDWRQTAGYNLDQVLEQGGVSSLFQNLGVSVTPTQRTVLSGENGLKIDIHVIIPYEGLSGDQM<br>GQIEKIFKVVYPVDDHHFKVILHYGTLVIDGVTPNMIDYFGRP**F**EGIAVFDGKKITVTGTLWNGNKIIDERL<br>INPDGSLLFRVTINGVTGWRLCERILA**GGSPG**VFTLEDFVGDWRQTAGYNLDQVLEQGGVSSLFQNLGVSVT<br>PIQRIVLSGENGLKIDIHVIIPYEGLSGDQMGQIEKIFKVVYPVDDHHFKVILHYGTLVIDGVTPNMIDYFG<br>RP**F**EGIAVFDGKKITVTGTLWNGNKIIDERLINPDGSLLFRVTINGVTGWRLCERILA**NAGAQ**VFTLEDFVG<br>DWRQTAGYNLDQVLEQGGVSSLFQNLGVSVTPIQRIVLSGENGLKIDIHVIIPYEGLSGDQMGQIEKIFKW<br>YPVDDHHFKVILHYGTLVIDGVTPNMIDYFGRP**F**EGIAVFDGKKITVTGTLWNGNKIIDERLINPDGSLLFR<br>VTINGVTGWRLCERIL<br>AV |
| Scorpii68 (substitutions of the tyrosine (Y) at position 361 by a phenylalanine (F) of Antares sequence encompassing SEQ ID NO: 1 (2016 Jul.; 34(7):760-7.Chu J, Oh Y, Sens A, Ataie N, Dana H, Macklin JJ, Laviv T, Welf ES, Dean KM, Zhang F, Kim BB, Tang CT, Hu M, Baird MA, Davidson MW, Kay MA, Fiolka R, Yasuda R, Kim DS, Ng HL, Lin MZ Nat Biotechnol. 2016) | SEQ ID NO: 46 | **MTGGQQMGRDLYDDDDKDPMVSKGEELIKENMRSKLYLEGSVNGHQFKCTHEGEGKPYEGKQTNRIKVVEGG**<br>**PLPFAFDILATHFMYGSKVFIKYPADLPDYFKQSFPEGFTWERVMVFEDGGVLTATQDTSLQDGELIYNVKV**<br>**RGVNFPANGPVMQKKTLGWEPSTETMYPADGGLEGRCDKALKLVGGGHLHVNFKTTYKSKKPVKMPGVHYVD**<br>**RRLERIKEADNETYVEQYEHAVARYSNLGGG**FTLEDFVGDWRQTAGYNLDQVLEQGGVSSLFQNLGVSVTPI<br>QRIVLSGENGLKIDIHVIIPYEGLSGDQMGQIEKIFKVVYPVDDHHFKVILHYGTLVIDGVTPNMIDYFGRP<br>**F**EGIAVFDGKKITVTGTLWNGNKIIDERLINPDGSLLFRVTINGVTGWRLCERILA**RHELIKENMRSKLYLE**<br>**GSVNGHQFKCTHEGEGKPYEGKQTNRIKVVEGGPLPFAFDILATHFMYGSKVFIKYPADLPDYFKQSFPEGE**<br>**TWERVMVFEDGGVLTATQDTSLQDGELIYNVKVRGVNFPANGPVMQKKTLGWEPSTETMYPADGGLEGRCDK**<br>**ALKLVGGGHLHVNFKTTYKSKKPVKMPGVHYVDRRLERIKEADNETYVEQYEHAVARYSNLGGGMDELYK** |

The luciferase of the invention may have one or more heterologous amino acid sequences at the N-terminus, C-terminus, or both, which optionally directly or indirectly interact with a molecule of interest. The heterologous sequence may be a tag, such as a tag for purification purpose or a peptide or protein of interest. The luciferase may be also linked to an organic molecule (such as an organic molecule binder).

Affinity tags may be used at the C-end of the luciferase amino-acid sequence for purification, for secondary binding probe, for bead binding, for solid substrate binding purpose. Examples of amino acid sequence of such tags are given in the table 3 below.

TABLE 3

| Name | SEQ ID NO | Amino acid sequence |
|---|---|---|
| HIS-TAG | SEQ ID NO: 18 | HHHHHH |
| AviTAG | SEQ ID NO: 19 | GLNDIFEAQKIEWHE |
| SBP37 | SEQ ID NO: 20 | DEKTTGWRGGHVVEGLAG ELEQLRARLEHHPQGQREP |
| Twin-Strep-Tag | SEQ ID NO: 21 | WSHPQFEKGGGSGGGSGG SAWSHPQFEK |
| HA-Tag | SEQ ID NO: 22 | YPYDVPDYA |
| MYC-Tag | SEQ ID NO: 23 | EQKLISEEDL |

The peptide or protein of interest may be selected from the group consisting for a variable domain of a camelid heavy-chain antibody (VHH), a single-chain variable fragment (scFv), a variable regions of a heavy chain (VH), an immunoglobulin (Ig), interleukine, cytokine, chemokine, receptor ectodomain, peptidic antigen, peptidic allergen, receptor ectodomain, viral capsid peptidic fragment, bacteria surface peptidic fragment and cell surface peptidic fragment but not limited to.

Linkers may be inserted in between the amino-end of the peptide of interest (e.g. VHH, scFv, VH, Ig but not limited to) or the organic molecule binder and the carboxy-end luciferase for articulating the two domains. Linkers may have from 0 to 10 residues. In one embodiment, the amino-end of the peptide of interest or the organic molecule binder and the carboxy-end luciferase amino-acid sequence for articulating the two domains may be linked directly, without the use of a linker.

The amino acid sequence of linkers are disclosed in the table 4 below.

TABLE 4

| Amino acid sequence of linker | |
|---|---|
| SEQ ID NO: | Amino acid sequence |
| — | No linker |
| GS | GS |
| AAA | AAA |
| SEQ ID NO: 24 | AAAGS |
| SEQ ID NO: 25 | GGGGS |
| SEQ ID NO: 26 | GGGGSGGGGS |

When necessary or required for detection or measurement purpose linkers are inserted in between the amino-end protein binder domain (VHH, scFv, VH, Ig but not limited to), organic molecule binder or peptidic sequence of interest and the carboxy-end luciferase articulating the two domains with a protease-specific cleavage site for luciferase releasing purpose. Amino acid sequence of such thrombin-specific cleavable linkers are the following with from 5 to 14 residues. Thrombin cleavage sites are disclosed in the table 5 below.

TABLE 5

| Thrombin cleavage sites | | |
|---|---|---|
| Name | SEQ ID NO: | Amino acid sequence |
| Thrombin cleavage site | SEQ ID NO: 27 | LVPRG |
| GS-Thrombin cleavage site-GS | SEQ ID NO: 28 | GSLVPRGS |
| AAAGS-Thrombin cleavage site-GS | SEQ ID NO: 29 | AAAGSLVPRGS |
| G4S-Thrombin cleavage site-G4S | SEQ ID NO: 30 | GGGGSLVPRGG GGS |

In particular, the present invention also relates to a fusion protein comprising the luciferase of the invention. The luciferase may be linked to a peptide of interest.

As mentioned above, the peptide of interest may be selected from the group consisting for a variable domain of a camelid heavy-chain antibody (VHH), a single-chain variable fragment (scFv), a variable regions of a heavy chain (VH), an immunoglobulin (Ig), interleukine, cytokine, chemokine, receptor ectodomain, peptidic antigen, peptidic allergen, receptor ectodomain, viral capsid peptidic fragment, bacteria surface peptidic fragment and cell surface peptidic fragment but not limited to.

Suitably the luciferase or the fusion protein comprising the luciferase of the invention are recombinant. Recombinant means that the luciferase or the fusion protein is the product of at least one of mutation or cloning steps, or other procedures that result in a luciferase that is distinct from a luciferase found in nature, in particular distinct from the luciferase of Oplophorus found in the nature.

The present invention also relates to a polynucleotide encoding the luciferase of the invention or the fusion protein comprising the luciferase of the invention.

Suitably the polynucleotides of the invention are recombinant. As mentioned above, recombinant means that the polynucleotide is the product of at least one of cloning, restriction or ligation steps, or other procedures that result in a polynucleotide that is distinct from a polynucleotide found in nature.

The polynucleotide may further encode a polypeptide of interest linked to the luciferase, wherein the polypeptide of interest and the luciferase are capable of being expressed as a fusion protein.

Advantageously, the polynucleotide may be codon-optimized for expression of the luciferase of the invention or of the fusion protein comprising the luciferase in a host cell.

The polynucleotide of interest may comprise a nucleotide sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 60, SEQ ID NO: 61 and SEQ ID NO: 62. These nucleotide sequences of embodiments of expression-optimized polynucleotide are summarized in the table 6 below.

TABLE 6

| Name of the corres-ponding luciferase (substi-tution) | SEQ ID NO | Nucleotide sequence |
|---|---|---|
| JAZ526-NanoKAZ fused with a carboxy-end tag amongthose described above | SEQ ID NO: 31 | ATGGTTTTCACCCTTGAAGACTTCGTGGGC GACTGGCGCCAGACGGCGGGTTACAATCTC GATCAGGTGCTCGAACAAGGAGGTGTAAGT TCCCTGTTCCAAAACTTGGGGGTTTCTGTC ACTCCAATCCAGCGGATCGTGTTGAGCGGG GAAAATGGTTTAAAAATCGATATCCACGTG ATTATCCCGTATGAAGGCCTGTCAGGCGAC CAGATGGGACAGATAGAAAAAATCTTTAAA GTTGTATATCCGGTTGACGATCACCATTTT AAAGTAATCCTGCATTACGGCACCCTGGTG ATTGATGGGGTGACTCCTAACATGATTGAT TATTTTGGCCGTCCCTACGAAGGCATCGCA GTCTTTGATGGTAAAAAGATTACAGTGACG GGTACGCTATGGAACGGCAATAAGATTATT GATGAGCGTTTAATTAATCCGGATGGTTCG CTGCTGTTTCGCGTCACCATTAACGGTGTC ACCGGCTGGCGCCTGTGCGAGCGTATTCTG GCCCTCGAGCA |
| JAZ544 (Y116F) | SEQ ID NO: 32 | ATGGTTTTCACCCTTGAAGACTTCGTGGGC GACTGGCGCCAGACGGCGGGTTACAATCTC GATCAGGTGCTCGAACAAGGAGGTGTAAGT TCCCTGTTCCAAAACTTGGGGGTTTCTGTC ACTCCAATCCAGCGGATCGTGTTGAGCGGG GAAAATGGTTTAAAAATCGATATCCACGTG ATTATCCCGTATGAAGGCCTGTCAGGCGAC CAGATGGGACAGATAGAAAAAATCTTTAAA GTTGTATATCCGGTTGACGATCACCATTTT AAAGTAATCCTGCATTACGGCACCCTGGTG ATTGATGGGGTGACTCCTAACATGATTGAT TATTTTGGCCGTCCCTTTGAAGGCATCGCA GTCTTTGATGGTAAAAAGATTACAGTGACG GGTACGCTATGGAACGGCAATAAGATTATT GATGAGCGTTTAATTAATCCGGATGGTTCG CTGCTGTTTCGCGTCACCATTAACGGTGTC ACCGGCTGGCGCCTGTGCGAGCGTATTCTG GCCCTCGAGCA |
| JAZ583 W134T | SEQ ID NO: 33 | ATGGTTTTCACCCTTGAAGACTTCGTGGGC GACTGGCGCCAGACGGCGGGTTACAATCTC GATCAGGTGCTCGAACAAGGAGGTGTAAGT TCCCTGTTCCAAAACTTGGGGGTTTCTGTC ACTCCAATCCAGCGGATCGTGTTGAGCGGG GAAAATGGTTTAAAAATCGATATCCACGTG |

TABLE 6-continued

| Name of the corres-ponding luciferase (substi-tution) | SEQ ID NO | Nucleotide sequence |
|---|---|---|
| | | ATTATCCCGTATGAAGGCCTGTCAGGCGAC<br>CAGATGGGACAGATAGAAAAAATCTTTAAA<br>GTTGTATATCCGGTTGACGATCACCATTTT<br>AAAGTAATCCTGCATTACGGCACCCTGGTG<br>ATTGATGGGGTGACTCCTAACATGATTGAT<br>TATTTTGGCCGTCCCTACGAAGGCATCGCA<br>GTCTTTGATGGTAAAAAGATTACAGTGACG<br>GGTACGCTAACCAACGGCAATAAGATTATT<br>GATGAGCGTTTAATTAATCCGGATGGTTCG<br>CTGCTGTTTCGCGTCACCATTAACGGTGTC<br>ACCGGCTGGCGCCTGTGCGAGCGTATTCTG<br>GCCCTCGAGCA |
| JAZ584 W163T | SEQ ID NO: 34 | ATGGTTTTCACCCTTGAAGACTTCGTGGGC<br>GACTGGCGCCAGACGGCGGGTTACAATCTC<br>GATCAGGTGCTCGAACAAGGAGGTGTAAGT<br>TCCCTGTTCCAAAACTTGGGGGTTTCTGTC<br>ACTCCAATCCAGCGGATCGTGTTGAGCGGG<br>GAAAATGGTTTAAAAATCGATATCCACGTG<br>ATTATCCCGTATGAAGGCCTGTCAGGCGAC<br>CAGATGGGACAGATAGAAAAAATCTTTAAA<br>GTTGTATATCCGGTTGACGATCACCATTTT<br>AAAGTAATCCTGCATTACGGCACCCTGGTG<br>ATTGATGGGGTGACTCCTAACATGATTGAT<br>TATTTTGGCCGTCCCTACGAAGGCATCGCA<br>GTCTTTGATGGTAAAAAGATTACAGTGACG<br>GGTACGCTATGGAACGGCAATAAGATTATT<br>GATGAGCGTTTAATTAATCCGGATGGTTCG<br>CTGCTGTTTCGCGTCACCATTAACGGTGTC<br>ACCGGCTGGCGCCTGTGCGAGCGTATTCTG<br>GCCCTCGAGCA |
| JAZ560 I56A | SEQ ID NO: 35 | ATGGTTTTCACCCTTGAAGACTTCGTGGGC<br>GACTGGCGCCAGACGGCGGGTTACAATCTC<br>GATCAGGTGCTCGAACAAGGAGGTGTAAGT<br>TCCCTGTTCCAAAACTTGGGGGTTTCTGTC<br>ACTCCAATCCAGCGGATCGTGTTGAGCGGG<br>GAAAATGGTTTAAAAATCGATATCCACGTG<br>ATTATCCCGTATGAAGGCCTGTCAGGCGAC<br>CAGATGGGACAGATAGAAAAAATCTTTAAA<br>GTTGTATATCCGGTTGACGATCACCATTTT<br>AAAGTAATCCTGCATTACGGCACCCTGGTG<br>ATTGATGGGGTGACTCCTAACATGATTGAT<br>TATTTTGGCCGTCCCTTTGAAGGCATCGCA<br>GTCTTTGATGGTAAAAAGATTACAGTGACG<br>GGTACGCTATGGAACGGCAATAAGATTATT<br>GATGAGCGTTTAATTAATCCGGATGGTTCG<br>CTGCTGTTTCGCGTCACCATTAACGGTGTC<br>ACCGGCTGGCGCCTGTGCGAGCGTATTCTG<br>GCCCTCGAGCA |
| JAZ585 (Y116F and W134T) | SEQ ID NO: 36 | ATGGTTTTCACCCTTGAAGACTTCGTGGGC<br>GACTGGCGCCAGACGGCGGGTTACAATCTC<br>GATCAGGTGCTCGAACAAGGAGGTGTAAGT<br>TCCCTGTTCCAAAACTTGGGGGTTTCTGTC<br>ACTCCAATCCAGCGGATCGTGTTGAGCGGG<br>GAAAATGGTTTAAAAATCGATATCCACGTG<br>ATTATCCCGTATGAAGGCCTGTCAGGCGAC<br>CAGATGGGACAGATAGAAAAAATCTTTAAA<br>GTTGTATATCCGGTTGACGATCACCATTTT<br>AAAGTAATCCTGCATTACGGCACCCTGGTG<br>ATTGATGGGGTGACTCCTAACATGATTGAT<br>TATTTTGGCCGTCCCTTTGAAGGCATCGCA<br>GTCTTTGATGGTAAAAAGATTACAGTGACG<br>GGTACGCTAACCAACGGCAATAAGATTATT<br>GATGAGCGTTTAATTAATCCGGATGGTTCG<br>CTGCTGTTTCGCGTCACCATTAACGGTGTC<br>ACCGGCTGGCGCCTGTGCGAGCGTATTCTG<br>GCCCTCGAGCA |

TABLE 6-continued

| Name of the corres-ponding luciferase (substi-tution) | SEQ ID NO | Nucleotide sequence |
|---|---|---|
| JAZ619 Y116F and C166S | SEQ ID NO: 37 | ATGGTTTTCACCCTTGAAGACTTCGTGGGC<br>GACTGGCGCCAGACGGCGGGTTACAATCTC<br>GATCAGGTGCTCGAACAAGGAGGTGTAAGT<br>TCCCTGTTCCAAAACTTGGGGGTTTCTGTC<br>ACTCCAATCCAGCGGATCGTGTTGAGCGGG<br>GAAAATGGTTTAAAAATCGATATCCACGTG<br>ATTATCCCGTATGAAGGCCTGTCAGGCGAC<br>CAGATGGGACAGATAGAAAAAATCTTTAAA<br>GTTGTATATCCGGTTGACGATCACCATTTT<br>AAAGTAATCCTGCATTACGGCACCCTGGTG<br>ATTGATGGGGTGACTCCTAACATGATTGAT<br>TATTTTGGCCGTCCCTTTGAAGGCATCGCA<br>GTCTTTGATGGTAAAAAGATTACAGTGACG<br>GGTACGCTATGGAACGGCAATAAGATTATT<br>GATGAGCGTTTAATTAATCCGGATGGTTCG<br>CTGCTGTTTCGCGTCACCATTAACGGTGTC<br>ACCGGCTGGCGCCTGAGCGAGCGTATTCTG<br>GCCCTCGAGCA |
| JAZ536 Y18R, L48K, W134E and W163E | SEQ ID NO: 38 | ATGGTCTTCACATTAGAGGACTTTGTGGGA<br>GACTGGCGCCAAACCGCCGGGAGGAACTTG<br>GACCAGGTACTAGAGCAGGGCGGCGTAAGC<br>TCCTTGTTCCAGAATCTCGGAGTCAGTGTT<br>ACGCCGATCCAACGAATCGTTAAGTCTGGC<br>GAGAACGGACTTAAAATAGATATCCATGTG<br>ATTATACCCTACGAAGGTCTGTCAGGGGAT<br>CAGATGGGTCAGATTGAAAAGATCTTTAAG<br>GTGGTTTACCCCGTCGATGATCACCATTTT<br>AAAGTGATTCTCCACTACGGTACCCTTGTG<br>ATTGACGGGGTCACTCCAAACATGATAGAT<br>TATTTTGGCCGGCCTTATGAGGGAATTGCA<br>GTGTTCGATGGGAAAAAGATTACCGTGACC<br>GGCACTCTGGAAAACGGGAATAAGATCATC<br>GACGAACGTCTGATTAATCCTGACGGAAGC<br>CTGCTGTTCAGGGTGACAATCAATGGCGTG<br>ACAGGCGAGAGACTGTGCGAGAGAATCCTC<br>GCTCTCGAGCA |
| JAZ570 Y18R, L48K, W134E, W163E and C166S | SEQ ID NO: 39 | ATGGTCTTCACATTAGAGGACTTTGTGGGA<br>GACTGGCGCCAAACCGCCGGGAGGAACTTG<br>GACCAGGTACTAGAGCAGGGCGGCGTAAGC<br>TCCTTGTTCCAGAATCTCGGAGTCAGTGTT<br>ACGCCGATCCAACGAATCGTTAAGTCTGGC<br>GAGAACGGACTTAAAATAGATATCCATGTG<br>ATTATACCCTACGAAGGTCTGTCAGGGGAT<br>CAGATGGGTCAGATTGAAAAGATCTTTAAG<br>GTGGTTTACCCCGTCGATGATCACCATTTT<br>AAAGTGATTCTCCACTACGGTACCCTTGTG<br>ATTGACGGGGTCACTCCAAACATGATAGAT<br>TATTTTGGCCGGCCTTATGAGGGAATTGCA<br>GTGTTCGATGGGAAAAAGATTACCGTGACC<br>GGCACTCTGGAAAACGGGAATAAGATCATC<br>GACGAACGTCTGATTAATCCTGACGGAAGC<br>CTGCTGTTCAGGGTGACAATCAATGGCGTG<br>ACAGGCGAGAGACTGAGCGAGAGAATCCTC<br>GCTCTCGAGCA |
| JAZ572 Y18R, L48K, W134E, W163E and Y116F | SEQ ID NO: 40 | ATGGTCTTCACATTAGAGGACTTTGTGGGA<br>GACTGGCGCCAAACCGCCGGGAGGAACTTG<br>GACCAGGTACTAGAGCAGGGCGGCGTAAGC<br>TCCTTGTTCCAGAATCTCGGAGTCAGTGTT<br>ACGCCGATCCAACGAATCGTTAAGTCTGGC<br>GAGAACGGACTTAAAATAGATATCCATGTG<br>ATTATACCCTACGAAGGTCTGTCAGGGGAT<br>CAGATGGGTCAGATTGAAAAGATCTTTAAG<br>GTGGTTTACCCCGTCGATGATCACCATTTT<br>AAAGTGATTCTCCACTACGGTACCCTTGTG<br>ATTGACGGGGTCACTCCAAACATGATAGAT<br>TATTTTGGCCGGCCTTTTGAGGGAATTGCA<br>GTGTTCGATGGGAAAAAGATTACCGTGACC<br>GGCACTCTGGAAAACGGGAATAAGATCATC |

TABLE 6-continued

| Name of the corres-ponding luciferase (substi-tution) | SEQ ID NO | Nucleotide sequence |
|---|---|---|
| | | GACGAACGTCTGATTAATCCTGACGGAAGC<br>CTGCTGTTCAGGGTGACAATCAATGGCGTG<br>ACAGGCGAGAGACTGTGCGAGAGAATCCTC<br>GCTCTCGAGCA |
| JAZ573 Y18R, L48K, W134E, W163E, Y116F and C166S | SEQ ID NO: 41 | ATGGTCTTCACATTAGAGGACTTTGTGGGA<br>GACTGGCGCCAAACCGCCGGGAGGAACTTG<br>GACCAGGTACTAGAGCAGGGCGGCGTAAGC<br>TCCTTGTTCCAGAATCTCGGAGTCAGTGTT<br>ACGCCGATCCAACGAATCGTTAAGTCTGGC<br>GAGAACGGACTTAAAATAGATATCCATGTG<br>ATTATACCCTACGAAGGTCTGTCAGGGGAT<br>CAGATGGGTCAGATTGAAAAGATCTTTAAG<br>GTGGTTTACCCCGTCGATGATCACCATTTT<br>AAAGTGATTCTCCACTACGGTACCCTTGTG<br>ATTGACGGGGTCACTCCAAACATGATAGAT<br>TATTTTGGCCGGCCTTTTGAGGGAATTGCA<br>GTGTTCGATGGGAAAAAGATTACCGTGACC<br>GGCACTCTGGAAAACGGGAATAAGATCATC<br>GACGAACGTCTGATTAATCCTGACGGAAGC<br>CTGCTGTTCAGGGTGACAATCAATGGCGTG<br>ACAGGCGAGAGACTGAGCGAGAGAATCCTC<br>GCTCTCGAGCA |
| JAZ621 duplication of SEQ ID NO: 1 | SEQ ID NO: 60 | ATGGTCTTTACCTTGGAAGATTTCGTTGGA<br>GATTGGCGTCAGACTGCGGGTTATAATTTG<br>GACCAAGTGCTGGAACAAGGCGGCGTTAGT<br>AGCCTGTTTCAGAACCTGGGGGTGAGCGTC<br>ACGCCGATCCAGCGAATAGTTCTAAGCGGG<br>GAGAATGGACTAAAAATCGACATACATGTT<br>ATTATTCCCTACGAAGGCCTGAGCGGGGAC<br>CAGATGGGCCAGATTGAAAAAATTTTTAAA<br>GTTGTCTACCCTGTTGATGATCATCACTTC<br>AAAGTCATCCTCCATTATGGGACCCTCGTT<br>ATAGATGGGGTCACACCAAACATGATTGAC<br>TACTTCGGGAGGCCATACGAGGGCATAGCA<br>GTTTTCGATGGCAAGAAAATAACCGTCACA<br>GGCACTCTGTGGAATGGAAATAAGATCATC<br>GATGAGCGTCTTATAAATCCGGATGGGTCA<br>CTTCTCTTTCGCGTGACCATAAACGGCGTG<br>ACAGGGTGGCGCTTATGTGAACGGATCTTG<br>GCTGGGGGATCCCCTGGTGTTTTCACCCTC<br>GAAGACTTCGTTGGGGACTGGCGGCAAACA<br>GCTGGGTACAACCTAGACCAGGTACTGGAA<br>CAAGGAGGCGTCTCCTCATTGTTTCAGAAC<br>CTAGGTGTATCCGTGACCCCTATTCAGCGC<br>ATTGTGCTGTCCGGTGAAAACGGCCTCAAG<br>ATTGACATTCACGTGATAATCCCATATGAG<br>GGACTGTCAGGAGACCAGATGGGGCAGATT<br>GAAAAGATCTTTAAAGTCGTCTACCCCGTC<br>GACGATCACCACTTTAAGGTAATTCTGCAT<br>TACGGCACTTTGGTAATTGATGGTGTGACG<br>CCTAATATGATCGACTACTTCGGCCGGCCC<br>TACGAAGGGATAGCTGTCTTTGACGGCAAG<br>AAGATTACGGTCACCGGAACCCTGTGGAAT<br>GGCAACAAGATTATTGATGAGAGATTGATT<br>AATCCCGACGGTTCCCTGCTCTTCAGAGTC<br>ACTATTAACGGGGTAACCGGGTGGCGACTT<br>TGCGAGCGGATCCTGGCA |
| JAZ622 duplication of SEQ ID NO: 1 with (Y116F, Y291F) | SEQ ID NO: 61 | ATGGTCTTTACCTTGGAAGATTTCGTTGGA<br>GATTGGCGTCAGACTGCGGGTTATAATTTG<br>GACCAAGTGCTGGAACAAGGCGGCGTTAGT<br>AGCCTGTTTCAGAACCTGGGGGTGAGCGTC<br>ACGCCGATCCAGCGAATAGTTCTAAGCGGG<br>GAGAATGGACTAAAAATCGACATACATGTT<br>ATTATTCCCTACGAAGGCCTGAGCGGGGAC<br>CAGATGGGCCAGATTGAAAAAATTTTTAAA<br>GTTGTCTACCCTGTTGATGATCATCACTTC<br>AAAGTCATCCTCCATTATGGGACCCTCGTT<br>ATAGATGGGGTCACACCAAACATGATTGAC<br>TACTTCGGGAGGCCATTCGAGGGCATAGCA<br>GTTTTCGATGGCAAGAAAATAACCGTCACA<br>GGCACTCTGTGGAATGGAAATAAGATCATC<br>GATGAGCGTCTTATAAATCCGGATGGGTCA<br>CTTCTCTTTCGCGTGACCATAAACGGCGTG<br>ACAGGGTGGCGCTTATGTGAACGGATCTTG<br>GCTGGGGGATCCCCTGGTGTTTTCACCCTC<br>GAAGACTTCGTTGGGGACTGGCGGCAAACA<br>GCTGGGTACAACCTAGACCAGGTACTGGAA<br>CAAGGAGGCGTCTCCTCATTGTTTCAGAAC<br>CTAGGTGTATCCGTGACCCCTATTCAGCGC<br>ATTGTGCTGTCCGGTGAAAACGGCCTCAAG<br>ATTGACATTCACGTGATAATCCCATATGAG<br>GGACTGTCAGGAGACCAGATGGGGCAGATT<br>GAAAAGATCTTTAAAGTCGTCTACCCCGTC<br>GACGATCACCACTTTAAGGTAATTCTGCAT<br>TACGGCACTTTGGTAATTGATGGTGTGACG<br>CCTAATATGATCGACTACTTCGGCCGGCCC<br>TTCGAAGGGATAGCTGTCTTTGACGGCAAG<br>AAGATTACGGTCACCGGAACCCTGTGGAAT<br>GGCAACAAGATTATTGATGAGAGATTGATT<br>AATCCCGACGGTTCCCTGCTCTTCAGAGTC<br>ACTATTAACGGGGTAACCGGGTGGCGACTT<br>TGCGAGCGGATCCTGGCA |
| JAZ476 triplication of SEQ ID NO: 1 | SEQ ID NO: 62 | ATGGTCTTTACCTTGGAAGATTTCGTTGGA<br>GATTGGCGTCAGACTGCGGGTTATAATTTG<br>GACCAAGTGCTGGAACAAGGCGGCGTTAGT<br>AGCCTGTTTCAGAACCTGGGGGTGAGCGTC<br>ACGCCGATCCAGCGAATAGTTCTAAGCGGG<br>GAGAATGGACTAAAAATCGACATACATGTT<br>ATTATTCCCTACGAAGGCCTGAGCGGGGAC<br>CAGATGGGCCAGATTGAAAAAATTTTTAAA<br>GTTGTCTACCCTGTTGATGATCATCACTTC<br>AAAGTCATCCTCCATTATGGGACCCTCGTT<br>ATAGATGGGGTCACACCAAACATGATTGAC<br>TACTTCGGGAGGCCATACGAGGGCATAGCA<br>GTTTTCGATGGCAAGAAAATAACCGTCACA<br>GGCACTCTGTGGAATGGAAATAAGATCATC<br>GATGAGCGTCTTATAAATCCGGATGGGTCA<br>CTTCTCTTTCGCGTGACCATAAACGGCGTG<br>ACAGGGTGGCGCTTATGTGAACGGATCTTG<br>GCTGGGGGATCCCCTGGTGTTTTCACCCTC<br>GAAGACTTCGTTGGGGACTGGCGGCAAACA<br>GCTGGGTACAACCTAGACCAGGTACTGGAA<br>CAAGGAGGCGTCTCCTCATTGTTTCAGAAC<br>CTAGGTGTATCCGTGACCCCTATTCAGCGC<br>ATTGTGCTGTCCGGTGAAAACGGCCTCAAG<br>ATTGACATTCACGTGATAATCCCATATGAG<br>GGACTGTCAGGAGACCAGATGGGGCAGATT<br>GAAAAGATCTTTAAAGTCGTCTACCCCGTC<br>GACGATCACCACTTTAAGGTAATTCTGCAT<br>TACGGCACTTTGGTAATTGATGGTGTGACG<br>CCTAATATGATCGACTACTTCGGCCGGCCC<br>TACGAAGGGATAGCTGTCTTTGACGGCAAG<br>AAGATTACGGTCACCGGAACCCTGTGGAAT<br>GGCAACAAGATTATTGATGAGAGATTGATT<br>AATCCCGACGGTTCCCTGCTCTTCAGAGTC<br>ACTATTAACGGGGTAACCGGGTGGCGACTT<br>TGCGAGCGGATCCTGGCAAACGCCGGGGCC<br>CAGGTGTTTACCTTAGAGGACTTCGTAGGA<br>GATTGGCGCCAAACAGCCGGATACAACCTG<br>GACCAGGTGTTAGAGCAGGGCGGTGTGTCT<br>TCTCTTTTCCAGAATCTGGGTGTGTCTGTG<br>ACTCCAATCCAGAGAATCGTGCTTAGTGGA<br>GAGAATGGACTTAAAATCGACATCCATGTG<br>ATTATTCCTTATGAGGGTCTCAGTGGTGAC<br>CAAATGGGCCAGATCGAGAAAATTTTTAAG<br>GTGGTGTATCCTGTGGATGACCACCACTTC<br>AAGGTGATCCTCCACTATGGAACCCTCGTG<br>ATCGATGGAGTGACACCAAACATGATCGAC<br>TATTTCGGCAGGCCCTATGAGGGCATCGCA<br>GTGTTTGATGGAAAAAAGATCACTGTGACT |

TABLE 6-continued

| Name of the corres-ponding luciferase (substi-tution) | SEQ ID NO | Nucleotide sequence |
|---|---|---|
| | | GGAACACTGTGGAATGGCAATAAGATCATC GATGAGAGACTGATCAACCCCGATGGCTCT CTGCTGTTCAGAGTGACAATCAACGGCGTG ACAGGCTGGAGGCTGTGCGAGAGGATCCTG GCCgtttaa |

The present invention also relates to a vector comprising the polynucleotide of the invention.

As used herein, vector (or plasmid) refers to discrete elements that are used to introduce heterologous DNA into cells for either expression or replication thereof.

Selection and use of such vehicles are well-known to those of skill in the art. An expression vector includes vectors capable of expressing DNAs that are operatively linked with regulatory sequences, such as promoters, that are capable of effecting expression of such DNA fragments. Thus, an expression vector refers to a recombinant DNA construct, such as a plasmid, a phage, recombinant virus or other vector that, upon introduction into an appropriate host cell, results in expression of the cloned DNA. Appropriate expression vectors are well known to those of skill in the art.

A recombinant vector is a vector comprising a recombinant polynucleotide.

Advantageously, the vector comprises the polynucleotide operably linked to a promoter.

As used herein, operatively linked refers to the functional relationship of DNA with regulatory and effector sequences of nucleotides, such as promoters, enhancers, transcriptional and translational stop sites, and other signal sequences.

For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

As used herein, a promoter refers to a segment of DNA that controls transcription of the DNA to which it is operatively linked.

The polynucleotide or the vector of the invention may be into a cell, typically a prokaryote or eukaryote cell. The vector may be conservative in the cytoplasm or the polynucleotide could be integrated in the genome using lentiviral vector or genome edition (i.e. CRISPR-Cas9 but not limited to).

Therefore, the present invention also relates to a cell comprising the polynucleotide of the invention or the expression vector of the invention.

In one embodiment, the luciferase or the fusion protein comprising the luciferase is secreted from the prokaryotic or eukaryotic cell, expressed in the cytoplasm or in the periplasm in the case of bacteria.

In one embodiment, the luciferase or the fusion protein comprising the luciferase is synthesized in vitro using transcription and translation kit.

The present invention also relates to a non-human transgenic animal comprising the cell or the polynucleotide or the vector of the invention.

The present invention also relates to a kit comprising:

the luciferase, the fusion protein comprising the luciferase, the polynucleotide, the expression vector or the cell of the invention a substrate for the luciferase.

Preferably, the kit comprises the luciferase or the fusion protein and the substrate. Coelenterazine is the natural substrate for the shrimp Oplophorus luciferase but improvement in signals may be obtained with furimazine.

Consequently, the substrate may be selected from the group consisting of coelenterazine, furimazine or derivatives thereof.

Derivatives of furimazine and their O-acetylated moieties in their steady-state as pro-substrates are disclosed in the patent application WO2018/197727 A1. Such derivatives of furimazine provide a better bioluminescence signals in term of intensity, signal-to-noise ratio and/or duration.

Consequently, the substrate may be selected in the group consisting in:

8-benzyl-2-((5-methylfuran-2-yl)methyl)-6-phenylimidazo[1,2-a]pyrazin-3(7H)-one
8-benzyl-2-((5-ethylfuran-2-yl)methyl)-6-phenylimidazo[1,2-a]pyrazin-3(7H)-one
8-benzyl-2-((4,5-dimethylfuran-2-yl)methyl)-6-phenylimidazo[1,2-a]pyrazin-3(7H)-one
8-benzyl-6-(2-fluorophenyl)-2-(furan-2-ylmethyl)imidazo[1,2-a]pyrazin-3(7H)-one
8-benzyl-2-(3-methylbenzyl)-6-phenylimidazo[1,2-a]pyrazin-3(7H)-one
8-benzyl-2-(3-methoxybenzyl)-6-phenylimidazo[1,2-a]pyrazin-3(7H)-one
2,8-dibenzyl-6-(2-fluorophenyl)imidazo[1,2-a]pyrazin-3(7H)-one
8-benzyl-6-(2,6-difluorophenyl)-2-(furan-2-ylmethyl)imidazo[1,2-a]pyrazin-3(7H)-one
8-benzyl-6-phenyl-2-((5-(trifluoromethyl)furan-2-ylmethyl)imidazo[1,2-a]pyrazin-3(7H)-one
2,8-dibenzyl-6-(2,6-difluorophenyl)imidazo[1,2-a]pyrazin-3(7H)-one
8-benzyl-6-(2-fluorophenyl)-2-((5-methylfuran-2-yl)methyl)imidazo[1,2-a]pyrazin-3(7H)-one
8-benzyl-2-((5-cyclopropylfuran-2-yl)methyl)-6-phenylimidazo[1,2-a]pyrazin-3(7H)-one
8-benzyl-2-(3-fluorobenzyl)-6-phenylimidazo[1,2-a]pyrazin-3(7H)-one
8-benzyl-2-((5-ethylfuran-2-yl)methyl)-6-(2-fluorophenyl)imidazo[1,2-a]pyrazin-3(7H)-one
8-benzyl-6-(3-fluorophenyl)-2-((5-methylfuran-2-yl)methyl)imidazo[1,2-a]pyrazin-3(7H)-one
8-benzyl-2-(2-fluorobenzyl)-6-phenylimidazo[1,2-a]pyrazin-3(7H)-one
8-benzyl-2-((5-ethylthiophen-2-yl)methyl)-6-phenylimidazo[1,2-a]pyrazin-3(7H)-one
8-benzyl-2-((4,5-dimethylfuran-2-yl)methyl)-6-(2-fluorophenyl)imidazo[1,2-a]pyrazin-3(7H)-one
2-benzyl-8-(2-fluorobenzyl)-6-phenylimidazo[1,2-a]pyrazin-3(7H)-one
2-benzyl-8-(3-fluorobenzyl)-6-phenylimidazo[1,2-a]pyrazin-3(7H)-one
8-(3-fluorobenzyl)-2-(furan-2-ylmethyl)-6-phenylimidazo[1,2-a]pyrazin-3(7H)-one
8-(2-fluorobenzyl)-2-(3-methylbenzyl)-6-phenylimidazo[1,2-a]pyrazin-3(7H)-one
8-(2-fluorobenzyl)-2-(3-methoxybenzyl)-6-phenylimidazo[1,2-a]pyrazin-3(7H)-one
8-(2-fluorobenzyl)-2-(furan-2-ylmethyl)-6-phenylimidazo[1,2-a]pyrazin-3(7H)-one 8-(2-fluorobenzyl)-2-((5-methylfuran-2-yl)methyl)-6-phenylimidazo[1,2-a]pyrazin-3(7H)-one
8-(3-fluorobenzyl)-2-(3-methoxybenzyl)-6-phenylimidazo[1,2-a]pyrazin-3(7H)-one
8-(3-fluorobenzyl)-2-(3-methylbenzyl)-6-phenylimidazo[1,2-a]pyrazin-3(7H)-one
2-((5-ethylfuran-2-yl)methyl)-8-(3-fluorobenzyl)-6-phenylimidazo[1,2-a]pyrazin-3(7H)-one
8-(2-chlorobenzyl)-2-((5-methylfuran-2-yl)methyl)-6-phenylimidazo[1,2-a]pyrazin-3(7H)-one
8-(3-fluorobenzyl)-2-((5-methylfuran-2-yl)methyl)-6-phenylimidazo[1,2-a]pyrazin-3(7H)-one
2-((5-ethylfuran-2-yl)methyl)-8-(2-fluorobenzyl)-6-phenylimidazo[1,2-a]pyrazin-3(7H)-one
8-(3-fluorobenzyl)-6-(2-fluorophenyl)-2-((5-methylfuran-2-yl)methyl)imidazo[1,2-a]pyrazin-3(7H)-one
8-(2,3-difluorobenzyl)-2-(furan-2-ylmethyl)-6-phenylimidazo[1,2-a]pyrazin-3(7H)-one
8-(2,3-difluorobenzyl)-2-((5-methylfuran-2-yl)methyl)-6-phenylimidazo[1,2-a]pyrazin-3(7H)-one
2-benzyl-8-(2,3-difluorobenzyl)-6-phenylimidazo[1,2-a]pyrazin-3(7H)-one
8-(2,6-Difluorobenzyl)-2-((5-methylfuran-2-yl)methyl)-6-phenylimidazo[1,2-a]pyrazin-3(7H)-one
8-(2,3-Difluorobenzyl)-2-((4,5-dimethylfuran-2-yl)methyl)-6-phenylimidazo[1,2-a]pyrazin-3(7H)-one
8-(2,3-Difluorobenzyl)-2-((5-ethylfuran-2-yl)methyl)-6-phenylimidazo[1,2-a]pyrazin-3(7H)-one
8-(2,6-Difluorobenzyl)-2-((5-ethylfuran-2-yl)methyl)-6-phenylimidazo[1,2-a]pyrazin-3(7H)-one
2-((4,5-Dimethylfuran-2-yl)methyl)-8-(2-fluorobenzyl)-6-phenylimidazo[1,2-a]pyrazin-3(7H)-one
2-((4,5-Dimethylfuran-2-yl)methyl)-8-(3-fluorobenzyl)-6-phenylimidazo[1,2-a]pyrazin-3(7H)-one
8-(2,3-difluorobenzyl)-2-((4-ethyl-5-methylfuran-2-yl)methyl)-6-phenylimidazo[1,2-a]pyrazin-3(7H)-one
8-(2,3-difluorobenzyl)-2-((5-ethyl-4-methylfuran-2-yl)methyl)-6-phenylimidazo[1,2-a]pyrazin-3(7H)-one and
8-benzyl-2-(furan-2-ylmethyl)-6-(3-hydroxyphenyl)imidazo[1,2-a]pyrazin-3(7H)-one.

These substrates are respectively disclosed in WO2018/197727 A1 with the following names Q3, Q12, Q16, Q21, Q14, Q18, Q20, Q27, Q28, Q29, Q34, Q36, Q41, Q51, Q54, Q56, Q58, Q61, Q72, Q73, Q81, Q82, Q83, Q84, Q85, Q101, Q100, Q99, Q98, Q97, Q96, Q105, Q107, Q108, Q117, Q121, Q124, Q127, Q129, Q131, Q132, Q135, Q143 and Q149.

In a preferred embodiment, the substrate is 8-(2,3-difluorobenzyl)-2-((5-methylfuran-2-yl)methyl)-6-phenylimidazo[1,2-a]pyrazin-3(7H)-one (Q-108 as disclosed in Table 1 page 129 of WO2018/197727 A1).

The present invention also relates to a method for producing the luciferase of the invention comprising the step of:

providing a luciferase having the amino acid sequence SEQ ID NO: 1 or a variant thereof having at least 80%, at least 85%, at least 90%, at least 95%, at least 96%, at least 97%, at least 98% or at least 99% amino acid sequence identity to the amino acid sequence SEQ ID NO: 1 and at least 1, 2, 3, 4, 5, 6, 7 steps selected from the group consisting of;

substituting the tyrosine (Y) at a position corresponding to the position 18 of SEQ ID NO: 1 with an arginine (R), substituting the leucine (L) at a position corresponding to the position 48 of SEQ ID NO: 1 with a lysine (K), substituting the isoleucine (I) at a position corresponding to the position 56 of SEQ ID NO: 1 with an alanine (A), substituting the tyrosine (Y) at a position corresponding to the position 116 of SEQ ID NO: 1 with a phenylalanine (F), substituting the tryptophan (W) at a position corresponding to the position 134 of SEQ ID NO: 1 with an amino acid selected from the group consisting of a threonine (T) and glutamate (E), substituting the tryptophan (W) at a position corresponding to the position 163 of SEQ ID NO: 1 with an amino acid selected from the group consisting of a threonine (T) and glutamate (E), and substituting the cysteine (C) at a position corresponding to the position 166 of SEQ ID NO: 1 with a serine (S) or a combination thereof.

The present invention also relates to a method of producing the luciferase of the invention or the fusion protein comprising the luciferase of the invention comprising the steps of:

introducing the vector of the invention into a cell under conditions which permit expression of the luciferase and/or growing the cell of invention under conditions that permit expression of the luciferase.

The present invention also relates the use of the luciferase of the invention or of the fusion protein comprising the luciferase of the invention in a luminescence reaction; the use comprising the addition of a substrate for the luciferase.

The present invention provides a method comprising the steps of:

(a) exposing the luciferase or the fusion protein to a substrate and (b) detecting luminescence.

Prior to the exposition, a polynucleotide according to the invention may be introduced into a cell and/or the luciferase or the fusion protein may be expressed.

The method may be in vitro, ex vivo or in vivo.

Fusion Protein

As mentioned in the summary of the invention, the present invention relates to a fusion protein comprising:

an N-terminal domain which comprises an antibody which is a variable domain of a camelid heavy-chain antibody (VHH) or a single chain variable fragment (scFV) directed against an immunoglobulin and a C-terminal domain which comprises a polypeptide with a luciferase activity:

having the amino acid sequence SEQ ID NO: 1 or having at least 80%, at least 85%, at least 90%, at least 95%, at least 96%, at least 97%, at least 98% or at least 99% amino acid sequence identity to the amino acid sequence SEQ ID NO: 1.

In one embodiment the fusion protein comprises an N-terminal domain which comprises a single chain variable fragment (scFV) directed against an immunoglobulin and a C-terminal domain which comprises a polypeptide with a luciferase activity:

having the amino acid sequence SEQ ID NO: 1 or having at least 80%, at least 85%, at least 90%, at least 95%, at least 96%, at least 97%, at least 98% or at least 99% amino acid sequence identity to the amino acid sequence SEQ ID NO: 1.

A single-chain variable fragment (scFv) is a fusion protein of the variable regions of the heavy (VH) and light chains (VL) of immunoglobulins, connected with a linker.

In another embodiment the fusion protein comprises:

an N-terminal domain which comprises a variable domain of a camelid heavy-chain antibody (VHH) directed against an immunoglobulin and a C-terminal domain which comprises a polypeptide with a luciferase activity:

having the amino acid sequence SEQ ID NO: 1 or having at least 80%, at least 85%, at least 90%, at least 95%, at least 96%, at least 97%, at least 98% or at least 99% amino acid sequence identity to the amino acid sequence SEQ ID NO: 1.

VHH are variable domain of a camelid heavy-chain antibody. Indeed, in members of the family Camelidae a significant proportion of serum antibodies are homodimeric IgGs with a molecular weight of about 80 kD (Hamers-Casterman et al. 1993 Nature, 363, 446-448). These heavy chain immunoglobulins (Ig) contain three domains and their variable region is referred to as VHH. Recombinant VHHs (~12-14 kD in size) constitute intact antigen-binding domains and exhibit a broad antigen-binding repertoire. Their hypervariable regions are expanded and exhibit unique characteristics, such as the substitution of three to four hydrophobic framework residues (which interact with the VL in conventional antibodies) by more hydrophilic amino acids. To stabilize the enlarged CDRs, VHHs may possess in addition of the canonical disulfide bond, an extra disulfide bound between CDR1 and CDR3 in dromedaries and CDR2 and CDR3 in llamas (Harmsen and De Haard 2007 Appl Microbiol Biotechnol., 77, 13-22; Muyldermans 2001 J Biotechnol., 74, 277-302). The extended CDR3 loop can adopt a convex conformation, whereas conventional paratopes are limited to concave or flat structures (Muyldermans 2001 J Biotechnol., 74, 277-302). These features allow VHHs to recognize unique epitopes that are poorly immunogenic for conventional antibodies (Lafaye et al. 2009 Mol Immuno., 46, 695-704; Wernery 2001 J Vet Med B Infect Dis Vet Public Health., 48, 561-568). Although VHHs are by definition monovalent antibodies, which by default exclude any avidity effect, their biological activity measured as IC50 in vitro can be similar to conventional, bivalent antibody molecules (Thys et al. 2010 Antiviral Res., 87, 257-264). The VHH may be selected among known VHHs. Examples of known VHHs that can be used according to the invention are disclosed in the table 3 below.

TABLE 3

| Name | Target | SEQ ID NO | Amino acid sequence |
|---|---|---|---|
| sdAb026 | constant Cε3 region of human IgE | SEQ ID NO: 57 | MAEVQLLESGGGLVQPGGSLRLSCAASGFTFGNYDMAWVRQAPGKRPEWVSSIDTGGDITHYADSVKGRFTISRDNAKNTLYLQMNSLRPEDTAVYWCATDEEYALGPNEFDYYGQGTLVTVSSAAALE |
| FC1 | constant fragment region of human IgG1, IgG2, IgG3 and IgG4 | SEQ ID NO: 58 | MQVQLQESGGGLVQPGGSLRLSCAASGGTSIRIGSINALAWYRQALGNQRELVAAVTEGGSTNYADFVKGRFTISRDNAQNMMYLQMNSLKPEDTAVYYCNADKVLYSRGGYYSVANDLWGQGTQVTVSS |

TABLE 3-continued

| Name | Target | SEQ ID NO | Amino acid sequence |
|---|---|---|---|
| FC10 | FC10 recognizes the constant fragment region of human IgG1, IgG2, IgG3 and IgG4 | SEQ ID NO: 59 | MQVQLQESGGGLVQAGDSLRISCRASGLTVNDLYMGWFRQAPGKEREFVGRVTPGDNTDYTYYVDSVKGRFTISRDSAKNTVYLQMNSLKLEDTAVYLCAGRRFGSSEWDYWGQGTQVTVSS |

Therefore, the VHH of the fusion protein according to the invention may have the amino acid sequence selected from the group consisting of SEQ ID NO: 57, SEQ ID NO: 58 and SEQ ID NO: 59.

VHH to be used according the invention may be also selected from a library.

Methods, such as phage display, have been described to select antigen-specific VHH from VHH libraries of immunized camels or llamas. The VHH genes are cloned in phage display vectors, the antigen binders are obtained by panning and selected VHH are expressed in bacteria. The recombinant VHHs have a number of advantages compared with the conventional antibody fragments (Fab or scFv), because only one domain has to be cloned and because these VHHs are well expressed, highly soluble in aqueous environments and are stable at high temperature.

VHH may be also be custom designed, screened from synthetic libraries derivatized from camelid VHH scaffold or from humanized scFv scaffold.

For example, the VHH is obtainable by the method comprising the steps of:

(a) immunizing a camelid, preferably a *Lama pacos*, with the immunoglobulin or a fragment thereof, (b) isolating peripheral lymphocytes of the immunized camelid, obtaining the total RNA and synthesizing the corresponding cDNAs (methods are known in the art; for instance see Lafaye et al. 1995 Res Immunol., 146, 373-82; Erratum in: 1996, Res Immunol., 147, 61), (c) constructing a library of cDNA fragments encoding VHH domains, (d) transcribing the VHH domain-encoding cDNAs obtained in step (c) to mRNA using PCR, converting the mRNA to ribosome display format, and selecting the VHH domain by ribosome display.

The polynucleotide encoding for the VHH and the polynucleotide encoding a polypeptide with a luciferase activity may be inserted in a vector. The polynucleotide encoding for the VHH and the polynucleotide encoding the polypeptide with a luciferase activity are linked so as the fusion protein of the invention to be expressed.

The vector may be then introduced into a cell, for example by transformation of a bacterial cell, so as the cell expresses the fusion protein.

The N-terminal domain and the C-terminal domain of the fusion protein and/or the VHH and the polypeptide with a luciferase activity may be linked via a linker. Preferred linkers have the amino acid sequence selected from the group consisting of GS, AAA, SEQ ID NO: 24, SEQ ID NO: 25 and SEQ ID NO: 26.

The fusion protein may comprise one or more heterologous amino acid sequences at the N-terminus, C-terminus, or both. In particular, it may comprise a tag such as poly-histidine tag for purification purpose.

The present invention also relates to a polynucleotide encoding the fusion protein of the invention as well as to a vector comprising this polynucleotide.

Suitably the fusion protein of the invention or the polynucleotide encoding thereof are recombinant.

Advantageously, the vector comprises the polynucleotide operably linked to a promoter.

Advantageously, the polynucleotide may be codon-optimized for expression of the fusion protein.

The polynucleotide or the vector of the invention may be into a cell.

Therefore, the present invention also relates to a cell comprising the polynucleotide of the invention or the vector of the invention.

The immunoglobulin against which the VHH is directed may be from a human or a non-human animal, preferably a human.

The immunoglobulin may be an IgG1, IgG2, IgG3, IgG4, IgA, IgM, IgD or IgE. Preferably, the immunoglobulin is an IgG, an IgE, an IgM or an IgA. The immunoglobulin of interest will depend on the aim of the assay. For example, when the aim of an assay is to diagnosis an allergy, IgE mainly and IgG secondarily will be preferred. IgM may be used to diagnose a recent infection in blood. IgG may be used to diagnose an older infection in blood. IgA may be used to diagnose infection in blood, mucosa or saliva.

Typically, the immunoglobulin is directed against an antigen.

The antigen may be selected from the group consisting of an allergen, a virus, a bacteria, a fungus and a parasite or a fragment or part thereof.

For example, allergen may be components, mainly proteins, of milk in particular cow's milk, soy, egg, wheat, cod, seafood, shellfish, fishes, nuts, peanut, *D. pteronyssinus, Alternaria*, cat, dog, grass or birch pollen, dust mite, anaesthetics (curare but not limited to), antibiotics (amoxicillin but not limited to), latex, fabrics, venoms (from wasp and bees but not limited to).

Virus may be for example severe acute respiratory syndrome coronavirus 2 (SARS CoV2) or severe acute respiratory syndrome coronavirus 1 (SARS CoV1). Fragment of virus may comprise an isolated protein from the virus, synthesized or expressed as recombinant, such as protein Spike (S) or Nucleoprotein (N) or fragments corresponding to structural or functional domains or fragment of any size.

The immunoglobulin may also be an auto-antibody.

In a preferred embodiment, the VHH is directed against the constant fragment (Fc) of the immunoglobulin.

In one embodiment, the polypeptide with a luciferase activity is a luciferase having the amino acid sequence SEQ ID NO: 1.

The polypeptide with a luciferase activity may have at least 80%, at least 85%, at least 90%, at least 95%, at least 96%, at least 97%, at least 98% or at least 99% amino acid sequence identity to the amino acid sequence SEQ ID NO: 1.

In one embodiment, the polypeptide with a luciferase activity is a mutant luciferase as disclosed above.

Thus, the polypeptide with a luciferase activity may have at least 80%, at least 85%, at least 90%, at least 95%, at least 96%, at least 97%, at least 98% or at least 99% amino acid sequence identity to the amino acid sequence SEQ ID NO: 1 and comprising at least one amino acid substitution selected from the group consisting of:

- substitution of the tyrosine (Y) at a position corresponding to the position 18 of SEQ ID NO: 1 with an arginine (R),
- substitution of the leucine (L) at a position corresponding to the position 48 of SEQ ID NO: 1 with a lysine (K),
- substitution of the isoleucine (I) at a position corresponding to the position 56 of SEQ ID NO: 1 with an alanine (A),
- substitution of the tyrosine (Y) at a position corresponding to the position 116 of SEQ ID NO: 1 with a phenylalanine (F),
- substitution of the tryptophan (W) at a position corresponding to the position 134 of SEQ ID NO: 1 with an amino acid selected from the group consisting of a threonine (T) and glutamate (E),
- substitution of the tryptophan (W) at a position corresponding to the position 163 of SEQ ID NO: 1 with an amino acid selected from the group consisting of a threonine (T) and glutamate (E), and

- substitution of the cysteine (C) at a position corresponding to the position 166 of SEQ ID NO: 1 with a serine (5).

The polypeptide having a luciferase activity may have an amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO 17.

The polypeptide having a luciferase activity may also have the amino acid sequence selected from the group consisting of SEQ ID NO: 42, SEQ ID NO: 43, SEQ ID NO: 44, SEQ ID NO: 45 and SEQ ID NO: 46.

The present invention also relates to a kit comprising:

the fusion protein of the invention and a substrate for the polypeptide with a luciferase activity.

As mentioned above, coelenterazine is the natural substrate for the shrimp Oplophorus luciferase but improvement in signals may be obtained with furimazine.

Consequently, the substrate may be selected from the group consisting of coelenterazine, furimazine or derivatives thereof.

Derivatives of furimazine are disclosed in the patent application WO2018/197727 A1.

Such derivatives of furimazine provide a better bioluminescence signals in term of intensity, signal-to-noise ratio and/or duration.

Consequently, the substrate may be selected in the group consisting in:

8-benzyl-2-((5-methylfuran-2-yl)methyl)-6-phenylimidazo[1,2-a]pyrazin-3(7H)-one 8-benzyl-2-((5-ethylfuran-2-yl)methyl)-6-phenylimidazo[1,2-a]pyrazin-3(7H)-one 8-benzyl-2-((4,5-dimethylfuran-2-yl)methyl)-6-phenylimidazo[1,2-a]pyrazin-3(7H)-one 8-benzyl-6-(2-fluorophenyl)-2-(furan-2-ylmethyl)imidazo[1,2-a]pyrazin-3(7H)-one 8-benzyl-2-(3-methylbenzyl)-6-phenylimidazo[1,2-a]pyrazin-3(7H)-one 8-benzyl-2-(3-methoxybenzyl)-6-phenylimidazo[1,2-a]pyrazin-3(7H)-one 2,8-dibenzyl-6-(2-fluorophenyl)imidazo[1,2-a]pyrazin-3(7H)-one 8-benzyl-6-(2,6-difluorophenyl)-2-(furan-2-ylmethyl)imidazo[1,2-a]pyrazin-3(7H)-one 8-benzyl-6-phenyl-2-((5-(trifluoromethyl)furan-2-yl)methyl)imidazo[1,2-a]pyrazin-3(7H)-one
2,8-dibenzyl-6-(2,6-difluorophenyl)imidazo[1,2-a]pyrazin-3(7H)-one
8-benzyl-6-(2-fluorophenyl)-2-((5-methylfuran-2-yl)methyl)imidazo[1,2-a]pyrazin-3(7H)-one
8-benzyl-2-((5-cyclopropylfuran-2-yl)methyl)-6-phenylimidazo[1,2-a]pyrazin-3(7H)-one
8-benzyl-2-(3-fluorobenzyl)-6-phenylimidazo[1,2-a]pyrazin-3(7H)-one
8-benzyl-2-((5-ethylfuran-2-yl)methyl)-6-(2-fluorophenyl)imidazo[1,2-a]pyrazin-3(7H)-one
8-benzyl-6-(3-fluorophenyl)-2-((5-methylfuran-2-yl)methyl)imidazo[1,2-a]pyrazin-3(7H)-one
8-benzyl-2-(2-fluorobenzyl)-6-phenylimidazo[1,2-a]pyrazin-3(7H)-one
8-benzyl-2-((5-ethylthiophen-2-yl)methyl)-6-phenylimidazo[1,2-a]pyrazin-3(7H)-one
8-benzyl-2-((4,5-dimethylfuran-2-yl)methyl)-6-(2-fluorophenyl)imidazo[1,2-a]pyrazin-3(7H)-one
2-benzyl-8-(2-fluorobenzyl)-6-phenylimidazo[1,2-a]pyrazin-3(7H)-one
2-benzyl-8-(3-fluorobenzyl)-6-phenylimidazo[1,2-a]pyrazin-3(7H)-one
8-(3-fluorobenzyl)-2-(furan-2-ylmethyl)-6-phenylimidazo[1,2-a]pyrazin-3(7H)-one
8-(2-fluorobenzyl)-2-(3-methylbenzyl)-6-phenylimidazo[1,2-a]pyrazin-3(7H)-one
8-(2-fluorobenzyl)-2-(3-methoxybenzyl)-6-phenylimidazo[1,2-a]pyrazin-3(7H)-one
8-(2-fluorobenzyl)-2-(furan-2-ylmethyl)-6-phenylimidazo[1,2-a]pyrazin-3(7H)-one
8-(2-fluorobenzyl)-2-((5-methylfuran-2-yl)methyl)-6-phenylimidazo[1,2-a]pyrazin-3(7H)-one
8-(3-fluorobenzyl)-2-(3-methoxybenzyl)-6-phenylimidazo[1,2-a]pyrazin-3(7H)-one
8-(3-fluorobenzyl)-2-(3-methylbenzyl)-6-phenylimidazo[1,2-a]pyrazin-3(7H)-one
2-((5-ethylfuran-2-yl)methyl)-8-(3-fluorobenzyl)-6-phenylimidazo[1,2-a]pyrazin-3(7H)-one
8-(2-chlorobenzyl)-2-((5-methylfuran-2-yl)methyl)-6-phenylimidazo[1,2-a]pyrazin-3(7H)-one
8-(3-fluorobenzyl)-2-((5-methylfuran-2-yl)methyl)-6-phenylimidazo[1,2-a]pyrazin-3(7H)-one
2-((5-ethylfuran-2-yl)methyl)-8-(2-fluorobenzyl)-6-phenylimidazo[1,2-a]pyrazin-3(7H)-one
8-(3-fluorobenzyl)-6-(2-fluorophenyl)-2-((5-methylfuran-2-yl)methyl)imidazo[1,2-a]pyrazin-3(7H)-one
8-(2,3-difluorobenzyl)-2-(furan-2-ylmethyl)-6-phenylimidazo[1,2-a]pyrazin-3(7H)-one
8-(2,3-difluorobenzyl)-2-((5-methylfuran-2-yl)methyl)-6-phenylimidazo[1,2-a]pyrazin-3(7H)-one
2-benzyl-8-(2,3-difluorobenzyl)-6-phenylimidazo[1,2-a]pyrazin-3(7H)-one
8-(2,6-Difluorobenzyl)-2-((5-methylfuran-2-yl)methyl)-6-phenylimidazo[1,2-a]pyrazin-3(7H)-one
8-(2,3-Difluorobenzyl)-2-((4,5-dimethylfuran-2-yl)methyl)-6-phenylimidazo[1,2-a]pyrazin-3(7H)-one
8-(2,3-Difluorobenzyl)-2-((5-ethylfuran-2-yl)methyl)-6-phenylimidazo[1,2-a]pyrazin-3(7H)-one
8-(2,6-Difluorobenzyl)-2-((5-ethylfuran-2-yl)methyl)-6-phenylimidazo[1,2-a]pyrazin-3(7H)-one
2-((4,5-Dimethylfuran-2-yl)methyl)-8-(2-fluorobenzyl)-6-phenylimidazo[1,2-a]pyrazin-3(7H)-one
2-((4,5-Dimethylfuran-2-yl)methyl)-8-(3-fluorobenzyl)-6-phenylimidazo[1,2-a]pyrazin-3(7H)-one
8-(2,3-difluorobenzyl)-2-((4-ethyl-5-methylfuran-2-yl)methyl)-6-phenylimidazo[1,2-a]pyrazin-3(7H)-one
8-(2,3-difluorobenzyl)-2-((5-ethyl-4-methylfuran-2-yl)methyl)-6-phenylimidazo[1,2-a]pyrazin-3(7H)-one and
8-benzyl-2-(furan-2-ylmethyl)-6-(3-hydroxyphenyl)imidazo[1,2-a]pyrazin-3(7H)-one.

These substrates are respectively disclosed in WO2018/197727 A1 with the following names Q3, Q12, Q16, Q21, Q14, Q18, Q20, Q27, Q28, Q29, Q34, Q36, Q41, Q51, Q54, Q56, Q58, Q61, Q72, Q73, Q81, Q82, Q83, Q84, Q85, Q101, Q100, Q99, Q98, Q97, Q96, Q105, Q107, Q108, Q117, Q121, Q124, Q127, Q129, Q131, Q132, Q135, Q143 and Q149.

In a preferred embodiment, the substrate is 8-(2,3-difluorobenzyl)-2-((5-methylfuran-2-yl)methyl)-6-phenylimidazo[1,2-a]pyrazin-3(7H)-one (Q-108 as disclosed in Table 1 page 129 of WO2018/197727 A1).

The kit may also comprises reagents for the detection of luciferase activity, a control and/or support.

Preferably, the antigen is immobilized on the support. The support may be a slide, a plate, for example a multi-well plate, a strip, for example a strip a nitrocellulose or PVDF membrane or paper, a tube, a disk, a loop, a stick, a propeller, a fibre or an assemblage of fibers.

The present invention also relates to the use of the fusion protein of the invention for detecting and/or quantifying the immunoglobulin in a sample.

The sample may be for example selected from the group consisting of whole blood, serum, plasma, cerebrospinal fluid, sperm, urine, nasopharyngeal smear, oropharyngeal smear, vaginal smear, stool, sweat, saliva, tracheal washing and bronchial washing.

The present invention also relates to a method for detecting the presence of an immunoglobulin in a sample comprising the steps of:

(a) contacting the sample with the fusion protein of the invention,
(b) adding a substrate for the polypeptide with a luciferase activity and
(c) detecting the luminescence.

Typically, the polypeptide with a luciferase activity is the polypeptide with a luciferase activity of the fusion protein of the invention.

Since the level of immunoglobulin in the sample may be also measured by the mean to the emitted luminescence, the present invention also relates to a method for quantifying the level of an immunoglobulin in a sample comprising the steps of:

(a) contacting the sample with the fusion protein of the invention,
(b) adding a substrate for the polypeptide with a luciferase activity and
(c) quantifying the luminescence.

Typically, the polypeptide with a luciferase activity is the polypeptide with a luciferase activity of the fusion protein of the invention.

The methods of the invention may also comprise a step of immobilizing the antigen to a support and/or a step of providing a support where the antigen is immobilized on.

The immobilization may be performed by either by surface adsorption, chemical linkage or non-covalent interaction.

The methods may comprise a step of contacting the sample with the immobilized antigen.

The interaction of the fusion protein with the immunoglobulin may be challenged either by dilution, heating or addition of salt, acid, base, or organic or mineral buffer or any competitor for the interaction, or by lateral flow or acoustic frequency When detecting the luminescence, the number of photons per second may be counted eventually according to their wavelength.

The methods may also comprise a step of comparing to the luminescence emitted to a control.

The present invention also relates to a method for quantifying the level of an immunoglobulin per affinity interval in a sample for evaluating the affinity range of a polyclonal immunoglobulin mixture comprising the steps of:

(a) contacting the sample with an immobilized antigen in the presence of dilution series of the free antigen,
(b) contacting the sample with the fusion protein of the invention and
(c) adding a substrate for the polypeptide with a luciferase activity,
(d) quantifying the luminescence and plot light intensity versus antigen concentration.

Typically, the immunoglobulin of which level is quantified is the immunoglobulin to which the antibody of the fusion protein is directed. The antigen is the antigen to which the immunoglobulin is directed. The polypeptide with a luciferase activity is the polypeptide with a luciferase activity of the fusion protein of the invention.

The invention will be further illustrated by the following figures and examples.

However, these examples and figures should not be interpreted in any way as limiting the scope of the present invention.

FIGURES

Figure 8:
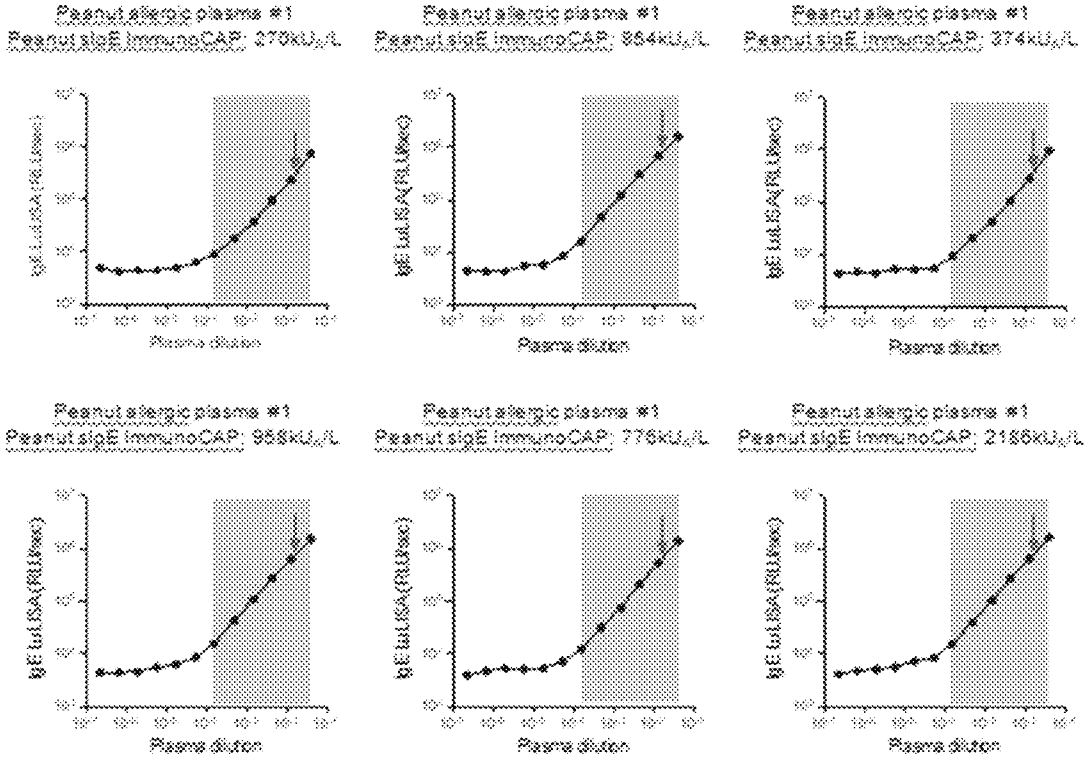

FIG. 8 shows the detection of peanut sIgE by LuLISA using dilution series of plasma from six peanut allergic subjects were diluted in PBS at the indicated concentration and incubated with plate-bound peanut extract. Bioluminescent detection of peanut sIgE levels was performed by LuLISA. Arrows indicate plasma dilution used in FIG. 9. Grey areas show the linear range of detection of the peanut sIgE LuLISA.

Figure 9:
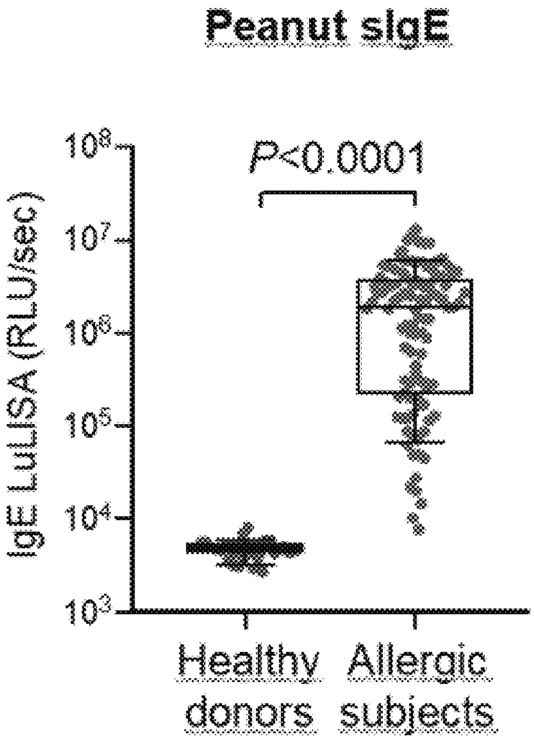

FIG. 9 shows measuring sIgE against total peanut extract using 1 μL of plasma from healthy donors and peanut-allergic subjects.

Figure 10:
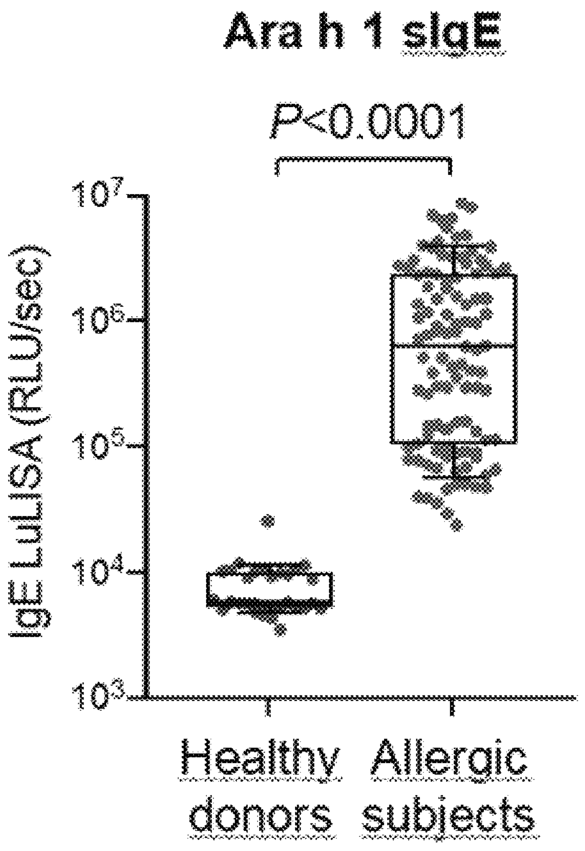

FIG. 10 shows measuring sIgE against the peanut allergen Ara h 1 using 1 μL of plasma from healthy donors and peanut-allergic subjects.

Figure 11:
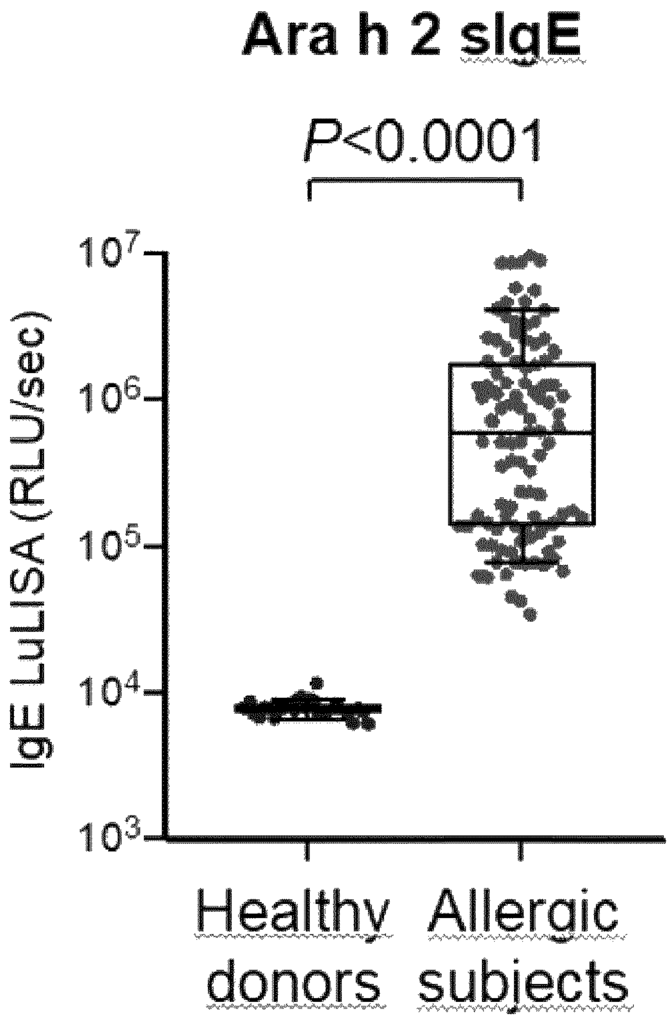

FIG. 11 shows measuring sIgE against the peanut allergens Ara h 2 using 1 μL of plasma from healthy donors and peanut-allergic subjects.

Figure 12:
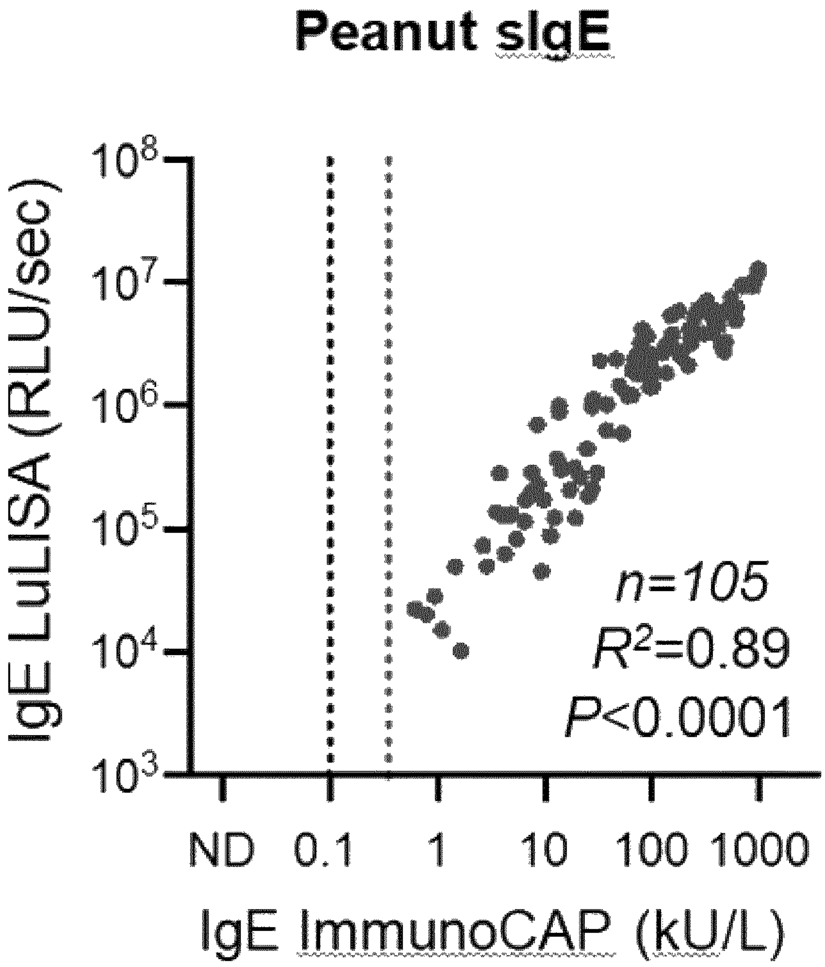

FIG. 12 shows comparison between LuLISA and ImmunoCAP for peanut sIgE in allergic patients.

Figure 13:
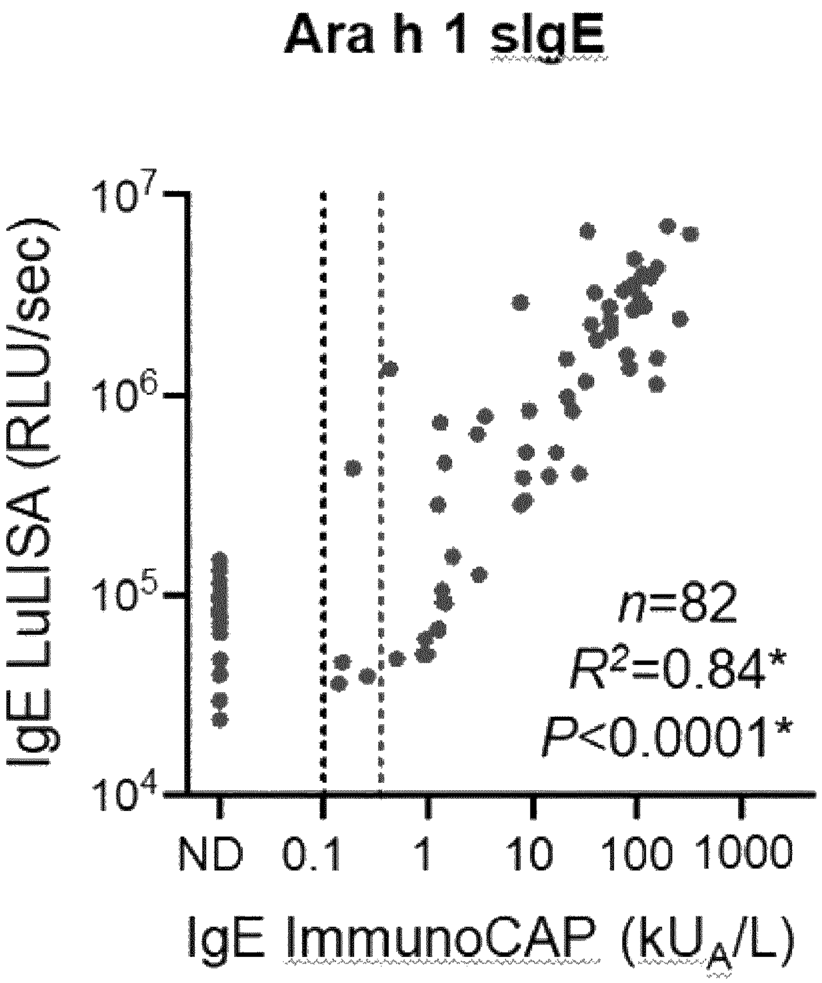

FIG. 13 shows comparison between LuLISA and ImmunoCAP for Ara h 1 sIgE in allergic patients.

Figure 14:
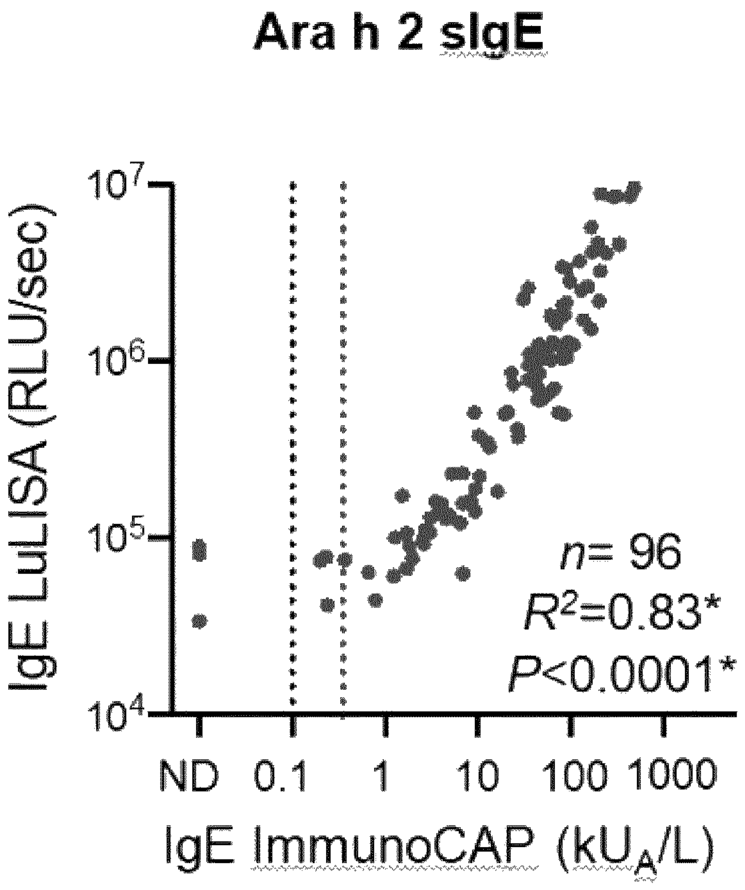

FIG. 14 shows a comparison between LuLISA and ImmunoCAP for Ara h 2 sIgE in allergic patients.

Figure 15:
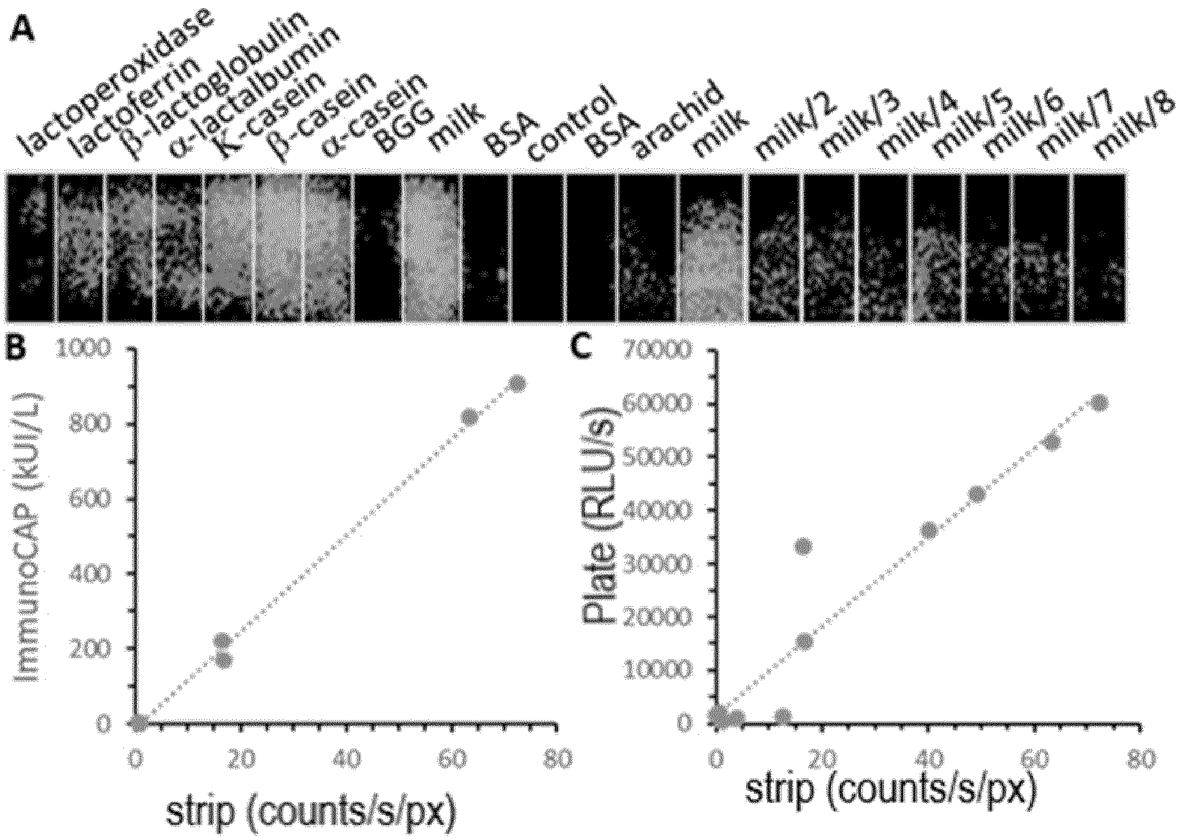

FIG. 15 shows IgE LuLISA on strip (A), a correlation IgE LuLISA on strip vs ImmunoCAP (B), a correlation between IgE LuLISA on strip vs plate (C).

Figure 16:
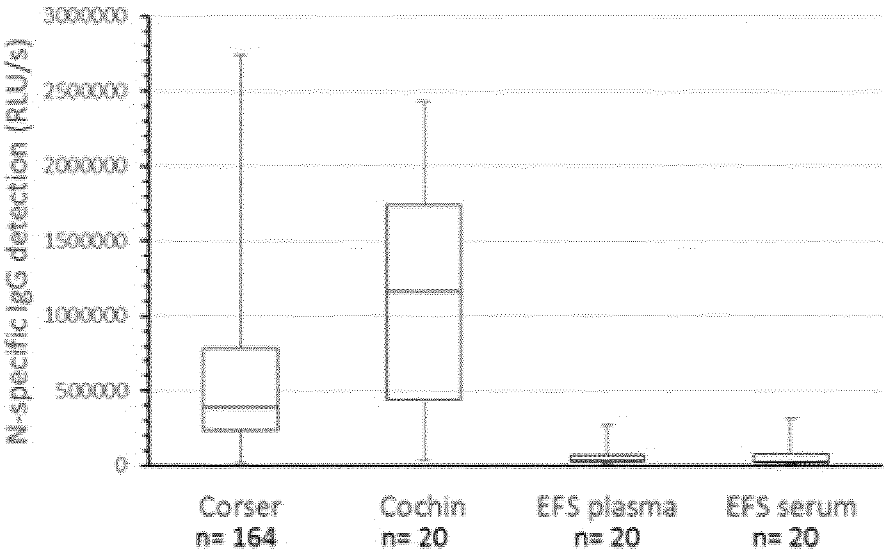

FIG. 16 shows a whisker-plot of LuLISA on IgG specific of protein N of SARS-CoV2 (Whiskers min max; boxes: 2nd and 3rd quartiles separated by a median).

Figure 17:
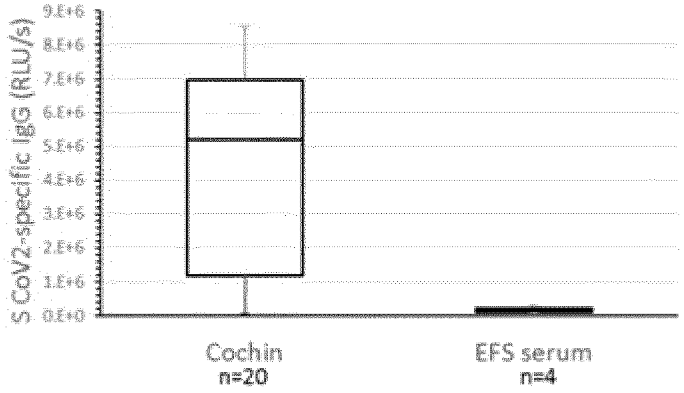

FIG. 17 shows a whisker-plot of LuLISA on IgG specific of protein S of SARS-CoV2.

Figure 18:
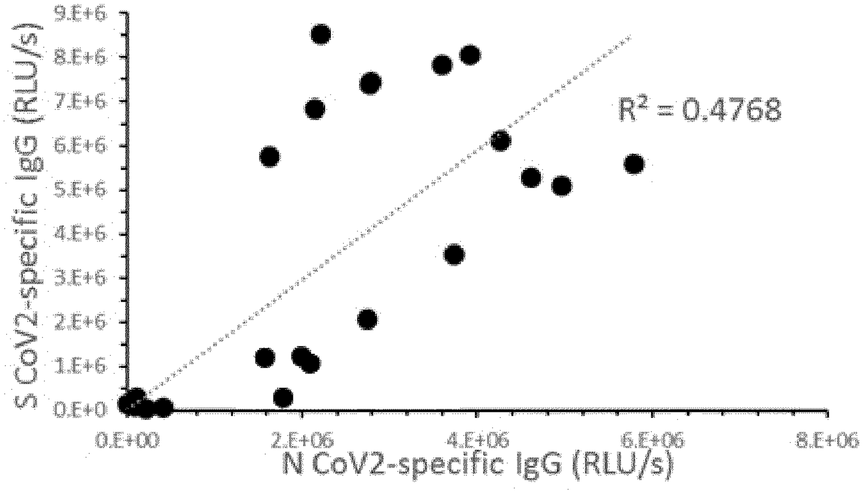

FIG. 18 shows the correlation between the titration of IgG specific of protein N of SARS-CoV2 versus IgG specific of protein S of SARS-CoV2 in serum from APHP-Cochin (n=20) and EFS (n=4).

Figure 19:
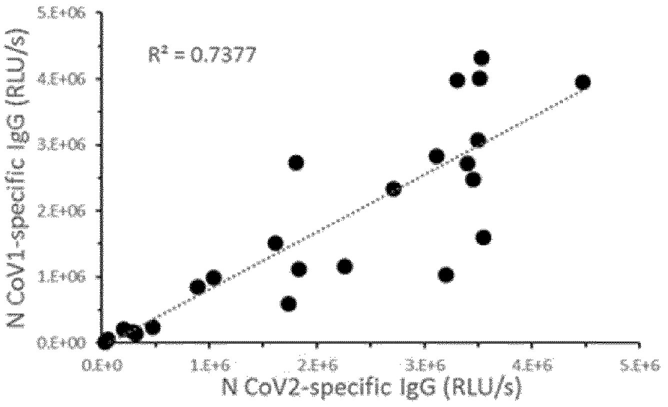

FIG. 19 shows the correlation between the titration of IgG specific of protein N of SARS-COV1 versus IgG specific of protein N of SARS-CoV2 in serum from APHP-Cochin (n=20) and EFS (n=4).

Figure 20:
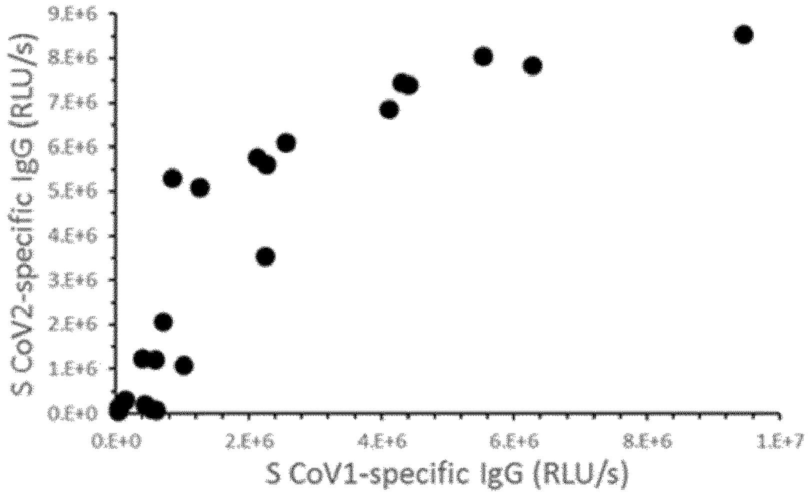

FIG. 20 shows the correlation between the titration of IgG specific of protein S of SARS-CoV1 versus IgG specific of protein S of SARS-CoV2 in serum from APHP-Cochin (n=20) and EFS (n=4).

Figure 21:
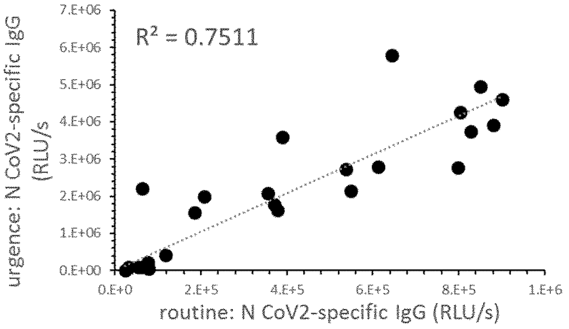

FIG. 21 shows the correlation between the titration of IgG specific of protein N of SARS-CoV2 in the quick test (5 min) versus the routine test (120 min)—mean of the values in duplicate.

Figure 22:
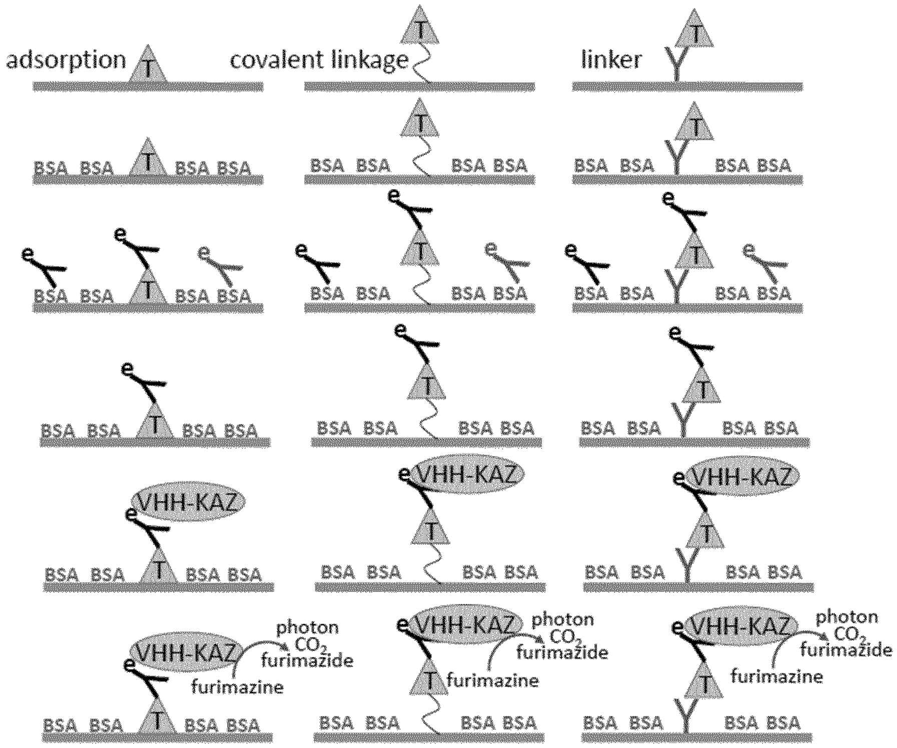

FIG. 22 is a schema of three embodiments of the method of the invention (immobilization of the antigen on the support by adsorption, covalent linkage, non-covalent linkage).

EXAMPLES

Example 1: Mutated Luciferase with Improved Properties

NanoKAZ/nanoLuc results of an intensive mutagenesis for optimizing enzyme production and light intensity with the smallest length from the catalytic domain of the luciferase from Oplophorus *gracilirostris*. However beyond improvement of the catalytic activity of the enzyme, four observations invite finding mutations overcoming 1) enzyme inactivation by reaction products, 2) reaction inhibition by high substrate concentration, 3) low quantum yield of the oxidation reaction, 4) propensity of the enzyme to be adsorbed by material surface (tube, well, membrane . . . ).

Material and Methods:

nanoKAZ (SEQ NO:1) is an optimized sequence of the catalytic domain of the luciferase from Oplophorus *gracilirostris*. (WO2012/061530).

The gene nanoKAZ (SEQ NO:33 [jaz526]) has been synthetized by Eurofins (Germany) with carboxy-end His6-tag and flanking region corresponding to the pET23 sequence (Novagen). PCR purified pET23 vector and the synthetic gene were assembled according to the Gibson method assembling complementary fragments using the NEBuilder HiFi assembly master mix (New England BioLabs). Single or dual mutations have been introduced by PCR in SEQ ID NO: 2 [jaz544], 3 [jaz583], 4 [jaz584], 5 [jaz560], 6 [jaz585], 7 [jaz619]. The gene of SEQ NO:40 [jaz536]) has been synthetized by Eurofins (Germany) with carboxy-end His6-tag and flanking region corresponding to the pET23 sequence (Novagen). Single or dual mutations SEQ NO 41 [jaz570], 42 [jaz572], 43 [jaz573] have been introduced by PCR. in Multiple mutations have been introduced by the Gibson method assembling complementary fragments of the gene carrying specific mutations using NEBuilder HiFi assembly master mix (New-England Biolabs).

Genes SEQ ID NO: 42 [JAZ621] with duplication of SEQ ID NO: 1, SEQ ID NO: 43 [JAZ622] with double substitution of the tyrosine (Y) at a position 116 by a phenylalanine (F) in the duplication of SEQ ID NO: 1, SEQ ID NO: 44 [JAZ476] with triplication of SEQ ID NO: 1, SEQ ID NO: 45 [JAZ620] with triple substitution of the tyrosine (Y) at a position 116 by a phenylalanine (F) in the triplication of SEQ ID NO: 1 and SEQ ID NO: 46 [Scoprii68] substitutions of the tyrosine (Y) at a position 116 by a phenylalanine (F) of Antares sequence encompassing SEQ ID NO: 1 were all synthesized by Eurofins (Germany) with carboxy-end His6-tag and flanking region corresponding to the pET23 sequence (Novagen).

The products (5 mL) were used to transform NEB 5-alpha competent *E. coli* and grown overnight on LB/Agar/ampicillin in Petri dish. Isolated colonies were grown in liquid medium, plasmids were isolated and nucleotide sequence was performed to confirm the presence of the mutations at the correct positions.

Results:

The mutation of the residue tyrosine at position 116 by a phenylalanine (SEQ ID NO: 2 [JAZ544]) increased by 250% the catalytic activity of the nanoKAZ with the furimazine and 1400% with Q108 by reference with nanoKAZ/furimazine. Duplication (SEQ ID NO: 45) or triplication of the mutated catalytic domain (SEQ ID NO: 45) increase the catalytic activity by 2600% and 3500% respectively. Substrate diffusion rate is limiting the 2- or 3-fold expected improvement of the activity of the single domain (1400%). We have shown that luciferase activity is decreasing with time with a rate depending on the substrate nature (Coutant et al 1999). Decreasing activity is fast with Q80 and slow with Q103. Unfortunately, higher is the light emission, fastest is the enzyme inactivation. There is a compromise between light intensity (flash) or long (glow) lifetime. We have shown that decreasing is due to the enzyme inactivation. Mutation of cysteine 166 by a residue serine (SEQ ID NO: 7 [JAZ619]) reduces the rate of inactivation.

Mutation of tryptophan at position 134 by a threonine (SEQ ID NO: 3 [JAZ583]) in the vicinity of the hydrophobic back pocket mildly reduces the inhibition by high concentration of substrate. We counted 1 photon every 1460 molecules of furimazine catalyzed by a molecule of nanoKAZ (SEQ ID NO: 1) at room temperature at furimazine concentration at the maximal reaction rate (54 microM). The choice of substrate modulate this quantum yield from very low to moderate. Lower is the substrate concentration, higher is the quantum yield but unfortunately lower is the reaction rate and lower is the photon emission. Mutation of the residue tyrosine at position 116 by a phenylalanine (SEQ ID NO: 2 [JAZ544]) improves moderately the photon emission count. Mutations of tryptophans at position 134 (SEQ ID NO: 3 [JAZ583]) and 163 (SEQ ID NO: 4 [JAZ584]) pointing out at the protein surface, are the most effective for improving the solubility of the enzyme and reducing surface adsorption affecting assays with higher noise.

Combination of mutations is giving improved properties in terms of light intensity, lifetime, and solubility. Best compromises are selected according to the specific properties required by the application: light intensity/expected sensibility, lifetime/experiment duration, solubility/experimental conditions.

SEQ ID NO: 1 [nanoKAZ, JAZ526] Catalytic activity 100% with furimazine, 250% with Q108.

SEQ ID NO: 2 [JAZ544] substitution of the tyrosine (Y) at position 116 of SEQ ID NO: 1. Catalytic activity 200% of SEQ ID NO: 1 with furimazine, 1450% with Q108.

SEQ ID NO: 3 [JAZ583] substitution of the tryptophan (W) at position position 134 of SEQ ID NO: 1 by a threonine (T). Catalytic activity 100% of SEQ ID NO: 1 with furimazine SEQ ID NO: 4 [JAZ584] substitution of the tryptophan (W) at position 163 of SEQ ID NO: 1 by a threonine (T). Catalytic activity 50% of SEQ ID NO: 1 with furimazine.

SEQ ID NO: 5 [JAZ560] substitution of the isoleucine (I) at position 56 of SEQ ID NO: 1 by an alanine (A). Catalytic activity of 120% SEQ ID NO: 1 with furimazine, 600% with Q108.

SEQ ID NO: 6 [JAZ585] substitutions of the tyrosine (Y) at position 116 by a phenylalanine (F) and the tryptophan (W) at position 134 by a threonine (T) of SEQ ID NO: 1. Catalytic activity 200% of SEQ ID NO: 1 with furimazine, 1400% with Q108.

SEQ ID NO: 7 [JAZ619] substitutions of the tyrosine (Y) at position 116 by a phenylalanine (F) and the cysteine (C) at position 166 by a serine (S) of SEQ ID NO: 1. Catalytic activity 200% of SEQ ID NO: 1 with furimazine.

SEQ ID NO: 8 [JAZ536] substitutions of the tyrosine (Y) at position 18 by an arginine (R), the leucine (L) at position 48 by a lysine (K), the tryptophan (W) at position 134 by a glutamate (E) and the tryptophan 163 (W) at position 163 by a glutamate (R) of SEQ ID NO: 1. Catalytic activity 80% of SEQ ID NO: 1 with furimazine.

SEQ ID NO: 9 [JAZ570] substitutions of the tyrosine (Y) at position 18 by an arginine (R), the leucine (L) at position 48 by a lysine (K), the tryptophan (W) at position 134 by a glutamate (E), the tryptophan 163 (W) at position 163 by a glutamate (E), and the cysteine (C) at position 166 by a serine (S) of SEQ ID NO: 1. Catalytic activity 150% of SEQ ID NO: 1 with furimazine.

SEQ ID NO: 10 [JAZ572] substitutions of the tyrosine (Y) at position 18 by an arginine (R), the leucine (L) at position 48 by a lysine (K), the tryptophan (W) at position 134 by a glutamate (E), the tryptophan 163 (W) at position 163 by a glutamate (E), and the tyrosine (Y) at a position 116 by a phenylalanine (F) of SEQ ID NO: 1. Catalytic activity of 180% SEQ ID NO: 1 with furimazine.

SEQ ID NO: 11 [JAZ573] substitutions of the tyrosine (Y) at position 18 by an arginine (R), the leucine (L) at position 48 by a lysine (K), the tryptophan (W) at position 134 by a glutamate (E), the tryptophan (W) at position 163 by a glutamate (E), the tyrosine (Y) at a position 116 by a phenylalanine (F) and the cysteine (C) at a position 166 by a serine (S) of SEQ ID NO: 1. Catalytic activity 150% of SEQ ID NO: 1 with furimazine.

Several sequences allow an increased signal by duplication or triplication of the catalytic domain. They are mainly used for in vitro or in vivo imaging application requiring light intensity for live imaging, fast kinetics or deep tissue observation. For diagnosis their application in assays are not useful as they increase the signal and the noise. Noticeably diffusion rate of substrate to active site are limiting activity if the substrate concentration is low.

SEQ ID NO: 42 [JAZ621] duplication of SEQ ID NO: 1. Catalytic activity 150% of SEQ ID NO: 1 with furimazine.

SEQ ID NO: 43 [JAZ622] double substitution of the tyrosine (Y) at a position 116 by a phenylalanine (F) in the duplication of SEQ ID NO: 1. Catalytic activity 560% of SEQ ID NO: 1 with furimazine, 2600% with Q108.

SEQ ID NO: 44 [JAZ476] triplication of SEQ ID NO: 1. Catalytic activity 250% of SEQ ID NO: 1 with furimazine.

SEQ ID NO: 45 [JAZ620] triple substitution of the tyrosine (Y) at a position 116 by a phenylalanine (F) in the triplication of SEQ ID NO: 1. Catalytic activity 2500% of SEQ ID NO: 1 with furimazine, 3500% with Q108.

Two color applications with a single substrate but two luciferases as reporter can be performed by using one of sequences from 1 to 15 and the Antares or Scorpii (SEQ NO: 48) which emits redshifted photons through energy resonance transfer from the nanoKAZ to the mOrange derived from Discosoma sp. red fluorescent protein (Shaner Nc, Campbell Re, Steinbach Pa, Giepmans Bng, Palmer Ae, Tsien Ry (2004). Nature Biotechnology, 22(12), 1567-1572).

SEQ ID NO: 46 [Scorpii68] substitutions of the tyrosine (Y) at a position 116 by a phenylalanine (F) of SEQ ID NO: 1 in the Antares chimera (Chu J, Oh Y, Sens A, Ataie N, Dana H, Macklin J J, Laviv T, Welf E S, Dean K M, Zhang F, Kim B B, Tang C T, Hu M, Baird M A, Davidson M W, Kay M A, Fiolka R, Yasuda R, Kim D S, Ng H L, Lin M Z. Nat Biotechnol. 2016 July; 34(7):760-7). Activity is 800% with Q108 but at 562 nm whereas nanoKAZ emits photons at 460 nm. Beyond two colors applications with a single substrate, Scorpii used as reporter is efficient for in vivo imaging with redshifted light going through thicker tissues.

Example 2: Bioluminescent Method for Measuring Allergen-Specific IgE

Materials and Method

Human Plasma

Plasma samples from patients with peanut allergy were obtained as part of their enrolment into an institutional review board—approved clinical trial of oral immunotherapy in children and adults with peanut allergy (peanut oral immunotherapy study: safety, efficacy and discovery; ClinicalTrials.gov Identifier: NCT02103270, US). Peanut allergy was defined as having a reaction to a double-blind, placebo-controlled food challenge to peanut (with reactions elicited with 500 mg of peanut protein) and a positive skin prick test response to peanut (wheal 5 mm). Plasma samples from healthy donors were obtained from the French blood bank (Etablissement Francais du Sang, EFS).

Fusion Protein Anti-IgE sdAb026-nanoKAZ

Design and Synthesis of Plasmid Encoding the Anti-IgE Nanobody-Luciferase Fusion Protein (pET23-sdAb026-Nanokaz)

nanoKAZ is an optimized sequence of the catalytic domain of the luciferase from Oplophorus *gracilirostris* (WO2012/061530).

The gene nanoKAZ has been synthetized by Eurofins (Germany) with carboxy-end His6-tag and flanking region corresponding to the pET23 sequence (Novagen). pET23 plasmid has been amplified with the forward and reverse oligonucleotides (Fwd:5'CTCGAGCACCACCACCACCACCAC3' (SEQ ID NO: 47); Rvr: 5'GGTATATCTCCTTCTTAAAGTTAAAC3' (SEQ ID NO: 48), Eurofins) using a Q5 DNA polymerase, dNTP mix (New England BioLabs). PCR product was purified by electrophoresis on agarose gel (1%, Macherey Nagel). Purified pET23 vector and the synthetic gene were assembly (pET23-nanoKAZ) using NEBuilder HiFi assembly master mix (New England BioLabs).

The sIgE—binding moiety is issued from a humanized heavy chain antibody of alpaca selected against sIgE (single-domain antibody, sdAb026) (Jabs F, Plum M, Laursen N S, Jensen R K, Molgaard B, Miehe M, et al. Trapping IgE in a closed conformation by mimicking CD23 binding prevents and disrupts FcepsilonRI interaction. Nat Commun 2018; 9:7, WO2014/087010 A1). sdAb026 recognizes the constant Cε3 region of human IgE. sdAb026 has an affinity for IgE similar to that of the therapeutic anti-IgE antibody omalizumab (KD 1.4 nM vs. 2.6 nM, respectively3,5), and was reported to inhibit interactions between IgE and the two receptors FcεRI and CD23.

The gene sdab026 has been synthetized by Eurofins with flanking regions corresponding to the pET23-nanoKAZ sequence. Synthetic gene sdab026 has been amplified with the corresponding forward and reverse oligonucleotides (Fwd: 5'ATGGTCTTCACACTCGAAGATTTC3' (SEQ ID NO: 49); Rvr: 5'CATGGTATATCTCCTTCTTAAAGTTAAA3'(SEQ ID NO: 50); Eurofins) using a Q5 DNA polymerase and dNTP mix.

PCR products were purified by electrophoresis on agarose gel. Purified pET23-nanoKAZ vector and the synthetic gene sdAb026 were assembled using NEBuilder HiFi assembly master mix (New-England Biolabs).

The assembled products (5 mL) were used to transform NEB 5-alpha competent *E. coli* and grown overnight on LB/Agar/ampicillin in Petri dish. Isolated colonies were grown in liquid medium, plasmids were isolated and nucleotide sequence was performed to confirm the presence of the sdabs026-nanoKAZ insert.

The full sequence of anti-IgE nanobody luciferase tandem sdAb026-nanoKAZ ([nanobody anti-IgE]-[nanoKAZ]-[His6]) is shown in the table below:

| | |
|---|---|
| Nucleotide sequence of sdAb026-nanoKAZ (SEQ ID NO: 51) sdAb026 in underlined nanoKAZ in bold | ATGGCGGAGGTCCAGTTGCT<br>TGAGAGTGGTGGGGGTCTTG<br>TTCAGCCAGGGGGCTCCCTT<br>CGTCTTAGTTGTGCCGCATC<br>CGGTTTCACATTCGGCAATT<br>ACGACATGGCGTGGGTCCGA<br>CAAGCTCCCGGCAAACGCCC<br>TGAGTGGGTATCGTCTATTG<br>ATACGGGGGGAGATATAACA<br>CACTACGCAGACAGTGTGAA<br>GGGGAGGTTCACAATCTCTC<br>GGGACAACGCAAAGAACACC<br>TTATACTTGCAGATGAATAG |

-continued

| | |
|---|---|
| | CCTGAGACCGGAGGACACTG<br>CTGTGTATTGGTGCGCTACC<br>GATGAAGAATATGCCCTCGG<br>CCCAAACGAATTTGATTATT<br>ACGGACAGGGAACTCTGGTG<br>ACTGTGTCATCAGCTGCCGC<br>CCTGGAG**ATGGTCTTCACAC**<br>**TCGAAGATTTCGTTGGGGAC**<br>**TGGCGACAGACAGCCGGCTA**<br>**CAACCTGGACCAAGTCCTTG**<br>**AACAGGGAGGTGTGTCCAGT**<br>**TTGTTTCAGAATCTCGGGGT**<br>**GTCCGTAACTCCGATCCAAA**<br>**GGATTGTCCTGAGCGGTGAA**<br>**AATGGGCTGAAGATCGACAT**<br>**CCATGTCATCATCCCGTATG**<br>**AAGGTCTGAGCGGCGACCAA**<br>**ATGGGCCAGATCGAAAAAAT**<br>**TTTTAAGGTGGTGTACCCTG**<br>**TGGATGATCATCACTTTAAG**<br>**GTGATCCTGCACTATGGCAC**<br>**ACTGGTAATCGACGGGGTTA**<br>**CGCCGAACATGATCGACTAT**<br>**TTCGGACGGCCGTATGAAGG**<br>**CATCGCCGTGTTCGACGGCA**<br>**AAAAGATCACTGTAACAGGG**<br>**ACCCTGTGGAACGGCAACAA**<br>**AATTATCGACGAGCGCCTGA**<br>**TCAACCCCGACGGCTCCCTG**<br>**CTGTTCCGAGTAACCATCAA**<br>**CGGAGTGACCGGCTGGCGGC**<br>**TGTGCGAACGCATTCTGGCG**<br>**CTCGAG**CACCACCACCACCA<br>CCAC**TGA** |
| Amino acid sequence of sdAb026-nanoKAZ (SEQ ID NO: 52) sdAb026 underlined nanoKAZ in bold | MAEVQLLESGGGLVQPGGSL<br>RLSCAASGFTFGNYDMAWVR<br>QAPGKRPEWVSSIDTGGDIT<br>HYADSVKGRFTISRDNAKNT<br>LYLQMNSLRPEDTAVYWCAT<br>DEEYALGPNEFDYYGQGTLV<br>TVSSAAALE**MVFTLEDFVGD**<br>**WRQTAGYNLDQVLEQGGVSS**<br>**LFQNLGVSVTPIQRIVLSGE**<br>**NGLKIDIHVIIPYEGLSGDQ**<br>**MGQIEKIFKVVYPVDDHHFK**<br>**VILHYGTLVIDGVTPNMIDY**<br>**FGRPYEGIAVFDGKKITVTG**<br>**TLWNGNKIIDERLINPDGSL**<br>**LFRVTINGVTGWRLCERILA**<br>**LE**HHHHHH |

The estimated molecular weight (MW) of sdAb026-nanoKAZ calculated from sequence is 34.1 kD.

Expression, Purification and Validation of Anti-IgE Nanobody-Luciferase Fusion Protein (sdAb026-nanoKAZ)

pET23-sdab026-nanokaz was used to transform *E. coli* BL21 (DE3, New-England Biolabs) to achieve high expression in *E. coli*. Cells were grown at 18° C. and IPTG (Sigma-Aldrich) was added to induce sdAb026-nanoKAZ production. After harvesting the cells by centrifugation (1.5 L), the pellet was resuspended in 50 mM Tris-HCl pH 8.0, 50 mM NaCl with protease inhibitor (Sigma-Aldrich) and lysozyme (0.1 mg/mL, Sigma-Aldrich). Cells were disrupted by freezing-thawing cycle lysis method. DNase I (Sigma-Aldrich) was then added to remove DNA from the sample.

The crude extract was centrifuged 30 min at 1250 g. The supernatant was collected and NaCl (500 mM), Imidazole (20 mM, Sigma-Aldrich) and Triton X-100 (0.1%, Sigma-Aldrich) were added. The cleared lysate was loaded on an equilibrated Hi-Trap 5 mL-column (GE-Healthcare) at 4 mL/min using an AKTA pure chromatography system (GE-Healthcare). The column was washed with 20 volumes of column with a running buffer (50 mM Tris-HCl pH 8.0, NaCl 50 mM, 20 mM imidazole) at 5 mL/min. The sdAb026-nanoKAZ was eluted with a gradient of imidazole from 20 mM to 200 mM in 50 mM Tris-HCl pH 8.0, 50 mM NaCl at 5 mL/min and fractions of 1 mL were collected in 96-deepwell plate (GE-Healthcare). Catalytic activity of fractions was profiled using a luminometer Hydex by diluting 107 fold the fraction in PBS with 27 μM of furimazine. The fractions of high activity were pooled, and loaded on a 1 mL HiTrap Q column (GE-Healthcare) equilibrated in 50 mM Tris-HCl pH 8.0, NaCl 50 mM. The protein was eluted in 50 mM MES pH 6.5, 50 mM NaCl at 1 mL/min at 18° C. using the AKTA pure chromatography system. The fractions of 500 μL were collected in 96-deepwell plate and their activities were assayed as described above. The fractions of high activity were pooled. The quality of the purified protein was assessed by loading an aliquot (10 μL) on a stain-free SDS gel (4-15% Mini-PROTEAN® TGX Stain-Free™ Protein Gels, Bio-Rad).

The gel was activated by UV trans-illumination for 5 min (Bio-Gel Doc XR Imaging System). Tryptophan residues undergo an UV-induced reaction with trihalo compounds and produce a fluorescence signal imaged. An UV-spectrum (240-300 nm) was acquired for evaluating the concentration of sdAb026-nanoKAZ from the solution absorption at 280 nm. The specific activity is about $10^{15}$ acquired photons/second/mg of sdAb026-nanoKAZ with furimazine in PBS at 23° C. The optimal activity is reached for a substrate (furimazine) concentration from 10 to 30 μM (plateau at about 10 times the KM=2 μM). Beyond 30 μM the dipolar moments of the substrates out of the nanoKAZ catalytic site are quenching the photon emission of the catalyzed substrate in the active site. Quenching efficiency depends on dipolar moment of substrates. Substrate catalysis inactivates stochastically the nanoKAZ and the life time of enzyme depends on substrates and catalysis rate. Light emission intensity has been optimized by using optimal conditions according to kinetics parameters according to specific substrates from a thorough enzymatic study of nanoKAZ and its 30 mutants and the catalysis of 172 distinct substrates.

IgE Luciferase Immunosorbent Assay (Lu LISA) Protocol

White 96-well plates with flat bottom (Fluoronunc C96 Maxisorp, Nunc) were coated by adsorption with either 10 μg/mL of peanut extract (F171, Greer laboratories), 10 μg/mL of Ara H1 (NA-AH1-1, Indoor Technology), 10 μg/mL of Ara H2 (RP-AH2-1, Indoor Technology), 5 μg/mL of ovalbumin (OVA, Sigma-Aldrich) or 1 μg/mL of dust mite DER p2 (2B12NA-DP2-1, Indoor Technology) in 50 μL/well of $NaHCO_3$ 50 mM buffer pH 9.5 (Sigma) for 2 hours at room temperature. Target immobilization is the main factor of success or failure of the method as the maximum of target should be immobilized while presenting the allergenic domain accessible to sIgE for binding. Adsorption on Maxisorp® plates favours charge interaction. Alternatives to adsorption are covalent binding of targets through carboxylic, amine or sulfhydryl moieties or glycosylation at the functionalized well surface. Wells were emptied and the coating was saturated with bovine serum albumin (Sigma) at 100 μg/mL in $NaHCO_3$ for 1 hour at room temperature. Wells were washed four times with 100 μL of PBS/Tween 20 0.1%. Recombinant anti-OVA human chimeric IgE (clone X4A4D12/G9/H8, a kind gift from Arkab), anti-dust mite p2 human chimeric IgE (clone CH1, a kind gift from Arkab), or plasma from peanut allergic subjects were diluted in PBS or in a pool of plasma from healthy donors, as indicated. Sample dilutions were incubated 1 hour at room temperature in their respective allergen-coated wells, 50 μL/well. Wells were washed four times with 100 μL PBS/Tween 20 0.1%. Purified sdAb026-nanoKAZ 1 ng/mL ($1\cdot10^9$ $RLU\cdot s^{-1}\cdot mL^{-1}$) in PBS was loaded (50 μL/well) and incubated 30 min at room temperature. Wells were washed four times with 100 μL of PBS/Tween 20 0.1%. Plates can be stored at this step in PBS until measurements. Just before reading, each wells were emptied and loaded with 50 μL of furimazine (8-benzyl-2-(furan ylmethyl)-6-phenylimidazo[1,2-a]pyrazin-3(7H)-one) at 27 μM (about 10 times the KM of nanoKAZ, 2 μM). The plate was orbitally shaked for 5 seconds and the light emission intensity was integrated 1 sec per well using a multi-well plate luminometer (LB960 Centro, Berthold).

For processing an affinity spectra from LuLISA competition assay, mixtures of the same concentration of serum or plasma sample, 0.5 μL in 50 μL, with 3 by 3 dilution series of the free allergen from 10 μM to 0.7 μM in PBS along 16 allergen-coated wells of a 384-well plate or with 10 by 10 dilution series of the free allergen from 10 μM to 1 μM along 8 allergen-coated wells of a 96-well plate. Values should be adapted to IgE affinities. 1 to 3 hours of incubation for reaching equilibrium or at the nearest. Wells were washed four times with 100 μL PBS/Tween 20 0.1%. Purified sdAb026-JAZ572 (1 ng/mL) is preferred to sdAb026-nanoKAZ for higher signal and lower background especially for high concentration of free allergen while IgE binding to immobilized allergen is low in so long incubation time. Eventually Tween 20 0.1%, BSA 0.1 mg/mL, or gelatine 0.1 mg/mL might be used for reducing background. Milk should be avoided for IgE assays in potentially allergic patients. Wells were washed four times with 100 μL PBS/Tween 20 0.1%. Just before reading, each wells were emptied and loaded with 50 μL of hikazine-108 (8-benzyl-2-(furan-2-ylmethyl)-6-phenylimidazo[1,2-a]pyrazin-3(7H)-one) at 13.5 μM. The plate was orbitally shaked for 1 seconds and the light emission intensity was integrated 0.5 sec per well using a multi-well plate luminometer (LB960 Centro, Berthold). Bioluminescence intensity is displayed versus target concentration as a bar graph.

IgE Immunocap

ImmunoCAP analysis was performed on shipped samples by Phadia, Thermo Fisher.

IgE ELISA Protocol

Clear, flat bottom 96- or 384-well plates (Maxisorp, Nunc) were coated as described above, 2 hours at room temperature. Wells were emptied and the coating was saturated with 50 μL of bovine serum albumin (Sigma) at 100 μg/mL in PBS for 1 hour at room temperature. Wells were washed four times with 100 μL of PBS/Tween 20 0.1% (Sigma). Recombinant anti-OVA human chimeric IgE (clone X4A4D12/G9/H8, a kind gift from Arkab), anti-dust mite p2 human chimeric IgE (clone CH1, a kind gift from Arkab), or plasma from peanut allergic subjects were diluted in PBS and incubated 1 hour at room temperature in their respective allergen-coated wells, 50 mL/well. Wells were washed four times with 100 μL of PBS/Tween 20 0.1%. 50 μL of goat IgG anti-human IgE conjugated with alkaline phosphatase diluted (1:700 in PBS, Sigma-Aldrich) were loaded in each well and incubated 1 hour at room temperature. Wells were washed four times with 100 μL of PBS/Tween 20 0.1%. All wells were emptied, 50 μL of phosphatase substrate pNPP 1 mg/mL (4-Nitrophenyl phosphate disodium salt, Sigma-Aldrich) were added per well, incubated 3 hours at room temperature or overnight at 4° C. Absorbance was measured at 405 nm with a multi-well plate spectrophotometer (Saphire, Tecan) and compared with LuLISA results.

Statistical Analysis

Differences in IgE levels between plasma samples from healthy donors and peanut allergic subjects were compared using an unpaired Mann-Whitney U test. P values <0.05 are considered statistically significant.

Blood Samples from Fingertip

Tests have been performed with a healthy volunteer to set up a project application for blood sampling from a reduced cohort of allergic patients at the Trousseau Hospital for an IgE LuLISA assay in parallel with ImmunoCAP and ELISA.

The tests have been performed after decontamination of the fingertip with alcohol using a lancing device with sterile disposable lancets usually performed for glucose assay for diabetic patient auto-survey. One μL is pipetted and mixed to 50 μL of a solution of PBS, BSA (50 μg/mL), heparin (10 UI/mL), sdAb026-nanoKAZ (1 ng) preloaded inside a 1000 μL tip (single use) ended by a paper filter framed by to polyethylene filter plugs. The diluted blood is filtered through the tip end and loaded in a 96-well plate pre-coated with the specific allergen and incubated at room temperature for 5 min. The well is washed with PBS and 100 μL of luciferase substrate (furimazine analogs) is added and bioluminescence is immediately measured during 1 second using a plate-luminometer (LB960 centro, Berthold). Measurements are performed in parallel with negative and positive controls for internal calibration.

Results

Sensitive and Specific Detection of Allergen-Specific IgE by Luciferase-Linked Immunosorbent Assay (LuLISA)

To establish a proof-of-concept for the specific detection of sIgE using LuLISA, dilution series in PBS of recombinant IgE, IgG1 (the major IgG subclass) or IgG4 (the main IgG subclass overproduced during allergen-specific immunotherapy) directed against the house dust mite allergen Der p 2 were prepared. The 3 groups of samples were analyzed using IgE LuLISA.

Figure 1:
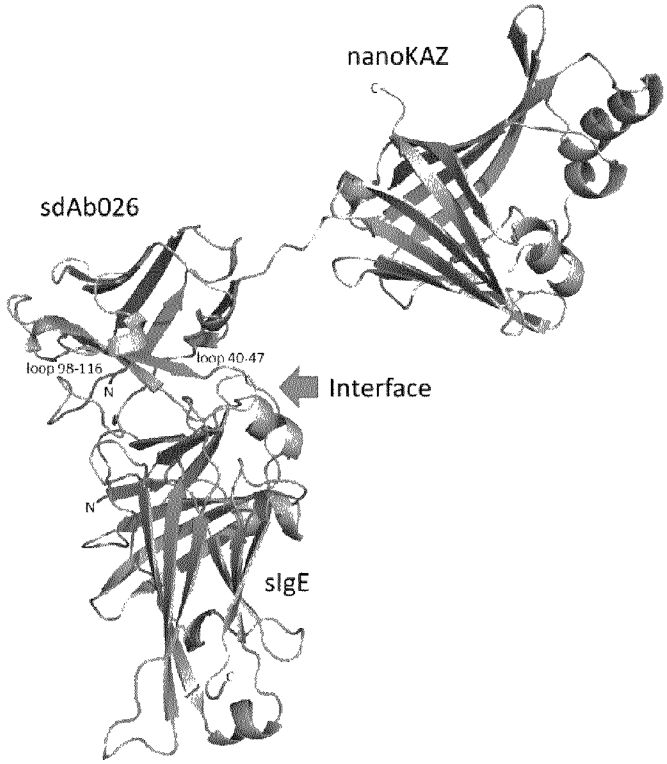
FIG. 1 is a cartoon representation showing the anti-IgE nanobody-luciferase tandem (sdAb026-nanoKAZ) bound to the Fc portion of IgE.
Figure 2:
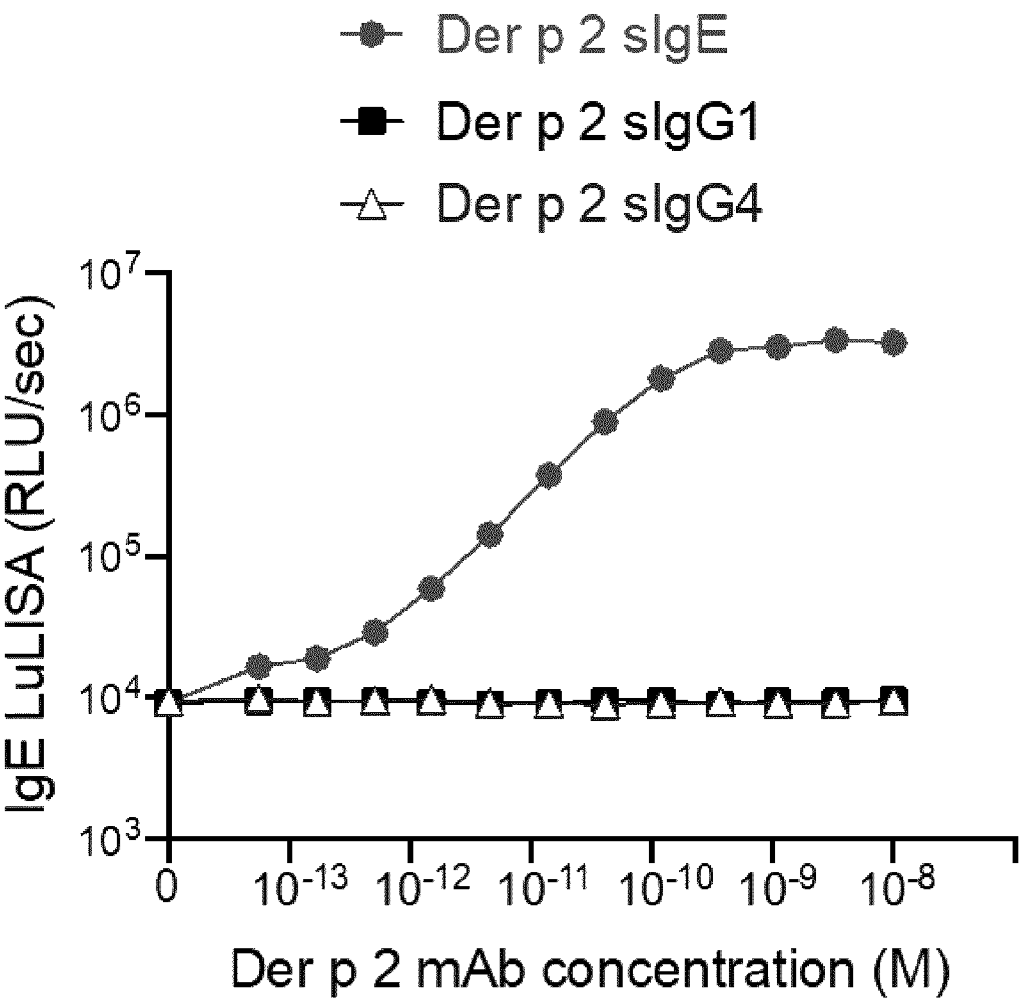
FIG. 2 shows an analysis using IgE LuLISA of dilution series in PBS of recombinant IgE, IgG1 or IgG4 directed against the house dust mite allergen Der p 2. RLU: relative light unit.

As expected, a concentration-dependent signal arose only for the sample containing anti-Der p 2 sIgE, with a detection limit of $\sim5\times10^{-13}$ M sIgE (~1 pg/mL; ~0.0004 kUA/L) (FIG. 2).

A similar experiment was performed on recombinant human anti-ovalbumin IgE. Recombinant human anti-ovalbumin (OVA) IgE were diluted in PBS at the indicated concentration and incubated with plate-bound OVA. Bioluminescent detection of antibody levels was performed by LuLISA using the anti-IgE sdAb026-nanoKAZ.

Figure 3:
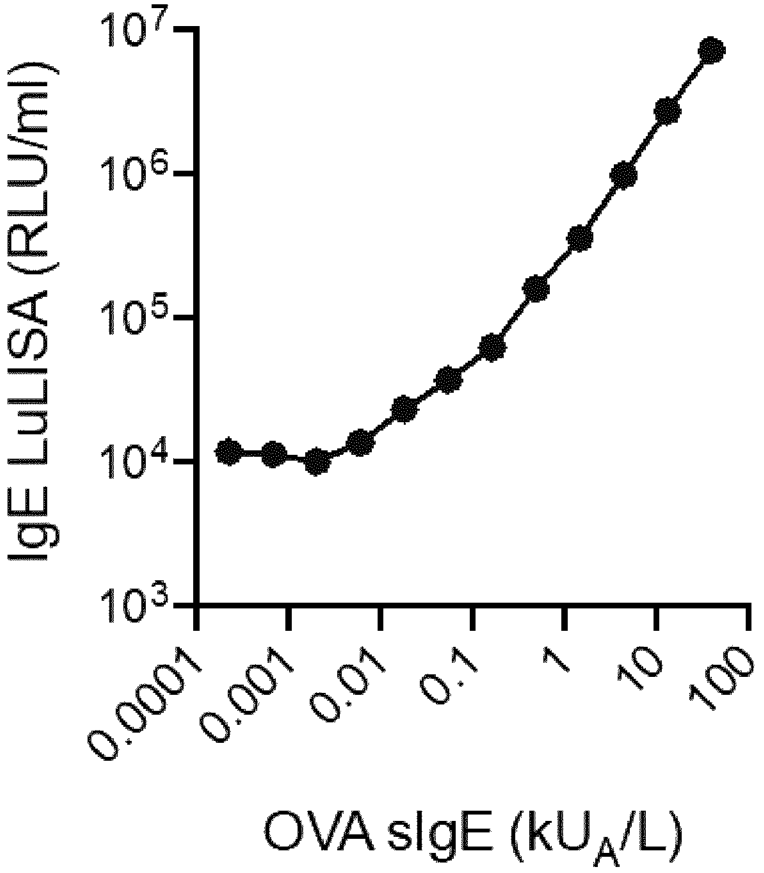
FIG. 3 shows an analysis using IgE LuLISA of dilution series in PBS of recombinant human anti-ovalbumin (OVA) IgE.
Figure 4:
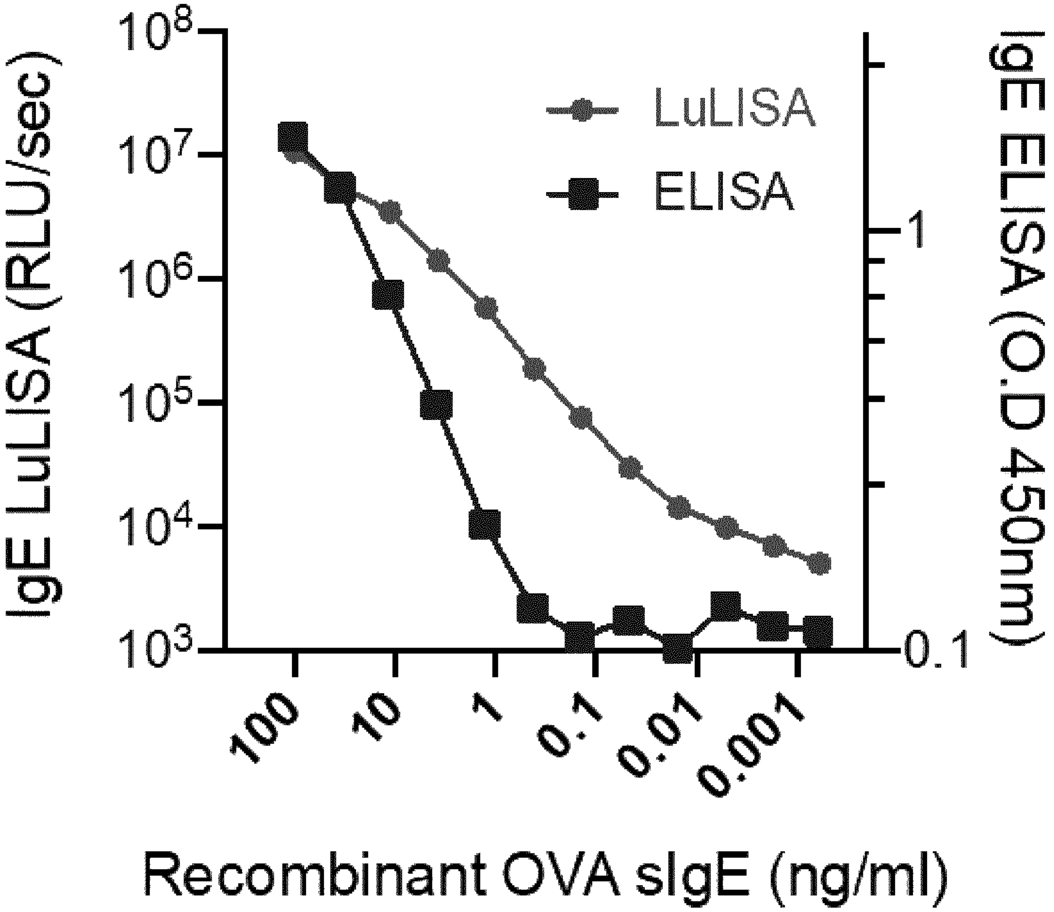
FIG. 4 shows a comparison of sensitivity between IgE LuLISA and IgE ELISA using recombinant anti-ovalbumin (OVA) IgE.

It was also obtained high sensitivity with recombinant anti-ovalbumin (OVA) IgE, which was detectable by LuLISA at concentrations as low as 5 pg/mL (0.002 kUA/L) (FIGS. 3 and 4).

Recombinant anti-ovalbumin (OVA) IgE was diluted in PBS at the indicated concentrations. Levels of OVA sIgE were assessed in aliquots from the same dilution sample using LuLISA or ELISA. The sensitivity of LuLISA was also much higher than that of standard ELISA for the detection of sIgE (FIG. 4).

Figure 5:
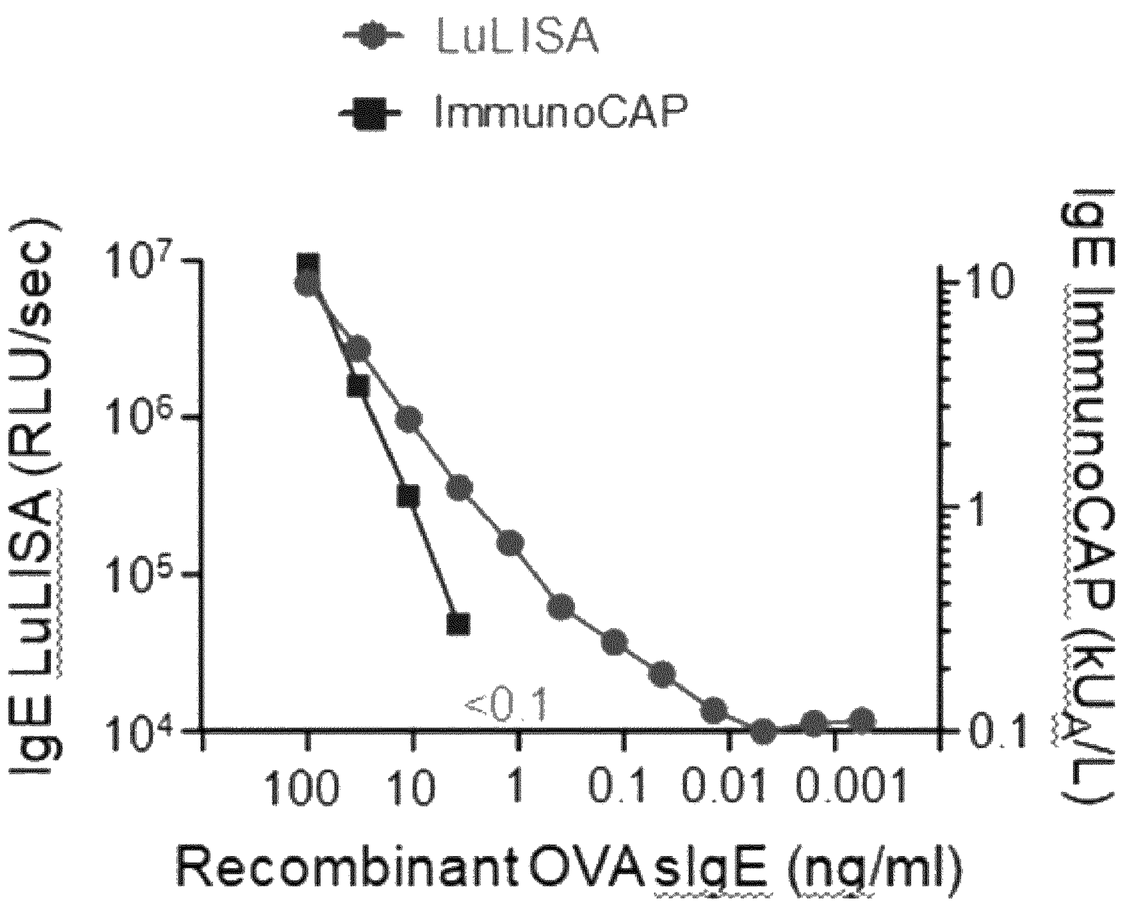
FIG. 5 shows a comparison of the dynamic range and sensitivity of IgE LuLISA versus standard ImmunoCAP, using recombinant OVA sIgE.

Next, it was compared the dynamic range and sensitivity of IgE LuLISA versus standard ImmunoCAP, using recombinant OVA sIgE diluted in plasma pooled from 30 healthy donors (FIG. 5). This head-to-head comparison revealed a markedly increased (~250-fold) analytical sensitivity of LuLISA compared with ImmunoCAP (FIG. 5).

Figure 6:
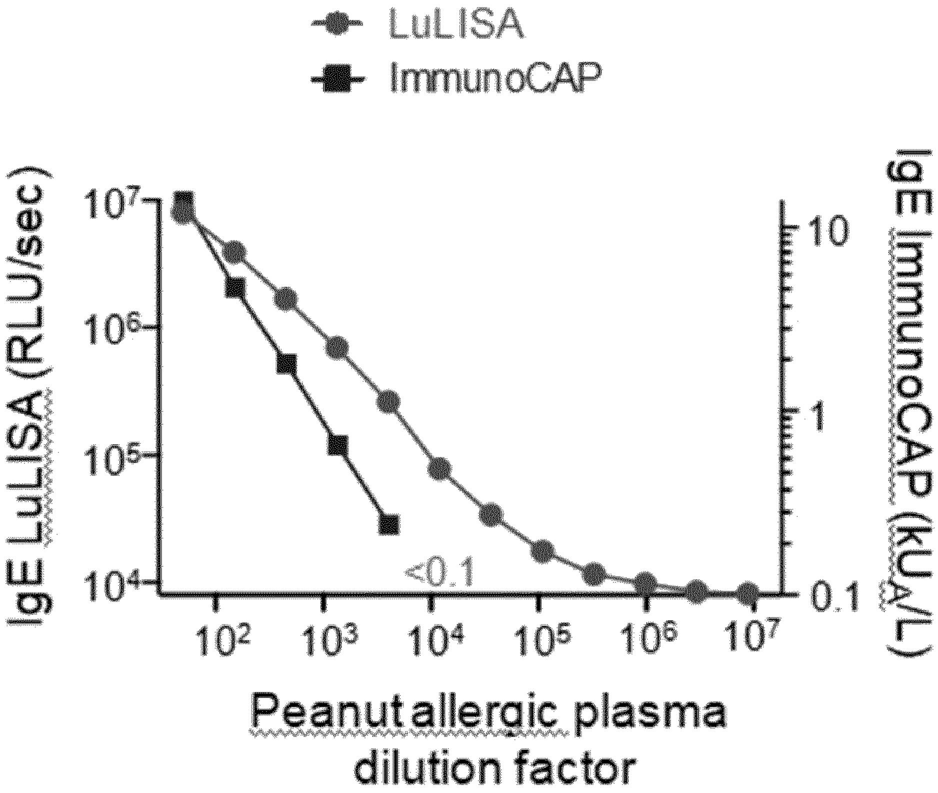
FIG. 6 shows a comparison of the dynamic range and sensitivity of IgE LuLISA versus standard ImmunoCAP, using plasma sample from a highly peanut allergic subject.

It was performed similar experiments with dilution series of a plasma sample from a highly peanut allergic subject, which was again diluted in a pool of plasma from 30 healthy donors (FIG. 6). ImmunoCAP allowed detection of peanut sIgE in plasma diluted up to 4,050 times, while peanut sIgE was still detected by LuLISA in allergic plasma diluted 100,000 to 300,000 times (FIG. 6).

Figure 7:
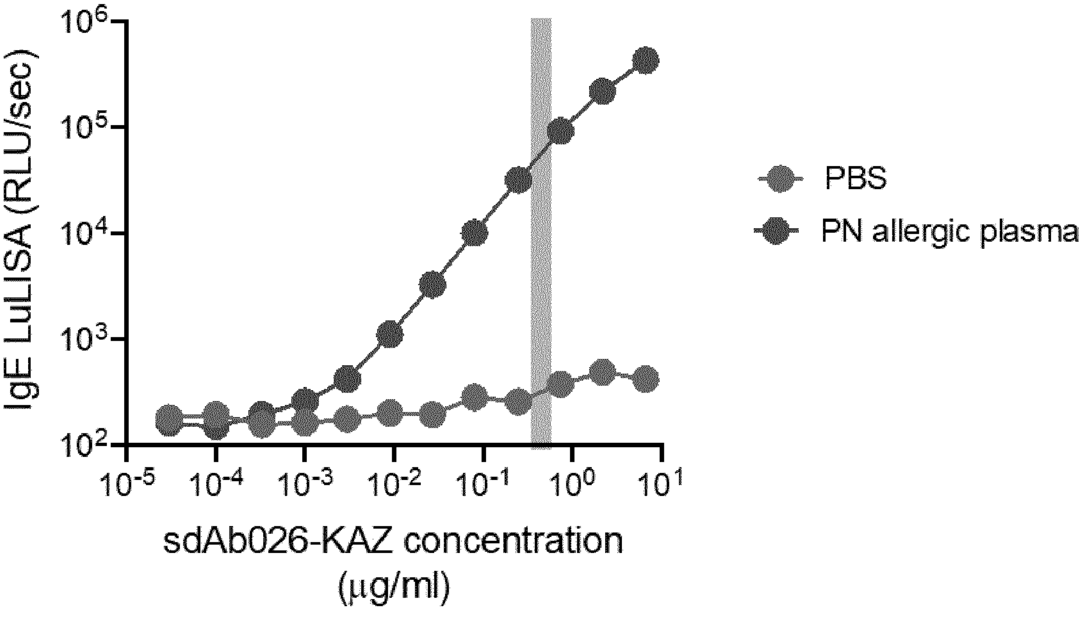
FIG. 7 shows the influence of the concentration of the anti-IgE nanobody-luciferase fusion protein on bioluminescent detection of IgE by LuLISA. Area in grey shows values obtained at the sdAb026-nanoKAZ concentration used for all other experiments in this study.

It was then studied the influence of the concentration of the anti-IgE nanobody-luciferase fusion protein on bioluminescent detection of IgE by Lu LISA. 1 μL of plasma from a peanut allergic subjects (peanut-specific IgE ImmunoCAP values: 2186 kU/L) was diluted in 50 μL of PBS and incubated with plate-bound peanut extract (PBS alone was used as a control). Bioluminescent detection of peanut-specific IgE levels was performed by LuLISA at the indicated concentration of anti-IgE nanobody-luciferase tandem (sdAb026-nanoKAZ). Dilution series of the anti-IgE nanobody-luciferase fusion protein gave a concentration-dependent signal at a fixed (1:50) dilution of this peanut allergic plasma sample, and confirmed the very low bioluminescent background signal of the IgE LuLISA (FIG. 7).

Head-to-head comparison between LuLISA and ImmunoCAP in allergic patients showed a high correlation between both methods ($R^2$=0.89, 0.84 and 0.83 for peanut sIgE, Ara h 1 sIgE and Ara h 2 sIgE, respectively) (FIGS. 12, 13 and 14). These correlations were calculated using all plasma samples for which sIgE levels were above the detection cut-off of ImmunoCAP (0.1 kUA/L). This was the case for all samples for peanut sIgE. However, 17 out of 82 samples (19.7%) for Ara h 1 sIgE and 3 out of 96 samples (3.1%) for Ara h 2 sIgE were below the detection limit of ImmunoCAP (FIGS. 12, 13 and 14). However, all these subjects had clear clinical reactivity to peanut, as assessed by performing double-blind, placebo-controlled food challenge (DBPCFC) and skin prick tests (Table 4).

TABLE 4

| Patient's ID | Peanut DBCFC cumulated tolerated dose (mg) | Skin prick test peanut wheal diameter (mm) | ImmunoCAP Total IgE (IUA/L) | ImmunoCAP peanut specific IgE (IUA/L) | ImmunoCAP Ara h 1 sIgE (IUA/L) | ImmunoCAP Ara h 2 sIgE (IUA/L) |
|---|---|---|---|---|---|---|
| P003 | 75 | 7.5 | 985 | 4.27 | <0.1 | 2.72 |
| P004 | 175 | 15.5 | 470 | 3.82 | <0.1 | 3.63 |
| P006 | 375 | 19 | 243 | 7.67 | <0.1 | 5.25 |
| P013 | 275 | 8.5 | 274 | 30.4 | <0.1 | 0.37 |
| P025 | 75 | 20 | 410 | 4.18 | <0.1 | 3.03 |
| P030 | 275 | 8.5 | 35 | 6.49 | <0.1 | 3.54 |
| P033 | 375 | 4 | 550 | 1.65 | <0.1 | <0.1 |
| P055 | 25 | 11 | 333 | 3.58 | <0.1 | 1.54 |
| P059 | 5 | 16.5 | 449 | 1.46 | <0.1 | 1.29 |
| P060 | 75 | 8 | 240 | 0.41 | <0.1 | 0.2 |
| P067 | 5 | 10.5 | 73 | 0.79 | 0.5 | <0.1 |
| P070 | 5 | 19.5 | 443 | 13.6 | <0.1 | 10.3 |
| P085 | 25 | 12 | 316 | 2.89 | <0.1 | 1.71 |
| P097 | 5 | 14.5 | 281 | 5.43 | <0.1 | 1.72 |
| P102 | 5 | 5 | 87 | 0.62 | <0.1 | <0.1 |
| P103 | 5 | 17.5 | 102 | 0.95 | <0.1 | 0.79 |
| P109 | 0 | 6 | 242 | 25 | <0.1 | 0.24 |
| P111 | 0 | 23 | 1529 | 1.1 | <0.1 | 1.25 |

Altogether, these results indicate that the IgE LuLISA has a very high sensitivity and specificity, and could thus potentially be used to quantify IgE in samples from patients with very low sIgE. The main advantage of the IgE LuLISA over ImmunoCAP is that it requires extremely low volume of sample. In the case of the sample from the peanut-allergic patient used in FIG. 6, peanut sIgE could still be detected using less than 1 nanoliter of the initial patient's sample. Thus, very large screens of sIgE against arrays of potential allergens can be envisioned using IgE LuLISA, even when patient's sample sizes are limited.

It was then sought to further validate this approach by measuring sIgE against total peanut extract, or against the major peanut allergens Ara h 1 and Ara h 2 using 1 μL of plasma from 31 healthy donors (obtained from the French blood bank EFS with unknown allergic status) and 82-105 peanut-allergic subjects (collected upon their enrolment into the institutional review board—approved peanut oral immunotherapy study: safety, efficacy and discovery trial; ClinicalTrials.gov identifier: NCT02103270). Dilution series from reference samples with titrated high peanut sIgE were used for assay calibration, to ensure that all plasma samples were analysed within the linear range of detection of our method (FIG. 8).

As expected, significantly higher levels of peanut sIgE, Ara h 1 sIgE and Ara h 2 sIgE were detected in plasma samples from peanut allergic subjects as compared to healthy donors (FIGS. 9, 10 and 11).

Altogether, these results demonstrate that the IgE LuLISA is highly sensitive and accurate for the clinical detection of sIgE, and requires very low volumes of plasma. Besides ImmunoCAP, several other methods have been reported for the detection of sIgE, including IMMULITE and, more recently, isotype-specific agglutination-PCR (ISAP) (Hamilton R G et al. 2008, Tsai C T et al., 2018). IMMULITE appears to be the closest method to LuLISA as it uses a chemiluminescent approach to detect sIgE. However, the reported detection limit for sIgE with IMMULITE is the same as for ImmunoCAP (0.1 kUA/L). Similarly to LuLISA, detection of sIgE by ISAP can be performed using 1 μl of clinical sample. However, the two tests are based on different approaches as ISAP requires chemically-synthesized allergen-DNA (for each type of allergen) and secondary anti-IgE antibody-DNA conjugate for the detection of sIgE by quantitative PCR.

IgE LuLISA was used in a strip test (lateral flow) for a serum IgE testing on baby allergic to milk. Result is shown in FIG. 15.

Such test aims proofing the application of LuLISA in emergency conditions for detecting IgE specific for curare (anaesthetics), amoxicillin (antibiotics) and latex (gloves) in patients attending surgery or for detection of allergy to milk compounds in new born babies in paediatric emergency.

The blood sampling from fingertip is adapted for a sIgE LuLISA of patients treated by omaluzimab in a routinely and timely manner for adjusting the injected doses with the amount of the detected free sIgE.

The low amount of sample required and the extended performance of LuLISA versus ELISA allow extended application as the plotting of affinity profile or spectra for serum with potentially more than one molecular species of IgE. LuLISA competition is performed using a series of allergen dilution mixed with a constant concentration of serum. IgE detected amount is correlated to light intensity. IgE detected amount per allergen concentration interval is a way to evaluate the presence of very high (sub-picomolar), high (nanomolar), medium (10 to 100's nanomolar) or low (micromolar and beyond) affinity immunoglobulin for the allergen. Higher affinity, stronger saturation and aggregation of IgE receptors at the surface of mastocytes, basophiles and macrophages, higher histaminic and cytokinic response with higher risk of anaphylactic shock. Affinity spectra are a relevant tool for the follow up of patient under desensibilizing treatment for orienting the therapeutic strategy from stopping the challenge with increasing amounts of allergen, controlling the short term response with anti-histaminic or clearing the high affinity IgE with competitor of the IgG Fc receptor binding site (Omaluzimab).

In summary, the IgE LuLISA is a new method for the detection of sIgE of ultra-high sensitivity requiring only very small (1 μL or less) plasma sample volumes. The use of bioluminescence offers markedly increased sensitivity over classical colorimetric (ELISA) or fluorescent (ImmunoCAP) IgE detection methods with an extended dynamic range of concentration. The method is fully automatable and uses commercialized plates and a standard luminometer for the bioluminescent detection of IgE. Thus, IgE LuLISA should be very cost-effective over conventional ImmunoCAP.

Example 3: Luciferase Immuno-Absorbent Assay for SARS COv-2 Serology

Material and Methods:

Human Plasmas and Serums

The samples were obtained from serums of the CORSER cohort (n=164; IcareB), from serums of the observation and monitoring protocol of the Intensive Medicine and Resuscitation service of Assistance Publique des Hopitaux de Paris (APHP) Cochin (n=20) in longitudinal follow-up and from healthy donors of Etablissement Français du Sang (EFS) sampled in December 2019 (frozen plasmas n=20, frozen serums n=20). Prepandemic frozen sera from 664 healthy donors were obtained from the French blood bank (Etablissement Français du Sang, EFS).

Fusion Protein Anti-IgG Nanobody-Luciferase

Design and Synthesis of Plasmid Encoding the Anti-IgG Nanobody-Luciferase Fusion Protein (pET23-Fc1-nanoKAZ or pET23-Fc10-nanoKAZ, with Fc1 Coding for SEQ ID NO: 62 and Fc10 Coding for SEQ ID NO: 63 and Jaz572 for SEQ ID NO: 10 Respectively or pET23-Fc1-Jaz572 or pET23-Fc10-Jaz572, with Fc1 Coding for SEQ ID NO: 62 and Fc10 Coding for SEQ ID NO: 63 and Jaz572 for SEQ ID NO: 10 Respectively)

nanoKAZ is an optimized sequence of the catalytic domain of the luciferase from Oplophorus *gracilirostris* (WO2012/061530). Jaz572 (SEQ ID NO: 10 is derived from the nanoKAZ with an improved catalytic activity increasing photo emission and signal and a reduced aggregation and surface adsorption behavior reducing noise contributing for a better signal noise ratio.

The gene nanoKAZ and JAZ572 have been synthetized by Eurofins (Germany) with carboxy-end His6-tag and flanking region corresponding to the pET23 sequence (Novagen). pET23 plasmid has been amplified with the forward and reverse oligonucleotides (Fwd: 5'CTCGAGCACCACCACCACCACCAC3' (SEQ ID NO:47); Rvr:5'GGTATATCTCCTTCTTAAAGTTAAAC3' (SEQ ID NO: 48), Eurofins) using a Q5 DNA polymerase, dNTP mix (New England BioLabs). PCR product was purified by electrophoresis on agarose gel (1%, Macherey Nagel). Purified pET23 vector and the synthetic gene were assembly (pET23-nanoKAZ or pET23-jaz572) using NEBuilder HiFi assembly master mix (New England BioLabs).

The IgG-binding moiety is issued from a humanized heavy chain antibody of alpaca selected against IgG (single-domain antibody) (U.S. Pat. No. 10,259,886 B2). FC1 recognizes the constant fragment region of human IgG1, IgG2, IgG3 and IgG4 with the following dissociation constants at equilibrium: KD 0.57 nM, 1.73 nM, 47.8 nM, 0.30 nM respectively with a KD for all IgG of 3.25 nM (U.S. Pat. No. 10,259,886 B2). FC10 recognizes the constant fragment region of human IgG1, IgG2, IgG3 and IgG4 with the following dissociation constants at equilibrium: KD 2.62 nM, 7.29 nM, 8.99 nM, 12.3 nM respectively with a KD for all IgG of 3.25 nM (U.S. Pat. No. 10,259,886 B2).

The gene fc1 and fc10 has been synthetized by Eurofins with flanking regions corresponding to the pET23-nanoKAZ sequence. Synthetic gene fc1 or fc10 have been amplified with the corresponding forward and reverse oligonucleotides using a Q5 DNA polymerase and dNTP mix.

PCR products were purified by electrophoresis on agarose gel. Purified pET23-nanoKAZ and pET23-jaz572 vectors and the synthetic gene fc1 or fc10 were assembled using NEBuilder HiFi assembly master mix (New-England Biolabs).

The assembled products (5 mL) were used to transform NEB 5-alpha competent *E. coli* and grown overnight on LB/Agar/ampicillin in Petri dish. Isolated colonies were grown in liquid medium, plasmids were isolated and nucleotide sequence was performed to confirm the presence of the fc1-nanoKAZ or fc10-nanoKAZ-fc1-jaz573, fc10-jaz573 inserts.

The full sequence of anti-IgG nanobody luciferase tandem FC1-nanoKAZ or FC10-nanoKAZ ([nanobody anti-IgG]-[nanoKAZ-]-[His6]) are shown as examples in the table below:

| | |
|---|---|
| Nucleotide sequence of fc1-nanoKAZ (SEQ ID NO: 53) Fc1 in underlined nanoKAZ in bold | ATGCAGGTCCAATTGCAAGA<br>GTCAGGGGGCGGCCTGGTCC<br>AACCAGGCGGTAGCCTCCGC<br>CTGTCGTGCGCGGCCTCCGG<br>GGGTACATCTATTCGTATCG<br>GTTCGATTAATGCACTGGCT<br>TGGTACCGGCAGGCTTTAGG<br>CAATCAGCGCGAACTGGTTG<br>CAGCGGTGACCGAAGGCGGT<br>AGCACGAACTATGCCGATTT<br>TGTAAAAGGACGTTTCACCA<br>TCAGCCGCGATAACGCGCAG<br>AACATGATGTATCTTCAGAT<br>GAATTCCCTGAAACCGGAAG<br>ATACGGCAGTTTATTATTGT<br>AATGCGGACAAGGTACTGTA<br>CTCTCGTGGCGGATACTATA<br>GCGTGGCCAACGACCTATGG<br>GGTCAGGGCACCCAGGTGAC<br>TGTGAGTAGT**ATGGTTTTCA**<br>**CCCTTGAAGACTTCGTGGGC** |

-continued

| | |
|---|---|
| | GACTGGCGCCAGACGGCGGG<br>TTACAATCTCGATCAGGTGC<br>TCGAACAAGGAGGTGTAAGT<br>TCCCTGTTCCAAAACTTGGG<br>GGTTTCTGTCACTCCAATCC<br>AGCGGATCGTGTTGAGCGGG<br>GAAAATGGTTTAAAAATCGA<br>TATCCACGTGATTATCCCGT<br>ATGAAGGCCTGTCAGGCGAC<br>CAGATGGGACAGATAGAAAA<br>AATCTTTAAAGTTGTATATC<br>CGGTTGACGATCACCATTTT<br>AAAGTAATCCTGCATTACGG<br>CACCCTGGTGATTGATGGGG<br>TGACTCCTAACATGATTGAT<br>TATTTTGGCCGTCCCTACGA<br>AGGCATCGCAGTCTTTGATG<br>GTAAAAAGATTACAGTGACG<br>GGTACGCTATGGAACGGCAA<br>TAAGATTATTGATGAGCGTT<br>TAATTAATCCGGATGGTTCG<br>CTGCTGTTTCGCGTCACCAT<br>TAACGGTGTCACCGGCTGGC<br>GCCTGTGCGAGCGTATTCTG<br>GCCCTCGAGCACCACCACCA<br>CCACCAC |
| Amino acid sequence of FC1-nanoKAZ (SEQ ID NO: 54) Fc1 underlined nanoKAZ in bold | MQVQLQESGGGLVQPGGSLR<br>LSCAASGGTSIRIGSINALA<br>WYRQALGNQRELVAAVTEGG<br>STNYADFVKGRFTISRDNAQ<br>NMMYLQMNSLKPEDTAVYYC<br>NADKVLYSRGGYYSVANDLW<br>GQGTQVTVSS**MVFTLEDFVG**<br>**DWRQTAGYNLDQVLEQGGVS**<br>**SLFQNLGVSVTPIQRIVLSG**<br>**ENGLKIDIHVIIPYEGLSGD**<br>**QMGQIEKIFKVVYPVDDHHF**<br>**KVILHYGTLVIDGVTPNMID**<br>**YFGRPYEGIAVFDGKKITVT**<br>**GTLWNGNKIIDERLINPDGS**<br>**LLFRVTINGVTGWRLCERIL**<br>**ALEHHHHHH** |
| Nucleotide sequence of fc10-nanoKAZ (SEQ ID NO: 55) Fc10in underlined nanoKAZ in bold | ATGCAAGTACAGTTGCAGGA<br>GAGTGGAGGCGGATTAGTAC<br>AAGCTGGCGATTCTCTTCGG<br>ATTTCGTGTCGCGCATCGGG<br>TCTGACTGTGAACGATCTGT<br>ATATGGGTTGGTTTCGACAG<br>GCGCCGGGCAAGGAACGCGA<br>ATTTGTCGGTCGTGTTACTC<br>CAGGGGACAACACGGACTAT<br>ACATATTACGTGGACAGCGT<br>GAAAGGGCGTTTCACCATCA<br>GCCGTGATTCCGCCAAAAAT<br>ACCGTGTATCTCCAGATGAA<br>TTCTCTGAAACTGGAAGATA<br>CCGCCGTCTACCTGTGCGCG<br>GGCCGCCGCTTCGGTAGTTC<br>CGAGTGGGATTACTGGGGTC<br>AGGGCACCCAAGTTACGGTT<br>AGCTCA**ATGGTTTTCACCCT**<br>**TGAAGACTTCGTGGGCGACT**<br>**GGCGCCAGACGGCGGGTTAC**<br>**AATCTCGATCAGGTGCTCGA**<br>**ACAAGGAGGTGTAAGTTCCC**<br>**TGTTCCAAAACTTGGGGGTT**<br>**TCTGTCACTCCAATCCAGCG**<br>**GATCGTGTTGAGCGGGGAAA**<br>**ATGGTTTAAAAATCGATATC**<br>**CACGTGATTATCCCGTATGA**<br>**AGGCCTGTCAGGCGACCAGA**<br>**TGGGACAGATAGAAAAAATC**<br>**TTTAAAGTTGTATATCCGGT**<br>**TGACGATCACCATTTTAAAG**<br>**TAATCCTGCATTACGGCACC**<br>**CTGGTGATTGATGGGGTGAC**<br>**TCCTAACATGATTGATTATT** |

-continued

| | |
|---|---|
| | **TTGGCCGTCCCTACGAAGGC**<br>**ATCGCAGTCTTTGATGGTAA**<br>**AAAGATTACAGTGACGGGTA**<br>**CGCTATGGAACGGCAATAAG**<br>**ATTATTGATGAGCGTTTAAT**<br>**TAATCCGGATGGTTCGCTGC**<br>**TGTTTCGCGTCACCATTAAC**<br>**GGTGTCACCGGCTGGCGCCT**<br>**GTGCGAGCGTATTCTGGCCC**<br>**TCGAGCACCACCACCACCAC**<br>**CAC** |
| Amino acid sequence of FC10-nanoKAZ (SEQ ID NO: 56) Fc10 underlined nanoKAZ in bold | MQVQLQESGGGLVQAGDSLR<br>ISCRASGLTVNDLYMGWFRQ<br>APGKEREFVGRVTPGDNTDY<br>TYYVDSVKGRFTISRDSAKN<br>TVYLQMNSLKLEDTAVYLCA<br>GRRFGSSEWDYWGQGTQVTV<br>SS**MVFTLEDFVGDWRQTAGY**<br>**NLDQVLEQGGVSSLFQNLGV**<br>**SVTPIQRIVLSGENGLKIDI**<br>**HVIIPYEGLSGDQMGQIEKI**<br>**FKVVYPVDDHHFKVILHYGT**<br>**LVIDGVTPNMIDYFGRPYEG**<br>**IAVFDGKKITVTGTLWNGNK**<br>**IIDERLINPDGSLLFRVTIN**<br>**GVTGWRLCERILALEHHHHH** |

The estimated molecular weight (MW) of FC1-nanoKAZ and FC10-nanoKAZ calculated from sequence are 34115 and 33588 Daltons respectively.

Expression, Purification and Validation of Anti-IgG Nanobody-Luciferase Fusion Proteins were Identical to Those of Anti IgE Nanobody-nanoKAZ (sdAb026-nanoKAZ)

Protocol of Detection of IgG Specific of Proteins N and S of SARS-COV2 by Luciferase Linked-Immunosorbent Assay (LuLISA)

IgG Luciferase Immunosorbent Assay (LuLISA) Protocol

White 96- or 384-well plates with flat bottom (Fluoronunc C96 Maxisorp, Nunc) were coated by adsorption with either 1 μg/mL of Nucleoprotein, Spike or their fragments, in 50 μL/well of phosphate buffer saline pH 7.4 (Sigma) for 2 hours at room temperature or overnight at 4° C. Adsorption on Maxisorp® plates favours charge interaction. Alternatives to adsorption are covalent binding of targets through carboxylic, amine or sulfhydryl moieties or glycosylation at the functionalized well surface or coating with poly-lysine. Wells were emptied eventually but not necessarily neutralize with BSA (1 mg/mL) or skimmed milk 3%. Wells were washed 3 to 6 times with 100 μL of PBS/Tween 20 0.1%. Dilutions of serum (typically 1/200), plasma or body fluid were incubated from 30 min to 1 hour at room temperature in their respective antigen-coated wells, 50 μL/well in phosphate buffer saline with eventually skimmed milk 3%, bovine serum albumin 1 mg/mL, bovine serum 1-3% and/or Tween 20 0.1%. Wells were washed three to six times with 100 μL PBS/Tween 20 0.1%. Purified VHH-nanoKAZ 1 ng/mL ($5\cdot10^7$ $RLU\cdot s^{-1}\cdot mL^{-1}$) in phosphate buffer saline with eventually skimmed milk 3%, bovine serum albumin 1 mg/mL or bovine serum 1-3% and/or Tween 20 0.1%, was loaded (50 μL/well) and incubated 20-30 min at room temperature. Wells were washed four times with 100 μL of PBS/Tween 20 0.1%. Plates can be stored at this step in PBS until measurements. Just before reading, each wells were emptied and loaded with 50 μL of furimazine (8-benzyl-2-(furan-2-ylmethyl)-6-phenylimidazo[1,2-a]pyrazin-3(7H)-one) at 27 μM of furimazine or 13 μM of Q108. The plate was orbitally shaked for 5 seconds and the light emission intensity was integrated 0.5-1 sec per well using a multi-well plate luminometer (LB960 Centro, Berthold).

Results

IgGs specific of protein N of SARS-CoV2 have been titrated by luciferase linked immunosorbent assay (LuLISA) in serums of the CORSER cohort (n=164; IcareB), in serums of the observation and monitoring protocol of the Intensive Medicine and Resuscitation service of Assistance Publique des Hopitaux de Paris (APHP) Cochin (n=20) in longitudinal follow-up and in serums and plasma of healthy donors of Establishment Français du Sang (EFS) sampled in December 2019 (frozen plasmas n=20, frozen serums n=20).

Results are shown in FIG. 16.

IgGs specific of protein Spike (S) of SARS-CoV2 have been titrated by LuLISA in serums from the observation and monitoring protocol of the Intensive Medicine and Resuscitation service of Assistance Publique des Hopitaux de Paris (APHP) Cochin (n=20) and in frozen serums from healthy donors of EFS (n=4).

Results are shown in FIG. 17.

The correlation between the titration of IgG specific of protein N of SARS-CoV2 and IgG specific of protein S of SARS-CoV2 in serum from APHP-Cochin (n=20) and EFS (n=4) is shown in FIG. 18.

Then it was compared the IgG of serums from patients (APHP-Cochin n=20) and frozen serums of healthy donors (EFS n=4) which were specific for SARS-CoV1 protein N and SARS CoV2 protein N as well as SARS CoV1 protein S and SARS-CoV2 protein S.

Results are shown in FIGS. 19 and 20.

An emergency test on a 96 well-plate which may be performed in 5 minutes has been assayed on serum from APHP-Cochin (n=20) and EFS (n=4) in duplicate by reducing the incubations time: 3 minutes for the incubation of sera at room temperature or even better at 37° C., 17 seconds per washing step (plate washer Zoom HT, Berthold) and 1 minute for the incubation of the anti-IgG VHH-nanoKAZ. The coefficient of determination $R^2$ was 0.75. Results are shown in FIG. 21.

REFERENCES

Throughout this application, various references describe the state of the art to which this invention pertains. The disclosures of these references are hereby incorporated by reference into the present application.

Coutant E P, Gagnot G, Hervin V, Baatallah R, Goyard S, Jacob Y, Rose T, Janin Y L. Bioluminescence Profiling of NanoKAZ/NanoLuc Luciferase Using a Chemical Library of Coelenterazine Analogues. Chemistry. 2020 Jan. 16; 26(4):948-958.

Jabs F, Plum M, Laursen N S, Jensen R K, Molgaard B, Miehe M, et al. Trapping IgE in a closed conformation by mimicking CD23 binding prevents and disrupts FcepsilonRI interaction. Nat Commun 2018; 9:7.

Canonica G W, Ansotegui I J, Pawankar R, et al. A WAO-ARIA-GA(2)LEN consensus document on molecular-based allergy diagnostics. World Allergy Organ J. van Hage M, Hamsten C, Valenta R. ImmunoCAP assays: Pros and cons in allergology. J Allergy Clin Immunol. 2017; 140(4):974-977.

Inouye S, Sato J, Sahara-Miura Y, Yoshida S, Hosoya T. Luminescence enhancement of the catalytic 19 kDa protein (KAZ) of Oplophorus luciferase by three amino acid substitutions. Biochem Biophys Res Commun. 2014; 445 (1):157-162.

Gasser P, Tarchevskaya S S, Guntern P, et al. The mechanistic and functional profile of the therapeutic anti-IgE antibody ligelizumab differs from omalizumab. Nat Commun. 2020; 11(1):165.

Mukai K, Gaudenzio N, Gupta S, et al. Assessing basophil activation by using flow cytometry and mass cytometry in blood stored 24 hours before analysis. J Allergy Clin Immunol. 2017; 139(3):889-899 e811.

Hamilton R G, Franklin Adkinson N, Jr. In vitro assays for the diagnosis of IgE-mediated disorders. J Allergy Clin Immunol. 2004; 114(2):213-225; quiz 226.

Tsai C T, Mukai K, Robinson P V, et al. Isotype-specific agglutination-PCR (ISAP): A sensitive and multiplex method for measuring allergen-specific IgE. J Allergy Clin Immunol. 2018; 141(5):1901-1904 e1915.

Li T M, Chuang T, Tse S, Hovanec-Burns D, El Shami A S. Development and validation of a third generation allergen-specific IgE assay on the continuous random access IMMULITE 2000 analyzer. Ann Clin Lab Sci. 2004; 34(1):67-74.

Tomabechi Y, Hosoya T, Ehara H, Sekine S I, Shirouzu M, Inouye S. Crystal structure of nanoKAZ: The mutated 19 kDa component of Oplophorus luciferase catalyzing the bioluminescent reaction with coelenterazine. Biochem Biophys Res Commun. 2016; 470(1):88-93.

Shimomura O, Masugi T, Johnson F H, Haneda Y., Properties and reaction mechanism of the bioluminescence system of the deep-sea shrimp Oplophorus *gracilirostris*. Biochemistry. 1978 Mar. 21; 17(6):994-8.

Hall M P, Unch J, Binkowski B F, Valley M P, Butler B L, Wood M G, Otto P, Zimmerman K, Vidugiris G, Machleidt T, Robers M B, Benink H A, Eggers C T, Slater M R, Meisenheimer P L, Klaubert D H, Fan F, Encell L P, Wood K V. Engineered luciferase reporter from a deep sea shrimp utilizing a novel imidazopyrazinone substrate. ACS Chem Biol. 2012 Nov. 16; 7(11):1848-57.

The invention claimed is:

1. A luciferase having at least 95% amino acid sequence identity to the amino acid sequence SEQ ID NO: 1 and comprising at least one amino acid substitution selected from the group consisting of:

substitution of the tyrosine (Y) at a position corresponding to the position 18 of SEQ ID NO: 1 with an arginine (R), substitution of the leucine (L) at a position corresponding to the position 48 of SEQ ID NO: 1 with a lysine (K), substitution of the tyrosine (Y) at a position corresponding to the position 116 of SEQ ID NO: 1 with a phenylalanine (F), substitution of the tryptophan (W) at a position corresponding to the position 134 of SEQ ID NO: 1 with an amino acid selected from the group consisting of a threonine (T) and glutamate (E), and substitution of the tryptophan (W) at a position corresponding to the position 163 of SEQ ID NO: 1 with an amino acid selected from the group consisting of a threonine (T) and glutamate (E).

2. The luciferase according to claim 1 wherein the luciferase has an amino acid sequence selected from the group consisting of SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

3. A method comprising the steps of:

(a) exposing the luciferase according to claim 1 to a substrate and (b) detecting luminescence.

4. A kit comprising the luciferase according to claim 1 and a substrate for the luciferase.

5. The kit according to claim 4, wherein the substrate is 8-(2,3-difluorobenzyl)-2-((5-methylfuran-2-yl)methyl)-6-phenylimidazo[1,2-a] pyrazin-3(7H)-one.

6. The luciferase according to claim 1, wherein the tryptophan (W) at a position corresponding to the position 134 of SEQ ID NO: 1 is substituted with a glutamate (E) and/or the tryptophan (W) at a position corresponding to the position 163 of SEQ ID NO: 1 is substituted with a glutamate (E).

7. The luciferase according to claim 1, wherein the tyrosine (Y) at a position corresponding to the position 18 of SEQ ID NO: 1 is substituted with an arginine (R), the leucine (L) at a position corresponding to the position 48 of SEQ ID NO: 1 is substituted with a lysine (K), the tryptophan (W) at a position corresponding to the position 134 of SEQ ID NO: 1 is substituted with a glutamate (E) and the tryptophan (W) at a position corresponding to the position 163 of SEQ ID NO: 1 is substituted with a glutamate (E).

8. The luciferase according to claim 1, wherein the tyrosine (Y) at a position corresponding to the position 18 of SEQ ID NO: 1 is substituted with an arginine (R), the leucine (L) at a position corresponding to the position 48 of SEQ ID NO: 1 is substituted with a lysine (K), the tyrosine (Y) at a position corresponding to the position 116 of SEQ ID NO: 1 is substituted with a phenylalanine (F), the tryptophan (W) at a position corresponding to the position 134 of SEQ ID NO: 1 is substituted with a glutamate (E) and the tryptophan (W) at a position corresponding to the position 163 of SEQ ID NO: 1 is substituted with a glutamate (E).

9. The luciferase according to claim 1, wherein the tyrosine (Y) at a position corresponding to the position 18 of SEQ ID NO: 1 is substituted with an arginine (R), the leucine (L) at a position corresponding to the position 48 of SEQ ID NO: 1 is substituted with a lysine (K), the tyrosine (Y) at a position corresponding to the position 116 of SEQ ID NO: 1 is substituted with a phenylalanine (F), the tryptophan (W) at a position corresponding to the position 134 of SEQ ID NO: 1 is substituted with a glutamate (E), the tryptophan (W) at a position corresponding to the position 163 of SEQ ID NO: 1 is substituted with a glutamate (E) and the cysteine (C) at a position corresponding to the position 166 of SEQ ID NO: 1 is substituted with a serine (S).

10. A fusion protein comprising:

a N-terminal domain which comprises an antibody which is a variable domain of a camelidae heavy-chain antibody (VHH) or a single chain variable fragment (scFV) and wherein the antibody targets an immunoglobulin and a C-terminal domain which comprises the luciferase of claim 1.

11. A kit comprising:

the fusion protein according to claim 10 and a substrate for the polypeptide with a luciferase activity.

12. A method for detecting the presence of an immunoglobulin in a sample comprising the steps of:

(a) contacting the sample with the fusion protein according to claim 10, (b) adding a substrate for the polypeptide with a luciferase activity, (c) detecting the luminescence.

13. A method for quantifying the level of an immunoglobulin in a sample comprising the steps of:

(a) contacting the sample with the fusion protein according to claim 10, (b) adding a substrate for the polypeptide with a luciferase activity, (c) quantifying the luminescence.

14. A method for quantifying the affinity range of an immunoglobulin per affinity interval in a sample for evaluating the affinity range of a polyclonal immunoglobulin mixture comprising the steps of:

(a) contacting the sample with an antigen in the presence of dilution series of the free antigen, (b) contacting the sample with the fusion protein according to claim 10, (c) adding a substrate for the polypeptide with a luciferase activity and (d) quantifying the luminescence and (e) plotting the luminescence intensity versus antigen concentration, thereby quantifying the affinity for the antigen range of the immunoglobulin in the sample.

15. A fusion protein comprising:

a N-terminal domain which comprises a peptidic antigen and a C-terminal domain which comprises the luciferase of claim 1.

16. A kit comprising:

the fusion protein according to claim 15 and a substrate for the polypeptide with a luciferase activity.

17. A method for detecting the presence of an antibody in a sample comprising the steps of:

(a) contacting the sample with the fusion protein according to claim 15, (b) adding a substrate for the polypeptide with a luciferase activity, (c) detecting the luminescence, wherein the antibody is directed against the peptidic antigen.

18. A recombinant polynucleotide encoding the luciferase of claim 1.

19. A vector comprising the recombinant polynucleotide of claim 18.

20. A cell comprising the polynucleotide of claim 18.

21. The luciferase of claim 1, wherein the luciferase further comprises at least one amino acid substitution selected from the group consisting of:

substitution of the isoleucine (I) at a position corresponding to the position 56 of SEQ ID NO: 1 with an alanine (A), and substitution of the cysteine (C) at a position corresponding to the position 166 of SEQ ID NO: 1 with a serine (S).

22. The fusion protein of claim 10, wherein the antibody is a VHH.

23. The fusion protein of claim 22, wherein the VHH is directed against the constant fragment (Fc) of the immunoglobulin.

24. The fusion protein of claim 10, wherein the immunoglobulin is an IgE directed against an allergen.

* * * * *

SEQUENCE LISTING

```
<160> NUMBER OF SEQ ID NOS: 62

<210> SEQ ID NO 1
<211> LENGTH: 173
<212> TYPE: PRT
<213> ORGANISM: Artificial Sequence
<220> FEATURE:
<223> OTHER INFORMATION: luciferase

<400> SEQUENCE: 1

Met Val Phe Thr Leu Glu Asp Phe Val Gly Asp Trp Arg Gln Thr Ala
1               5                   10                  15
```

```
Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Leu Glu
                165                 170


<210> SEQ ID NO 2
<211> LENGTH: 173
<212> TYPE: PRT
<213> ORGANISM: Artificial Sequence
<220> FEATURE:
<223> OTHER INFORMATION: luciferase

<400> SEQUENCE: 2

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Phe Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Leu Glu
                165                 170


<210> SEQ ID NO 3
<211> LENGTH: 173
<212> TYPE: PRT
<213> ORGANISM: Artificial Sequence
```

```
<220> FEATURE:
<223> OTHER INFORMATION: luciferase

<400> SEQUENCE: 3

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Thr Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Leu Glu
                165                 170


<210> SEQ ID NO 4
<211> LENGTH: 173
<212> TYPE: PRT
<213> ORGANISM: Artificial Sequence
<220> FEATURE:
<223> OTHER INFORMATION: luciferase

<400> SEQUENCE: 4

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160
```

```
Thr Gly Thr Arg Leu Cys Glu Arg Ile Leu Ala Leu Glu
                165                 170


<210> SEQ ID NO 5
<211> LENGTH: 173
<212> TYPE: PRT
<213> ORGANISM: Artificial Sequence
<220> FEATURE:
<223> OTHER INFORMATION: luciferase

<400> SEQUENCE: 5

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ala Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Leu Glu
                165                 170


<210> SEQ ID NO 6
<211> LENGTH: 173
<212> TYPE: PRT
<213> ORGANISM: Artificial Sequence
<220> FEATURE:
<223> OTHER INFORMATION: luciferase

<400> SEQUENCE: 6

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110
```

```
Gly Arg Pro Phe Glu Gly Ile Ala Val Phe Asp Gly Lys Lys Ile Thr
        115                 120                 125

Val Thr Gly Thr Leu Thr Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Leu Glu
                165                 170


<210> SEQ ID NO 7
<211> LENGTH: 173
<212> TYPE: PRT
<213> ORGANISM: Artificial Sequence
<220> FEATURE:
<223> OTHER INFORMATION: luciferase

<400> SEQUENCE: 7

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Phe Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Ser Glu Arg Ile Leu Ala Leu Glu
                165                 170


<210> SEQ ID NO 8
<211> LENGTH: 173
<212> TYPE: PRT
<213> ORGANISM: Artificial Sequence
<220> FEATURE:
<223> OTHER INFORMATION: luciferase

<400> SEQUENCE: 8

Met Val Phe Thr Leu Glu Asp Phe Val Gly Asp Trp Arg Gln Thr Ala
1               5                   10                  15

Gly Arg Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Lys
        35                  40                  45

Ser Gly Glu Asn Gly Leu Lys Ile Asp Ile His Val Ile Ile Pro Tyr
    50                  55                  60
```

```
Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Glu Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Glu Arg Leu Cys Glu Arg Ile Leu Ala Leu Glu
                165                 170


<210> SEQ ID NO 9
<211> LENGTH: 173
<212> TYPE: PRT
<213> ORGANISM: Artificial Sequence
<220> FEATURE:
<223> OTHER INFORMATION: luciferase

<400> SEQUENCE: 9

Met Val Phe Thr Leu Glu Asp Phe Val Gly Asp Trp Arg Gln Thr Ala
1               5                   10                  15

Gly Arg Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Lys
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Glu Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Glu Arg Leu Ser Glu Arg Ile Leu Ala Leu Glu
                165                 170


<210> SEQ ID NO 10
<211> LENGTH: 173
<212> TYPE: PRT
<213> ORGANISM: Artificial Sequence
<220> FEATURE:
<223> OTHER INFORMATION: luciferase

<400> SEQUENCE: 10

Met Val Phe Thr Leu Glu Asp Phe Val Gly Asp Trp Arg Gln Thr Ala
1               5                   10                  15
```

```
Gly Arg Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Lys
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Phe Glu Gly Ile Ala Val Phe Asp Gly Lys Lys Ile Thr
        115                 120                 125

Val Thr Gly Thr Leu Glu Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Glu Arg Leu Cys Glu Arg Ile Leu Ala Leu Glu
                165                 170


<210> SEQ ID NO 11
<211> LENGTH: 173
<212> TYPE: PRT
<213> ORGANISM: Artificial Sequence
<220> FEATURE:
<223> OTHER INFORMATION: luciferase

<400> SEQUENCE: 11

Met Val Phe Thr Leu Glu Asp Phe Val Gly Asp Trp Arg Gln Thr Ala
1               5                   10                  15

Gly Arg Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Lys
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Phe Glu Gly Ile Ala Val Phe Asp Gly Lys Lys Ile Thr
        115                 120                 125

Val Thr Gly Thr Leu Glu Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Glu Arg Leu Ser Glu Arg Ile Leu Ala Leu Glu
                165                 170


<210> SEQ ID NO 12
<211> LENGTH: 173
<212> TYPE: PRT
<213> ORGANISM: Artificial Sequence
```

<220> FEATURE:
<223> OTHER INFORMATION: luciferase

<400> SEQUENCE: 12

```
Met Val Phe Thr Leu Glu Asp Phe Val Gly Asp Trp Arg Gln Thr Ala
1               5                   10                  15

Gly Arg Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Leu Glu
                165                 170
```

<210> SEQ ID NO 13
<211> LENGTH: 173
<212> TYPE: PRT
<213> ORGANISM: Artificial Sequence
<220> FEATURE:
<223> OTHER INFORMATION: luciferase

<400> SEQUENCE: 13

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Lys
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160
```

```
Thr Gly Trp Arg Leu Cys Glu Arg Ile Leu Ala Leu Glu
                165                 170


<210> SEQ ID NO 14
<211> LENGTH: 173
<212> TYPE: PRT
<213> ORGANISM: Artificial Sequence
<220> FEATURE:
<223> OTHER INFORMATION: luciferase

<400> SEQUENCE: 14

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ala Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Thr Arg Leu Cys Glu Arg Ile Leu Ala Leu Glu
                165                 170


<210> SEQ ID NO 15
<211> LENGTH: 173
<212> TYPE: PRT
<213> ORGANISM: Artificial Sequence
<220> FEATURE:
<223> OTHER INFORMATION: luciferase

<400> SEQUENCE: 15

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110
```

```
Gly Arg Pro Tyr Glu Gly Ile Ala Val Phe Asp Gly Lys Lys Ile Thr
        115                 120                 125

Val Thr Gly Thr Leu Glu Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Leu Glu
                165                 170


<210> SEQ ID NO 16
<211> LENGTH: 173
<212> TYPE: PRT
<213> ORGANISM: Artificial Sequence
<220> FEATURE:
<223> OTHER INFORMATION: luciferase

<400> SEQUENCE: 16

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Glu Arg Leu Cys Glu Arg Ile Leu Ala Leu Glu
                165                 170


<210> SEQ ID NO 17
<211> LENGTH: 173
<212> TYPE: PRT
<213> ORGANISM: Artificial Sequence
<220> FEATURE:
<223> OTHER INFORMATION: luciferase

<400> SEQUENCE: 17

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60
```

```
Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Ser Glu Arg Ile Leu Ala Leu Glu
                165                 170


<210> SEQ ID NO 18
<211> LENGTH: 6
<212> TYPE: PRT
<213> ORGANISM: Artificial Sequence
<220> FEATURE:
<223> OTHER INFORMATION: tag

<400> SEQUENCE: 18

His His His His His His
1               5


<210> SEQ ID NO 19
<211> LENGTH: 15
<212> TYPE: PRT
<213> ORGANISM: Artificial Sequence
<220> FEATURE:
<223> OTHER INFORMATION: tag

<400> SEQUENCE: 19

Gly Leu Asn Asp Ile Phe Glu Ala Gln Lys Ile Glu Trp His Glu
1               5                   10                  15


<210> SEQ ID NO 20
<211> LENGTH: 37
<212> TYPE: PRT
<213> ORGANISM: Artificial Sequence
<220> FEATURE:
<223> OTHER INFORMATION: tag

<400> SEQUENCE: 20

Asp Glu Lys Thr Thr Gly Trp Arg Gly Gly His Val Val Glu Gly Leu
1               5                   10                  15

Ala Gly Glu Leu Glu Gln Leu Arg Ala Arg Leu Glu His His Pro Gln
            20                  25                  30

Gly Gln Arg Glu Pro
        35


<210> SEQ ID NO 21
<211> LENGTH: 28
<212> TYPE: PRT
<213> ORGANISM: Artificial Sequence
<220> FEATURE:
<223> OTHER INFORMATION: tag

<400> SEQUENCE: 21

Trp Ser His Pro Gln Phe Glu Lys Gly Gly Gly Ser Gly Gly Gly Ser
1               5                   10                  15
```

```
Gly Gly Ser Ala Trp Ser His Pro Gln Phe Glu Lys
            20                  25


<210> SEQ ID NO 22
<211> LENGTH: 9
<212> TYPE: PRT
<213> ORGANISM: Artificial Sequence
<220> FEATURE:
<223> OTHER INFORMATION: tag

<400> SEQUENCE: 22

Tyr Pro Tyr Asp Val Pro Asp Tyr Ala
1               5


<210> SEQ ID NO 23
<211> LENGTH: 10
<212> TYPE: PRT
<213> ORGANISM: Artificial Sequence
<220> FEATURE:
<223> OTHER INFORMATION: tag

<400> SEQUENCE: 23

Glu Gln Lys Leu Ile Ser Glu Glu Asp Leu
1               5                   10


<210> SEQ ID NO 24
<211> LENGTH: 5
<212> TYPE: PRT
<213> ORGANISM: Artificial Sequence
<220> FEATURE:
<223> OTHER INFORMATION: linker

<400> SEQUENCE: 24

Ala Ala Ala Gly Ser
1               5


<210> SEQ ID NO 25
<211> LENGTH: 5
<212> TYPE: PRT
<213> ORGANISM: Artificial Sequence
<220> FEATURE:
<223> OTHER INFORMATION: linker

<400> SEQUENCE: 25

Gly Gly Gly Gly Ser
1               5


<210> SEQ ID NO 26
<211> LENGTH: 10
<212> TYPE: PRT
<213> ORGANISM: Artificial Sequence
<220> FEATURE:
<223> OTHER INFORMATION: linker

<400> SEQUENCE: 26

Gly Gly Gly Gly Ser Gly Gly Gly Gly Ser
1               5                   10


<210> SEQ ID NO 27
<211> LENGTH: 5
<212> TYPE: PRT
<213> ORGANISM: Artificial Sequence
<220> FEATURE:
<223> OTHER INFORMATION: cleavage site
```

<400> SEQUENCE: 27

Leu Val Pro Arg Gly
1 5

<210> SEQ ID NO 28
<211> LENGTH: 8
<212> TYPE: PRT
<213> ORGANISM: Artificial Sequence
<220> FEATURE:
<223> OTHER INFORMATION: cleavage site

<400> SEQUENCE: 28

Gly Ser Leu Val Pro Arg Gly Ser
1 5

<210> SEQ ID NO 29
<211> LENGTH: 11
<212> TYPE: PRT
<213> ORGANISM: Artificial Sequence
<220> FEATURE:
<223> OTHER INFORMATION: cleavage site

<400> SEQUENCE: 29

Ala Ala Ala Gly Ser Leu Val Pro Arg Gly Ser
1 5 10

<210> SEQ ID NO 30
<211> LENGTH: 14
<212> TYPE: PRT
<213> ORGANISM: Artificial Sequence
<220> FEATURE:
<223> OTHER INFORMATION: cleavage site

<400> SEQUENCE: 30

Gly Gly Gly Gly Ser Leu Val Pro Arg Gly Gly Gly Gly Ser
1 5 10

<210> SEQ ID NO 31
<211> LENGTH: 521
<212> TYPE: DNA
<213> ORGANISM: Artificial Sequence
<220> FEATURE:
<223> OTHER INFORMATION: luciferase

<400> SEQUENCE: 31
atggttttca cccttgaaga cttcgtgggc gactggcgcc agacggcggg ttacaatctc 60
gatcaggtgc tcgaacaagg aggtgtaagt tccctgttcc aaaacttggg ggtttctgtc 120
actccaatcc agcggatcgt gttgagcggg gaaaatggtt taaaaatcga tatccacgtg 180
attatcccgt atgaaggcct gtcaggcgac cagatgggac agatagaaaa aatctttaaa 240
gttgtatatc cggttgacga tcaccatttt aaagtaatcc tgcattacgg caccctggtg 300
attgatgggg tgactcctaa catgattgat tattttggcc gtccctacga aggcatcgca 360
gtctttgatg gtaaaaagat tacagtgacg ggtacgctat ggaacggcaa taagattatt 420
gatgagcgtt taattaatcc ggatggttcg ctgctgtttc gcgtcaccat taacggtgtc 480
accggctggc gcctgtgcga gcgtattctg gccctcgagc a 521

<210> SEQ ID NO 32
<211> LENGTH: 521
<212> TYPE: DNA
<213> ORGANISM: Artificial Sequence
<220> FEATURE:

<223> OTHER INFORMATION: luciferase

<400> SEQUENCE: 32
atggttttca cccttgaaga cttcgtgggc gactggcgcc agacggcggg ttacaatctc 60
gatcaggtgc tcgaacaagg aggtgtaagt tccctgttcc aaaacttggg ggtttctgtc 120
actccaatcc agcggatcgt gttgagcggg gaaaatggtt taaaaatcga tatccacgtg 180
attatcccgt atgaaggcct gtcaggcgac cagatgggac agatagaaaa aatctttaaa 240
gttgtatatc cggttgacga tcaccatttt aaagtaatcc tgcattacgg caccctggtg 300
attgatgggg tgactcctaa catgattgat tattttggcc gtccctttga aggcatcgca 360
gtctttgatg gtaaaaagat tacagtgacg ggtacgctat ggaacggcaa taagattatt 420
gatgagcgtt taattaatcc ggatggttcg ctgctgtttc gcgtcaccat taacggtgtc 480
accggctggc gcctgtgcga gcgtattctg gccctcgagc a 521

<210> SEQ ID NO 33
<211> LENGTH: 521
<212> TYPE: DNA
<213> ORGANISM: Artificial Sequence
<220> FEATURE:
<223> OTHER INFORMATION: luciferase

<400> SEQUENCE: 33
atggttttca cccttgaaga cttcgtgggc gactggcgcc agacggcggg ttacaatctc 60
gatcaggtgc tcgaacaagg aggtgtaagt tccctgttcc aaaacttggg ggtttctgtc 120
actccaatcc agcggatcgt gttgagcggg gaaaatggtt taaaaatcga tatccacgtg 180
attatcccgt atgaaggcct gtcaggcgac cagatgggac agatagaaaa aatctttaaa 240
gttgtatatc cggttgacga tcaccatttt aaagtaatcc tgcattacgg caccctggtg 300
attgatgggg tgactcctaa catgattgat tattttggcc gtccctacga aggcatcgca 360
gtctttgatg gtaaaaagat tacagtgacg ggtacgctaa ccaacggcaa taagattatt 420
gatgagcgtt taattaatcc ggatggttcg ctgctgtttc gcgtcaccat taacggtgtc 480
accggctggc gcctgtgcga gcgtattctg gccctcgagc a 521

<210> SEQ ID NO 34
<211> LENGTH: 521
<212> TYPE: DNA
<213> ORGANISM: Artificial Sequence
<220> FEATURE:
<223> OTHER INFORMATION: luciferase

<400> SEQUENCE: 34
atggttttca cccttgaaga cttcgtgggc gactggcgcc agacggcggg ttacaatctc 60
gatcaggtgc tcgaacaagg aggtgtaagt tccctgttcc aaaacttggg ggtttctgtc 120
actccaatcc agcggatcgt gttgagcggg gaaaatggtt taaaaatcga tatccacgtg 180
attatcccgt atgaaggcct gtcaggcgac cagatgggac agatagaaaa aatctttaaa 240
gttgtatatc cggttgacga tcaccatttt aaagtaatcc tgcattacgg caccctggtg 300
attgatgggg tgactcctaa catgattgat tattttggcc gtccctacga aggcatcgca 360
gtctttgatg gtaaaaagat tacagtgacg ggtacgctat ggaacggcaa taagattatt 420
gatgagcgtt taattaatcc ggatggttcg ctgctgtttc gcgtcaccat taacggtgtc 480
accggctggc gcctgtgcga gcgtattctg gccctcgagc a 521

<210> SEQ ID NO 35
<211> LENGTH: 521
<212> TYPE: DNA
<213> ORGANISM: Artificial Sequence
<220> FEATURE:
<223> OTHER INFORMATION: luciferase

<400> SEQUENCE: 35
atggttttca cccttgaaga cttcgtgggc gactggcgcc agacggcggg ttacaatctc 60
gatcaggtgc tcgaacaagg aggtgtaagt tccctgttcc aaaacttggg ggtttctgtc 120
actccaatcc agcggatcgt gttgagcggg gaaaatggtt taaaaatcga tatccacgtg 180
attatcccgt atgaaggcct gtcaggcgac cagatgggac agatagaaaa aatctttaaa 240
gttgtatatc cggttgacga tcaccatttt aaagtaatcc tgcattacgg caccctggtg 300
attgatgggg tgactcctaa catgattgat tattttggcc gtccctttga aggcatcgca 360
gtctttgatg gtaaaaagat tacagtgacg ggtacgctat ggaacggcaa taagattatt 420
gatgagcgtt taattaatcc ggatggttcg ctgctgtttc gcgtcaccat taacggtgtc 480
accggctggc gcctgtgcga gcgtattctg gccctcgagc a 521

<210> SEQ ID NO 36
<211> LENGTH: 521
<212> TYPE: DNA
<213> ORGANISM: Artificial Sequence
<220> FEATURE:
<223> OTHER INFORMATION: luciferase

<400> SEQUENCE: 36
atggttttca cccttgaaga cttcgtgggc gactggcgcc agacggcggg ttacaatctc 60
gatcaggtgc tcgaacaagg aggtgtaagt tccctgttcc aaaacttggg ggtttctgtc 120
actccaatcc agcggatcgt gttgagcggg gaaaatggtt taaaaatcga tatccacgtg 180
attatcccgt atgaaggcct gtcaggcgac cagatgggac agatagaaaa aatctttaaa 240
gttgtatatc cggttgacga tcaccatttt aaagtaatcc tgcattacgg caccctggtg 300
attgatgggg tgactcctaa catgattgat tattttggcc gtccctttga aggcatcgca 360
gtctttgatg gtaaaaagat tacagtgacg ggtacgctaa ccaacggcaa taagattatt 420
gatgagcgtt taattaatcc ggatggttcg ctgctgtttc gcgtcaccat taacggtgtc 480
accggctggc gcctgtgcga gcgtattctg gccctcgagc a 521

<210> SEQ ID NO 37
<211> LENGTH: 521
<212> TYPE: DNA
<213> ORGANISM: Artificial Sequence
<220> FEATURE:
<223> OTHER INFORMATION: luciferase

<400> SEQUENCE: 37
atggttttca cccttgaaga cttcgtgggc gactggcgcc agacggcggg ttacaatctc 60
gatcaggtgc tcgaacaagg aggtgtaagt tccctgttcc aaaacttggg ggtttctgtc 120
actccaatcc agcggatcgt gttgagcggg gaaaatggtt taaaaatcga tatccacgtg 180
attatcccgt atgaaggcct gtcaggcgac cagatgggac agatagaaaa aatctttaaa 240
gttgtatatc cggttgacga tcaccatttt aaagtaatcc tgcattacgg caccctggtg 300
attgatgggg tgactcctaa catgattgat tattttggcc gtccctttga aggcatcgca 360
gtctttgatg gtaaaaagat tacagtgacg ggtacgctat ggaacggcaa taagattatt 420

```
gatgagcgtt taattaatcc ggatggttcg ctgctgtttc gcgtcaccat taacggtgtc    480

accggctggc gcctgagcga gcgtattctg gccctcgagc a                        521


<210> SEQ ID NO 38
<211> LENGTH: 521
<212> TYPE: DNA
<213> ORGANISM: Artificial Sequence
<220> FEATURE:
<223> OTHER INFORMATION: luciferase

<400> SEQUENCE: 38

atggtcttca cattagagga ctttgtggga gactggcgcc aaaccgccgg gaggaacttg     60

gaccaggtac tagagcaggg cggcgtaagc tccttgttcc agaatctcgg agtcagtgtt    120

acgccgatcc aacgaatcgt taagtctggc gagaacggac ttaaaataga tatccatgtg    180

attataccct acgaaggtct gtcaggggat cagatgggtc agattgaaaa gatctttaag    240

gtggtttacc ccgtcgatga tcaccatttt aaagtgattc tccactacgg tacccttgtg    300

attgacgggg tcactccaaa catgatagat tattttggcc ggccttatga gggaattgca    360

gtgttcgatg ggaaaaagat taccgtgacc ggcactctgg aaaacgggaa taagatcatc    420

gacgaacgtc tgattaatcc tgacggaagc ctgctgttca gggtgacaat caatggcgtg    480

acaggcgaga gactgtgcga gagaatcctc gctctcgagc a                        521


<210> SEQ ID NO 39
<211> LENGTH: 521
<212> TYPE: DNA
<213> ORGANISM: Artificial Sequence
<220> FEATURE:
<223> OTHER INFORMATION: luciferase

<400> SEQUENCE: 39

atggtcttca cattagagga ctttgtggga gactggcgcc aaaccgccgg gaggaacttg     60

gaccaggtac tagagcaggg cggcgtaagc tccttgttcc agaatctcgg agtcagtgtt    120

acgccgatcc aacgaatcgt taagtctggc gagaacggac ttaaaataga tatccatgtg    180

attataccct acgaaggtct gtcaggggat cagatgggtc agattgaaaa gatctttaag    240

gtggtttacc ccgtcgatga tcaccatttt aaagtgattc tccactacgg tacccttgtg    300

attgacgggg tcactccaaa catgatagat tattttggcc ggccttatga gggaattgca    360

gtgttcgatg ggaaaaagat taccgtgacc ggcactctgg aaaacgggaa taagatcatc    420

gacgaacgtc tgattaatcc tgacggaagc ctgctgttca gggtgacaat caatggcgtg    480

acaggcgaga gactgagcga gagaatcctc gctctcgagc a                        521


<210> SEQ ID NO 40
<211> LENGTH: 521
<212> TYPE: DNA
<213> ORGANISM: Artificial Sequence
<220> FEATURE:
<223> OTHER INFORMATION: luciferase

<400> SEQUENCE: 40

atggtcttca cattagagga ctttgtggga gactggcgcc aaaccgccgg gaggaacttg     60

gaccaggtac tagagcaggg cggcgtaagc tccttgttcc agaatctcgg agtcagtgtt    120

acgccgatcc aacgaatcgt taagtctggc gagaacggac ttaaaataga tatccatgtg    180

attataccct acgaaggtct gtcaggggat cagatgggtc agattgaaaa gatctttaag    240

gtggtttacc ccgtcgatga tcaccatttt aaagtgattc tccactacgg tacccttgtg    300
```

```
attgacgggg tcactccaaa catgatagat tattttggcc ggccttttga gggaattgca    360

gtgttcgatg ggaaaaagat taccgtgacc ggcactctgg aaaacgggaa taagatcatc    420

gacgaacgtc tgattaatcc tgacggaagc ctgctgttca gggtgacaat caatggcgtg    480

acaggcgaga gactgtgcga gagaatcctc gctctcgagc a                        521


<210> SEQ ID NO 41
<211> LENGTH: 521
<212> TYPE: DNA
<213> ORGANISM: Artificial Sequence
<220> FEATURE:
<223> OTHER INFORMATION: luciferase

<400> SEQUENCE: 41

atggtcttca cattagagga ctttgtggga gactggcgcc aaaccgccgg gaggaacttg     60

gaccaggtac tagagcaggg cggcgtaagc tccttgttcc agaatctcgg agtcagtgtt    120

acgccgatcc aacgaatcgt taagtctggc gagaacggac ttaaaataga tatccatgtg    180

attataccct acgaaggtct gtcaggggat cagatgggtc agattgaaaa gatctttaag    240

gtggtttacc ccgtcgatga tcaccatttt aaagtgattc tccactacgg tacccttgtg    300

attgacgggg tcactccaaa catgatagat tattttggcc ggccttttga gggaattgca    360

gtgttcgatg ggaaaaagat taccgtgacc ggcactctgg aaaacgggaa taagatcatc    420

gacgaacgtc tgattaatcc tgacggaagc ctgctgttca gggtgacaat caatggcgtg    480

acaggcgaga gactgagcga gagaatcctc gctctcgagc a                        521


<210> SEQ ID NO 42
<211> LENGTH: 347
<212> TYPE: PRT
<213> ORGANISM: Artificial Sequence
<220> FEATURE:
<223> OTHER INFORMATION: luciferase

<400> SEQUENCE: 42

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Gly Gly Ser Pro Gly
                165                 170                 175
```

```
Val Phe Thr Leu Glu Asp Phe Val Gly Asp Trp Arg Gln Thr Ala Gly
            180                 185                 190

Tyr Asn Leu Asp Gln Val Leu Glu Gln Gly Gly Val Ser Ser Leu Phe
        195                 200                 205

Gln Asn Leu Gly Val Ser Val Thr Pro Ile Gln Arg Ile Val Leu Ser
    210                 215                 220

Gly Glu Asn Gly Leu Lys Ile Asp Ile His Val Ile Ile Pro Tyr Glu
225                 230                 235                 240

Gly Leu Ser Gly Asp Gln Met Gly Gln Ile Glu Lys Ile Phe Lys Val
                245                 250                 255

Val Tyr Pro Val Asp Asp His His Phe Lys Val Ile Leu His Tyr Gly
            260                 265                 270

Thr Leu Val Ile Asp Gly Val Thr Pro Asn Met Ile Asp Tyr Phe Gly
        275                 280                 285

Arg Pro Tyr Glu Gly Ile Ala Val Phe Asp Gly Lys Lys Ile Thr Val
    290                 295                 300

Thr Gly Thr Leu Trp Asn Gly Asn Lys Ile Ile Asp Glu Arg Leu Ile
305                 310                 315                 320

Asn Pro Asp Gly Ser Leu Leu Phe Arg Val Thr Ile Asn Gly Val Thr
                325                 330                 335

Gly Trp Arg Leu Cys Glu Arg Ile Leu Ala Val
            340                 345
```

<210> SEQ ID NO 43
<211> LENGTH: 347
<212> TYPE: PRT
<213> ORGANISM: Artificial Sequence
<220> FEATURE:
<223> OTHER INFORMATION: luciferase

<400> SEQUENCE: 43

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Phe Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Gly Gly Ser Pro Gly
                165                 170                 175

Val Phe Thr Leu Glu Asp Phe Val Gly Asp Trp Arg Gln Thr Ala Gly
            180                 185                 190
```

```
Tyr Asn Leu Asp Gln Val Leu Glu Gln Gly Gly Val Ser Ser Leu Phe
        195                 200                 205

Gln Asn Leu Gly Val Ser Val Thr Pro Ile Gln Arg Ile Val Leu Ser
    210                 215                 220

Gly Glu Asn Gly Leu Lys Ile Asp Ile His Val Ile Ile Pro Tyr Glu
225                 230                 235                 240

Gly Leu Ser Gly Asp Gln Met Gly Gln Ile Glu Lys Ile Phe Lys Val
                245                 250                 255

Val Tyr Pro Val Asp Asp His His Phe Lys Val Ile Leu His Tyr Gly
            260                 265                 270

Thr Leu Val Ile Asp Gly Val Thr Pro Asn Met Ile Asp Tyr Phe Gly
        275                 280                 285

Arg Pro Phe Glu Gly Ile Ala Val Phe Asp Gly Lys Lys Ile Thr Val
    290                 295                 300

Thr Gly Thr Leu Trp Asn Gly Asn Lys Ile Ile Asp Glu Arg Leu Ile
305                 310                 315                 320

Asn Pro Asp Gly Ser Leu Leu Phe Arg Val Thr Ile Asn Gly Val Thr
                325                 330                 335

Gly Trp Arg Leu Cys Glu Arg Ile Leu Ala Val
            340                 345


<210> SEQ ID NO 44
<211> LENGTH: 522
<212> TYPE: PRT
<213> ORGANISM: Artificial Sequence
<220> FEATURE:
<223> OTHER INFORMATION: luciferase

<400> SEQUENCE: 44

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Gly Gly Ser Pro Gly
                165                 170                 175

Val Phe Thr Leu Glu Asp Phe Val Gly Asp Trp Arg Gln Thr Ala Gly
            180                 185                 190

Tyr Asn Leu Asp Gln Val Leu Glu Gln Gly Gly Val Ser Ser Leu Phe
        195                 200                 205
```

```
Gln Asn Leu Gly Val Ser Val Thr Pro Ile Gln Arg Ile Val Leu Ser
    210                 215                 220

Gly Glu Asn Gly Leu Lys Ile Asp Ile His Val Ile Ile Pro Tyr Glu
225                 230                 235                 240

Gly Leu Ser Gly Asp Gln Met Gly Gln Ile Glu Lys Ile Phe Lys Val
                245                 250                 255

Val Tyr Pro Val Asp Asp His His Phe Lys Val Ile Leu His Tyr Gly
            260                 265                 270

Thr Leu Val Ile Asp Gly Val Thr Pro Asn Met Ile Asp Tyr Phe Gly
        275                 280                 285

Arg Pro Tyr Glu Gly Ile Ala Val Phe Asp Gly Lys Lys Ile Thr Val
    290                 295                 300

Thr Gly Thr Leu Trp Asn Gly Asn Lys Ile Ile Asp Glu Arg Leu Ile
305                 310                 315                 320

Asn Pro Asp Gly Ser Leu Leu Phe Arg Val Thr Ile Asn Gly Val Thr
                325                 330                 335

Gly Trp Arg Leu Cys Glu Arg Ile Leu Ala Asn Ala Gly Ala Gln Val
            340                 345                 350

Phe Thr Leu Glu Asp Phe Val Gly Asp Trp Arg Gln Thr Ala Gly Tyr
        355                 360                 365

Asn Leu Asp Gln Val Leu Glu Gln Gly Gly Val Ser Ser Leu Phe Gln
    370                 375                 380

Asn Leu Gly Val Ser Val Thr Pro Ile Gln Arg Ile Val Leu Ser Gly
385                 390                 395                 400

Glu Asn Gly Leu Lys Ile Asp Ile His Val Ile Ile Pro Tyr Glu Gly
                405                 410                 415

Leu Ser Gly Asp Gln Met Gly Gln Ile Glu Lys Ile Phe Lys Val Val
            420                 425                 430

Tyr Pro Val Asp Asp His His Phe Lys Val Ile Leu His Tyr Gly Thr
        435                 440                 445

Leu Val Ile Asp Gly Val Thr Pro Asn Met Ile Asp Tyr Phe Gly Arg
    450                 455                 460

Pro Tyr Glu Gly Ile Ala Val Phe Asp Gly Lys Lys Ile Thr Val Thr
465                 470                 475                 480

Gly Thr Leu Trp Asn Gly Asn Lys Ile Ile Asp Glu Arg Leu Ile Asn
                485                 490                 495

Pro Asp Gly Ser Leu Leu Phe Arg Val Thr Ile Asn Gly Val Thr Gly
            500                 505                 510

Trp Arg Leu Cys Glu Arg Ile Leu Ala Val
        515                 520
```

<210> SEQ ID NO 45
<211> LENGTH: 522
<212> TYPE: PRT
<213> ORGANISM: Artificial Sequence
<220> FEATURE:
<223> OTHER INFORMATION: luciferase

<400> SEQUENCE: 45

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45
```

```
Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Phe Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Gly Gly Ser Pro Gly
                165                 170                 175

Val Phe Thr Leu Glu Asp Phe Val Gly Asp Trp Arg Gln Thr Ala Gly
            180                 185                 190

Tyr Asn Leu Asp Gln Val Leu Glu Gln Gly Gly Val Ser Ser Leu Phe
        195                 200                 205

Gln Asn Leu Gly Val Ser Val Thr Pro Ile Gln Arg Ile Val Leu Ser
    210                 215                 220

Gly Glu Asn Gly Leu Lys Ile Asp Ile His Val Ile Ile Pro Tyr Glu
225                 230                 235                 240

Gly Leu Ser Gly Asp Gln Met Gly Gln Ile Glu Lys Ile Phe Lys Val
                245                 250                 255

Val Tyr Pro Val Asp Asp His His Phe Lys Val Ile Leu His Tyr Gly
            260                 265                 270

Thr Leu Val Ile Asp Gly Val Thr Pro Asn Met Ile Asp Tyr Phe Gly
        275                 280                 285

Arg Pro Phe Glu Gly Ile Ala Val Phe Asp Gly Lys Lys Ile Thr Val
    290                 295                 300

Thr Gly Thr Leu Trp Asn Gly Asn Lys Ile Ile Asp Glu Arg Leu Ile
305                 310                 315                 320

Asn Pro Asp Gly Ser Leu Leu Phe Arg Val Thr Ile Asn Gly Val Thr
                325                 330                 335

Gly Trp Arg Leu Cys Glu Arg Ile Leu Ala Asn Ala Gly Ala Gln Val
            340                 345                 350

Phe Thr Leu Glu Asp Phe Val Gly Asp Trp Arg Gln Thr Ala Gly Tyr
        355                 360                 365

Asn Leu Asp Gln Val Leu Glu Gln Gly Gly Val Ser Ser Leu Phe Gln
    370                 375                 380

Asn Leu Gly Val Ser Val Thr Pro Ile Gln Arg Ile Val Leu Ser Gly
385                 390                 395                 400

Glu Asn Gly Leu Lys Ile Asp Ile His Val Ile Ile Pro Tyr Glu Gly
                405                 410                 415

Leu Ser Gly Asp Gln Met Gly Gln Ile Glu Lys Ile Phe Lys Val Val
            420                 425                 430

Tyr Pro Val Asp Asp His His Phe Lys Val Ile Leu His Tyr Gly Thr
        435                 440                 445

Leu Val Ile Asp Gly Val Thr Pro Asn Met Ile Asp Tyr Phe Gly Arg
    450                 455                 460
```

```
Pro Phe Glu Gly Ile Ala Val Phe Asp Gly Lys Lys Ile Thr Val Thr
465                 470                 475                 480

Gly Thr Leu Trp Asn Gly Asn Lys Ile Ile Asp Glu Arg Leu Ile Asn
                485                 490                 495

Pro Asp Gly Ser Leu Leu Phe Arg Val Thr Ile Asn Gly Val Thr Gly
            500                 505                 510

Trp Arg Leu Cys Glu Arg Ile Leu Ala Val
        515                 520


<210> SEQ ID NO 46
<211> LENGTH: 646
<212> TYPE: PRT
<213> ORGANISM: Artificial Sequence
<220> FEATURE:
<223> OTHER INFORMATION: luciferase

<400> SEQUENCE: 46

Met Thr Gly Gly Gln Gln Met Gly Arg Asp Leu Tyr Asp Asp Asp Asp
1               5                   10                  15

Lys Asp Pro Met Val Ser Lys Gly Glu Glu Leu Ile Lys Glu Asn Met
            20                  25                  30

Arg Ser Lys Leu Tyr Leu Glu Gly Ser Val Asn Gly His Gln Phe Lys
        35                  40                  45

Cys Thr His Glu Gly Glu Gly Lys Pro Tyr Glu Gly Lys Gln Thr Asn
    50                  55                  60

Arg Ile Lys Val Val Glu Gly Gly Pro Leu Pro Phe Ala Phe Asp Ile
65                  70                  75                  80

Leu Ala Thr His Phe Met Tyr Gly Ser Lys Val Phe Ile Lys Tyr Pro
                85                  90                  95

Ala Asp Leu Pro Asp Tyr Phe Lys Gln Ser Phe Pro Glu Gly Phe Thr
            100                 105                 110

Trp Glu Arg Val Met Val Phe Glu Asp Gly Gly Val Leu Thr Ala Thr
        115                 120                 125

Gln Asp Thr Ser Leu Gln Asp Gly Glu Leu Ile Tyr Asn Val Lys Val
    130                 135                 140

Arg Gly Val Asn Phe Pro Ala Asn Gly Pro Val Met Gln Lys Lys Thr
145                 150                 155                 160

Leu Gly Trp Glu Pro Ser Thr Glu Thr Met Tyr Pro Ala Asp Gly Gly
                165                 170                 175

Leu Glu Gly Arg Cys Asp Lys Ala Leu Lys Leu Val Gly Gly Gly His
            180                 185                 190

Leu His Val Asn Phe Lys Thr Thr Tyr Lys Ser Lys Lys Pro Val Lys
        195                 200                 205

Met Pro Gly Val His Tyr Val Asp Arg Arg Leu Glu Arg Ile Lys Glu
    210                 215                 220

Ala Asp Asn Glu Thr Tyr Val Glu Gln Tyr Glu His Ala Val Ala Arg
225                 230                 235                 240

Tyr Ser Asn Leu Gly Gly Gly Phe Thr Leu Glu Asp Phe Val Gly Asp
                245                 250                 255

Trp Arg Gln Thr Ala Gly Tyr Asn Leu Asp Gln Val Leu Glu Gln Gly
            260                 265                 270

Gly Val Ser Ser Leu Phe Gln Asn Leu Gly Val Ser Val Thr Pro Ile
        275                 280                 285

Gln Arg Ile Val Leu Ser Gly Glu Asn Gly Leu Lys Ile Asp Ile His
    290                 295                 300
```

```
Val Ile Ile Pro Tyr Glu Gly Leu Ser Gly Asp Gln Met Gly Gln Ile
305                 310                 315                 320

Glu Lys Ile Phe Lys Val Val Tyr Pro Val Asp Asp His His Phe Lys
                325                 330                 335

Val Ile Leu His Tyr Gly Thr Leu Val Ile Asp Gly Val Thr Pro Asn
            340                 345                 350

Met Ile Asp Tyr Phe Gly Arg Pro Phe Glu Gly Ile Ala Val Phe Asp
        355                 360                 365

Gly Lys Lys Ile Thr Val Thr Gly Thr Leu Trp Asn Gly Asn Lys Ile
    370                 375                 380

Ile Asp Glu Arg Leu Ile Asn Pro Asp Gly Ser Leu Leu Phe Arg Val
385                 390                 395                 400

Thr Ile Asn Gly Val Thr Gly Trp Arg Leu Cys Glu Arg Ile Leu Ala
                405                 410                 415

Arg His Glu Leu Ile Lys Glu Asn Met Arg Ser Lys Leu Tyr Leu Glu
            420                 425                 430

Gly Ser Val Asn Gly His Gln Phe Lys Cys Thr His Glu Gly Glu Gly
        435                 440                 445

Lys Pro Tyr Glu Gly Lys Gln Thr Asn Arg Ile Lys Val Val Glu Gly
    450                 455                 460

Gly Pro Leu Pro Phe Ala Phe Asp Ile Leu Ala Thr His Phe Met Tyr
465                 470                 475                 480

Gly Ser Lys Val Phe Ile Lys Tyr Pro Ala Asp Leu Pro Asp Tyr Phe
                485                 490                 495

Lys Gln Ser Phe Pro Glu Gly Phe Thr Trp Glu Arg Val Met Val Phe
            500                 505                 510

Glu Asp Gly Gly Val Leu Thr Ala Thr Gln Asp Thr Ser Leu Gln Asp
        515                 520                 525

Gly Glu Leu Ile Tyr Asn Val Lys Val Arg Gly Val Asn Phe Pro Ala
    530                 535                 540

Asn Gly Pro Val Met Gln Lys Lys Thr Leu Gly Trp Glu Pro Ser Thr
545                 550                 555                 560

Glu Thr Met Tyr Pro Ala Asp Gly Gly Leu Glu Gly Arg Cys Asp Lys
                565                 570                 575

Ala Leu Lys Leu Val Gly Gly Gly His Leu His Val Asn Phe Lys Thr
            580                 585                 590

Thr Tyr Lys Ser Lys Lys Pro Val Lys Met Pro Gly Val His Tyr Val
        595                 600                 605

Asp Arg Arg Leu Glu Arg Ile Lys Glu Ala Asp Asn Glu Thr Tyr Val
    610                 615                 620

Glu Gln Tyr Glu His Ala Val Ala Arg Tyr Ser Asn Leu Gly Gly Gly
625                 630                 635                 640

Met Asp Glu Leu Tyr Lys
                645
```

<210> SEQ ID NO 47
<211> LENGTH: 24
<212> TYPE: DNA
<213> ORGANISM: Artificial Sequence
<220> FEATURE:
<223> OTHER INFORMATION: primer

<400> SEQUENCE: 47
ctcgagcacc accaccacca ccac 24

<210> SEQ ID NO 48
<211> LENGTH: 26
<212> TYPE: DNA
<213> ORGANISM: Artificial Sequence
<220> FEATURE:
<223> OTHER INFORMATION: primer

<400> SEQUENCE: 48
ggtatatctc cttcttaaag ttaaac 26

<210> SEQ ID NO 49
<211> LENGTH: 24
<212> TYPE: DNA
<213> ORGANISM: Artificial Sequence
<220> FEATURE:
<223> OTHER INFORMATION: primer

<400> SEQUENCE: 49
atggtcttca cactcgaaga tttc 24

<210> SEQ ID NO 50
<211> LENGTH: 28
<212> TYPE: DNA
<213> ORGANISM: Artificial Sequence
<220> FEATURE:
<223> OTHER INFORMATION: primer

<400> SEQUENCE: 50
catggtatat ctccttctta aagttaaa 28

<210> SEQ ID NO 51
<211> LENGTH: 927
<212> TYPE: DNA
<213> ORGANISM: Artificial Sequence
<220> FEATURE:
<223> OTHER INFORMATION: fusion protein

<400> SEQUENCE: 51
atggcggagg tccagttgct tgagagtggt gggggtcttg ttcagccagg gggctccctt 60
cgtcttagtt gtgccgcatc cggtttcaca ttcggcaatt acgacatggc gtgggtccga 120
caagctcccg gcaaacgccc tgagtgggta tcgtctattg atacgggggg agatataaca 180
cactacgcag acagtgtgaa ggggaggttc acaatctctc gggacaacgc aaagaacacc 240
ttatacttgc agatgaatag cctgagaccg gaggacactg ctgtgtattg gtgcgctacc 300
gatgaagaat atgccctcgg cccaaacgaa tttgattatt acggacaggg aactctggtg 360
actgtgtcat cagctgccgc cctggagatg gtcttcacac tcgaagattt cgttgggggac 420 tggcgacaga cagccggcta caacctggac caagtccttg aacagggagg tgtgtccagt 480
ttgtttcaga atctcggggt gtccgtaact ccgatccaaa ggattgtcct gagcggtgaa 540
aatgggctga agatcgacat ccatgtcatc atcccgtatg aaggtctgag cggcgaccaa 600
atgggccaga tcgaaaaaat ttttaaggtg gtgtaccctg tggatgatca tcactttaag 660
gtgatcctgc actatggcac actggtaatc gacggggtta cgccgaacat gatcgactat 720
ttcggacggc cgtatgaagg catcgccgtg ttcgacggca aaaagatcac tgtaacaggg 780
accctgtgga acggcaacaa aattatcgac gagcgcctga tcaaccccga cggctccctg 840
ctgttccgag taaccatcaa cggagtgacc ggctggcggc tgtgcgaacg cattctggcg 900
ctcgagcacc accaccacca ccactga 927

<210> SEQ ID NO 52

<211> LENGTH: 308
<212> TYPE: PRT
<213> ORGANISM: Artificial Sequence
<220> FEATURE:
<223> OTHER INFORMATION: fusion protein

<400> SEQUENCE: 52

Met Ala Glu Val Gln Leu Leu Glu Ser Gly Gly Gly Leu Val Gln Pro
1 5 10 15

Gly Gly Ser Leu Arg Leu Ser Cys Ala Ala Ser Gly Phe Thr Phe Gly
20 25 30

Asn Tyr Asp Met Ala Trp Val Arg Gln Ala Pro Gly Lys Arg Pro Glu
35 40 45

Trp Val Ser Ser Ile Asp Thr Gly Gly Asp Ile Thr His Tyr Ala Asp
50 55 60

Ser Val Lys Gly Arg Phe Thr Ile Ser Arg Asp Asn Ala Lys Asn Thr
65 70 75 80

Leu Tyr Leu Gln Met Asn Ser Leu Arg Pro Glu Asp Thr Ala Val Tyr
85 90 95

Trp Cys Ala Thr Asp Glu Glu Tyr Ala Leu Gly Pro Asn Glu Phe Asp
100 105 110

Tyr Tyr Gly Gln Gly Thr Leu Val Thr Val Ser Ser Ala Ala Ala Leu
115 120 125

Glu Met Val Phe Thr Leu Glu Asp Phe Val Gly Asp Trp Arg Gln Thr
130 135 140

Ala Gly Tyr Asn Leu Asp Gln Val Leu Glu Gln Gly Gly Val Ser Ser
145 150 155 160

Leu Phe Gln Asn Leu Gly Val Ser Val Thr Pro Ile Gln Arg Ile Val
165 170 175

Leu Ser Gly Glu Asn Gly Leu Lys Ile Asp Ile His Val Ile Ile Pro
180 185 190

Tyr Glu Gly Leu Ser Gly Asp Gln Met Gly Gln Ile Glu Lys Ile Phe
195 200 205

Lys Val Val Tyr Pro Val Asp Asp His His Phe Lys Val Ile Leu His
210 215 220

Tyr Gly Thr Leu Val Ile Asp Gly Val Thr Pro Asn Met Ile Asp Tyr
225 230 235 240

Phe Gly Arg Pro Tyr Glu Gly Ile Ala Val Phe Asp Gly Lys Lys Ile
245 250 255

Thr Val Thr Gly Thr Leu Trp Asn Gly Asn Lys Ile Ile Asp Glu Arg
260 265 270

Leu Ile Asn Pro Asp Gly Ser Leu Leu Phe Arg Val Thr Ile Asn Gly
275 280 285

Val Thr Gly Trp Arg Leu Cys Glu Arg Ile Leu Ala Leu Glu His His
290 295 300

His His His His
305

<210> SEQ ID NO 53
<211> LENGTH: 927
<212> TYPE: DNA
<213> ORGANISM: Artificial Sequence
<220> FEATURE:
<223> OTHER INFORMATION: fusion protein

<400> SEQUENCE: 53
atgcaggtcc aattgcaaga gtcagggggc ggcctggtcc aaccaggcgg tagcctccgc 60
ctgtcgtgcg cggcctccgg gggtacatct attcgtatcg gttcgattaa tgcactggct 120
tggtaccggc aggctttagg caatcagcgc gaactggttg cagcggtgac cgaaggcggt 180
agcacgaact atgccgattt tgtaaaagga cgtttcacca tcagccgcga taacgcgcag 240
aacatgatgt atcttcagat gaattccctg aaaccggaag atacggcagt ttattattgt 300
aatgcggaca aggtactgta ctctcgtggc ggatactata gcgtggccaa cgacctatgg 360
ggtcagggca cccaggtgac tgtgagtagt atggttttca cccttgaaga cttcgtgggc 420
gactggcgcc agacggcggg ttacaatctc gatcaggtgc tcgaacaagg aggtgtaagt 480
tccctgttcc aaaacttggg ggtttctgtc actccaatcc agcggatcgt gttgagcggg 540
gaaaatggtt taaaaatcga tatccacgtg attatcccgt atgaaggcct gtcaggcgac 600
cagatgggac agatagaaaa aatctttaaa gttgtatatc cggttgacga tcaccatttt 660
aaagtaatcc tgcattacgg caccctggtg attgatgggg tgactcctaa catgattgat 720
tattttggcc gtccctacga aggcatcgca gtctttgatg gtaaaaagat tacagtgacg 780
ggtacgctat ggaacggcaa taagattatt gatgagcgtt taattaatcc ggatggttcg 840
ctgctgtttc gcgtcaccat taacggtgtc accggctggc gcctgtgcga gcgtattctg 900
gccctcgagc accaccacca ccaccac 927

<210> SEQ ID NO 54
<211> LENGTH: 309
<212> TYPE: PRT
<213> ORGANISM: Artificial Sequence
<220> FEATURE:
<223> OTHER INFORMATION: fusion protein

<400> SEQUENCE: 54

Met Gln Val Gln Leu Gln Glu Ser Gly Gly Gly Leu Val Gln Pro Gly
1 5 10 15

Gly Ser Leu Arg Leu Ser Cys Ala Ala Ser Gly Gly Thr Ser Ile Arg
20 25 30

Ile Gly Ser Ile Asn Ala Leu Ala Trp Tyr Arg Gln Ala Leu Gly Asn
35 40 45

Gln Arg Glu Leu Val Ala Ala Val Thr Glu Gly Gly Ser Thr Asn Tyr
50 55 60

Ala Asp Phe Val Lys Gly Arg Phe Thr Ile Ser Arg Asp Asn Ala Gln
65 70 75 80

Asn Met Met Tyr Leu Gln Met Asn Ser Leu Lys Pro Glu Asp Thr Ala
85 90 95

Val Tyr Tyr Cys Asn Ala Asp Lys Val Leu Tyr Ser Arg Gly Gly Tyr
100 105 110

Tyr Ser Val Ala Asn Asp Leu Trp Gly Gln Gly Thr Gln Val Thr Val
115 120 125

Ser Ser Met Val Phe Thr Leu Glu Asp Phe Val Gly Asp Trp Arg Gln
130 135 140

Thr Ala Gly Tyr Asn Leu Asp Gln Val Leu Glu Gln Gly Gly Val Ser
145 150 155 160

Ser Leu Phe Gln Asn Leu Gly Val Ser Val Thr Pro Ile Gln Arg Ile
165 170 175

```
Val Leu Ser Gly Glu Asn Gly Leu Lys Ile Asp Ile His Val Ile Ile
            180                 185                 190

Pro Tyr Glu Gly Leu Ser Gly Asp Gln Met Gly Gln Ile Glu Lys Ile
        195                 200                 205

Phe Lys Val Val Tyr Pro Val Asp Asp His His Phe Lys Val Ile Leu
    210                 215                 220

His Tyr Gly Thr Leu Val Ile Asp Gly Val Thr Pro Asn Met Ile Asp
225                 230                 235                 240

Tyr Phe Gly Arg Pro Tyr Glu Gly Ile Ala Val Phe Asp Gly Lys Lys
                245                 250                 255

Ile Thr Val Thr Gly Thr Leu Trp Asn Gly Asn Lys Ile Ile Asp Glu
            260                 265                 270

Arg Leu Ile Asn Pro Asp Gly Ser Leu Leu Phe Arg Val Thr Ile Asn
        275                 280                 285

Gly Val Thr Gly Trp Arg Leu Cys Glu Arg Ile Leu Ala Leu Glu His
    290                 295                 300

His His His His His
305
```

<210> SEQ ID NO 55
<211> LENGTH: 903
<212> TYPE: DNA
<213> ORGANISM: Artificial Sequence
<220> FEATURE:
<223> OTHER INFORMATION: fusion protein

<400> SEQUENCE: 55

```
atgcaagtac agttgcagga gagtggaggc ggattagtac aagctggcga ttctcttcgg     60

atttcgtgtc gcgcatcggg tctgactgtg aacgatctgt atatgggttg gtttcgacag    120

gcgccgggca aggaacgcga atttgtcggt cgtgttactc caggggacaa cacggactat    180

acatattacg tggacagcgt gaaagggcgt ttcaccatca gccgtgattc cgccaaaaat    240

accgtgtatc tccagatgaa ttctctgaaa ctggaagata ccgccgtcta cctgtgcgcg    300

ggccgccgct tcggtagttc cgagtgggat tactggggtc agggcaccca agttacggtt    360

agctcaatgg ttttcaccct tgaagacttc gtgggcgact ggcgccagac ggcgggttac    420

aatctcgatc aggtgctcga acaaggaggt gtaagttccc tgttccaaaa cttgggggtt    480

tctgtcactc caatccagcg gatcgtgttg agcggggaaa atggtttaaa aatcgatatc    540

cacgtgatta tcccgtatga aggcctgtca ggcgaccaga tgggacagat agaaaaaatc    600

tttaaagttg tatatccggt tgacgatcac cattttaaag taatcctgca ttacggcacc    660

ctggtgattg atggggtgac tcctaacatg attgattatt ttggccgtcc ctacgaaggc    720

atcgcagtct ttgatggtaa aaagattaca gtgacgggta cgctatggaa cggcaataag    780

attattgatg agcgtttaat taatccggat ggttcgctgc tgtttcgcgt caccattaac    840

ggtgtcaccg gctggcgcct gtgcgagcgt attctggccc tcgagcacca ccaccaccac    900

cac                                                                  903
```

<210> SEQ ID NO 56
<211> LENGTH: 300
<212> TYPE: PRT
<213> ORGANISM: Artificial Sequence
<220> FEATURE:
<223> OTHER INFORMATION: fusion protein

<400> SEQUENCE: 56

Met Gln Val Gln Leu Gln Glu Ser Gly Gly Gly Leu Val Gln Ala Gly
1 5 10 15

Asp Ser Leu Arg Ile Ser Cys Arg Ala Ser Gly Leu Thr Val Asn Asp
20 25 30

Leu Tyr Met Gly Trp Phe Arg Gln Ala Pro Gly Lys Glu Arg Glu Phe
35 40 45

Val Gly Arg Val Thr Pro Gly Asp Asn Thr Asp Tyr Thr Tyr Tyr Val
50 55 60

Asp Ser Val Lys Gly Arg Phe Thr Ile Ser Arg Asp Ser Ala Lys Asn
65 70 75 80

Thr Val Tyr Leu Gln Met Asn Ser Leu Lys Leu Glu Asp Thr Ala Val
85 90 95

Tyr Leu Cys Ala Gly Arg Arg Phe Gly Ser Ser Glu Trp Asp Tyr Trp
100 105 110

Gly Gln Gly Thr Gln Val Thr Val Ser Ser Met Val Phe Thr Leu Glu
115 120 125

Asp Phe Val Gly Asp Trp Arg Gln Thr Ala Gly Tyr Asn Leu Asp Gln
130 135 140

Val Leu Glu Gln Gly Gly Val Ser Ser Leu Phe Gln Asn Leu Gly Val
145 150 155 160

Ser Val Thr Pro Ile Gln Arg Ile Val Leu Ser Gly Glu Asn Gly Leu
165 170 175

Lys Ile Asp Ile His Val Ile Ile Pro Tyr Glu Gly Leu Ser Gly Asp
180 185 190

Gln Met Gly Gln Ile Glu Lys Ile Phe Lys Val Val Tyr Pro Val Asp
195 200 205

Asp His His Phe Lys Val Ile Leu His Tyr Gly Thr Leu Val Ile Asp
210 215 220

Gly Val Thr Pro Asn Met Ile Asp Tyr Phe Gly Arg Pro Tyr Glu Gly
225 230 235 240

Ile Ala Val Phe Asp Gly Lys Lys Ile Thr Val Thr Gly Thr Leu Trp
245 250 255

Asn Gly Asn Lys Ile Ile Asp Glu Arg Leu Ile Asn Pro Asp Gly Ser
260 265 270

Leu Leu Phe Arg Val Thr Ile Asn Gly Val Thr Gly Trp Arg Leu Cys
275 280 285

Glu Arg Ile Leu Ala Leu Glu His His His His His
290 295 300

<210> SEQ ID NO 57
<211> LENGTH: 129
<212> TYPE: PRT
<213> ORGANISM: Artificial Sequence
<220> FEATURE:
<223> OTHER INFORMATION: VHH

<400> SEQUENCE: 57

Met Ala Glu Val Gln Leu Leu Glu Ser Gly Gly Gly Leu Val Gln Pro
1 5 10 15

Gly Gly Ser Leu Arg Leu Ser Cys Ala Ala Ser Gly Phe Thr Phe Gly
20 25 30

Asn Tyr Asp Met Ala Trp Val Arg Gln Ala Pro Gly Lys Arg Pro Glu
35 40 45

```
Trp Val Ser Ser Ile Asp Thr Gly Gly Asp Ile Thr His Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Arg Pro Glu Asp Thr Ala Val Tyr
                85                  90                  95

Trp Cys Ala Thr Asp Glu Glu Tyr Ala Leu Gly Pro Asn Glu Phe Asp
            100                 105                 110

Tyr Tyr Gly Gln Gly Thr Leu Val Thr Val Ser Ser Ala Ala Ala Leu
        115                 120                 125

Glu


<210> SEQ ID NO 58
<211> LENGTH: 130
<212> TYPE: PRT
<213> ORGANISM: Artificial Sequence
<220> FEATURE:
<223> OTHER INFORMATION: VHH

<400> SEQUENCE: 58

Met Gln Val Gln Leu Gln Glu Ser Gly Gly Gly Leu Val Gln Pro Gly
1               5                   10                  15

Gly Ser Leu Arg Leu Ser Cys Ala Ala Ser Gly Gly Thr Ser Ile Arg
            20                  25                  30

Ile Gly Ser Ile Asn Ala Leu Ala Trp Tyr Arg Gln Ala Leu Gly Asn
        35                  40                  45

Gln Arg Glu Leu Val Ala Ala Val Thr Glu Gly Gly Ser Thr Asn Tyr
    50                  55                  60

Ala Asp Phe Val Lys Gly Arg Phe Thr Ile Ser Arg Asp Asn Ala Gln
65                  70                  75                  80

Asn Met Met Tyr Leu Gln Met Asn Ser Leu Lys Pro Glu Asp Thr Ala
                85                  90                  95

Val Tyr Tyr Cys Asn Ala Asp Lys Val Leu Tyr Ser Arg Gly Gly Tyr
            100                 105                 110

Tyr Ser Val Ala Asn Asp Leu Trp Gly Gln Gly Thr Gln Val Thr Val
        115                 120                 125

Ser Ser
    130


<210> SEQ ID NO 59
<211> LENGTH: 122
<212> TYPE: PRT
<213> ORGANISM: Artificial Sequence
<220> FEATURE:
<223> OTHER INFORMATION: VHH

<400> SEQUENCE: 59

Met Gln Val Gln Leu Gln Glu Ser Gly Gly Gly Leu Val Gln Ala Gly
1               5                   10                  15

Asp Ser Leu Arg Ile Ser Cys Arg Ala Ser Gly Leu Thr Val Asn Asp
            20                  25                  30

Leu Tyr Met Gly Trp Phe Arg Gln Ala Pro Gly Lys Glu Arg Glu Phe
        35                  40                  45

Val Gly Arg Val Thr Pro Gly Asp Asn Thr Asp Tyr Thr Tyr Tyr Val
    50                  55                  60

Asp Ser Val Lys Gly Arg Phe Thr Ile Ser Arg Asp Ser Ala Lys Asn
65                  70                  75                  80
```

```
Thr Val Tyr Leu Gln Met Asn Ser Leu Lys Leu Glu Asp Thr Ala Val
                85                  90                  95

Tyr Leu Cys Ala Gly Arg Arg Phe Gly Ser Ser Glu Trp Asp Tyr Trp
            100                 105                 110

Gly Gln Gly Thr Gln Val Thr Val Ser Ser
        115                 120


<210> SEQ ID NO 60
<211> LENGTH: 1038
<212> TYPE: DNA
<213> ORGANISM: Artificial Sequence
<220> FEATURE:
<223> OTHER INFORMATION: luciferase

<400> SEQUENCE: 60

atggtcttta ccttggaaga tttcgttgga gattggcgtc agactgcggg ttataatttg     60

gaccaagtgc tggaacaagg cggcgttagt agcctgtttc agaacctggg ggtgagcgtc    120

acgccgatcc agcgaatagt tctaagcggg gagaatggac taaaaatcga catacatgtt    180

attattccct acgaaggcct gagcggggac cagatgggcc agattgaaaa aatttttaaa    240

gttgtctacc ctgttgatga tcatcacttc aaagtcatcc tccattatgg gaccctcgtt    300

atagatgggg tcacaccaaa catgattgac tacttcggga ggccatacga gggcatagca    360

gttttcgatg gcaagaaaat aaccgtcaca ggcactctgt ggaatggaaa taagatcatc    420

gatgagcgtc ttataaatcc ggatgggtca cttctctttc gcgtgaccat aaacggcgtg    480

acagggtggc gcttatgtga acggatcttg gctgggggat cccctggtgt tttcaccctc    540

gaagacttcg ttggggactg gcggcaaaca gctgggtaca acctagacca ggtactggaa    600

caaggaggcg tctcctcatt gtttcagaac ctaggtgtat ccgtgacccc tattcagcgc    660

attgtgctgt ccggtgaaaa cggcctcaag attgacattc acgtgataat cccatatgag    720

ggactgtcag gagaccagat ggggcagatt gaaaagatct ttaaagtcgt ctaccccgtc    780

gacgatcacc actttaaggt aattctgcat tacggcactt tggtaattga tggtgtgacg    840

cctaatatga tcgactactt cggccggccc tacgaaggga tagctgtctt tgacggcaag    900

aagattacgg tcaccggaac cctgtggaat ggcaacaaga ttattgatga gagattgatt    960

aatcccgacg gttccctgct cttcagagtc actattaacg gggtaaccgg gtggcgactt   1020

tgcgagcgga tcctggca                                                 1038


<210> SEQ ID NO 61
<211> LENGTH: 1038
<212> TYPE: DNA
<213> ORGANISM: Artificial Sequence
<220> FEATURE:
<223> OTHER INFORMATION: luciferase

<400> SEQUENCE: 61

atggtcttta ccttggaaga tttcgttgga gattggcgtc agactgcggg ttataatttg     60

gaccaagtgc tggaacaagg cggcgttagt agcctgtttc agaacctggg ggtgagcgtc    120

acgccgatcc agcgaatagt tctaagcggg gagaatggac taaaaatcga catacatgtt    180

attattccct acgaaggcct gagcggggac cagatgggcc agattgaaaa aatttttaaa    240

gttgtctacc ctgttgatga tcatcacttc aaagtcatcc tccattatgg gaccctcgtt    300

atagatgggg tcacaccaaa catgattgac tacttcggga ggccattcga gggcatagca    360

gttttcgatg gcaagaaaat aaccgtcaca ggcactctgt ggaatggaaa taagatcatc    420
```

gatgagcgtc ttataaatcc ggatgggtca cttctctttc gcgtgaccat aaacggcgtg 480
acagggtggc gcttatgtga acggatcttg gctgggggat cccctggtgt tttcaccctc 540
gaagacttcg ttggggactg gcggcaaaca gctgggtaca acctagacca ggtactggaa 600
caaggaggcg tctcctcatt gtttcagaac ctaggtgtat ccgtgacccc tattcagcgc 660
attgtgctgt ccggtgaaaa cggcctcaag attgacattc acgtgataat cccatatgag 720
ggactgtcag gagaccagat ggggcagatt gaaaagatct ttaaagtcgt ctaccccgtc 780
gacgatcacc actttaaggt aattctgcat tacggcactt tggtaattga tggtgtgacg 840
cctaatatga tcgactactt cggccggccc ttcgaaggga tagctgtctt tgacggcaag 900
aagattacgg tcaccggaac cctgtggaat ggcaacaaga ttattgatga gagattgatt 960
aatcccgacg gttccctgct cttcagagtc actattaacg gggtaaccgg gtggcgactt 1020
tgcgagcgga tcctggca 1038

<210> SEQ ID NO 62
<211> LENGTH: 1569
<212> TYPE: DNA
<213> ORGANISM: Artificial Sequence
<220> FEATURE:
<223> OTHER INFORMATION: luciferase

<400> SEQUENCE: 62
atggtcttta ccttggaaga tttcgttgga gattggcgtc agactgcggg ttataatttg 60
gaccaagtgc tggaacaagg cggcgttagt agcctgtttc agaacctggg ggtgagcgtc 120
acgccgatcc agcgaatagt tctaagcggg gagaatggac taaaaatcga catacatgtt 180
attattccct acgaaggcct gagcggggac cagatgggcc agattgaaaa aatttttaaa 240
gttgtctacc ctgttgatga tcatcacttc aaagtcatcc tccattatgg gaccctcgtt 300
atagatgggg tcacaccaaa catgattgac tacttcggga ggccatacga gggcatagca 360
gttttcgatg gcaagaaaat aaccgtcaca ggcactctgt ggaatggaaa taagatcatc 420
gatgagcgtc ttataaatcc ggatgggtca cttctctttc gcgtgaccat aaacggcgtg 480
acagggtggc gcttatgtga acggatcttg gctgggggat cccctggtgt tttcaccctc 540
gaagacttcg ttggggactg gcggcaaaca gctgggtaca acctagacca ggtactggaa 600
caaggaggcg tctcctcatt gtttcagaac ctaggtgtat ccgtgacccc tattcagcgc 660
attgtgctgt ccggtgaaaa cggcctcaag attgacattc acgtgataat cccatatgag 720
ggactgtcag gagaccagat ggggcagatt gaaaagatct ttaaagtcgt ctaccccgtc 780
gacgatcacc actttaaggt aattctgcat tacggcactt tggtaattga tggtgtgacg 840
cctaatatga tcgactactt cggccggccc tacgaaggga tagctgtctt tgacggcaag 900
aagattacgg tcaccggaac cctgtggaat ggcaacaaga ttattgatga gagattgatt 960
aatcccgacg gttccctgct cttcagagtc actattaacg gggtaaccgg gtggcgactt 1020
tgcgagcgga tcctggcaaa cgccggggcc caggtgttta ccttagagga cttcgtagga 1080
gattggcgcc aaacagccgg atacaacctg gaccaggtgt tagagcaggg cggtgtgtct 1140
tctcttttcc agaatctggg tgtgtctgtg actccaatcc agagaatcgt gcttagtgga 1200
gagaatggac ttaaaatcga catccatgtg attattcctt atgagggtct cagtggtgac 1260
caaatgggcc agatcgagaa aatttttaag gtggtgtatc ctgtggatga ccaccacttc 1320
aaggtgatcc tccactatgg aaccctcgtg atcgatggag tgacaccaaa catgatcgac 1380
tatttcggca ggccctatga gggcatcgca gtgtttgatg gaaaaaagat cactgtgact 1440

-continued

```
ggaacactgt ggaatggcaa taagatcatc gatgagagac tgatcaaccc cgatggctct   1500

ctgctgttca gagtgacaat caacggcgtg acaggctgga ggctgtgcga gaggatcctg   1560

gccgtttaa                                                           1569
```